(12) United States Patent
Oh et al.

(10) Patent No.: US 8,283,102 B2
(45) Date of Patent: Oct. 9, 2012

(54) PHOTOACID GENERATOR, COPOLYMER, CHEMICALLY AMPLIFIED RESIST COMPOSITION, AND METHOD OF FORMING PATTERN USING THE CHEMICALLY AMPLIFIED RESIST COMPOSITION

(75) Inventors: Jung Hoon Oh, Cheonan-si (KR); Sang Jin Kim, Asan-si (KR); Jin Ho Kim, Asan-si (KR); Dae Hyeon Shin, Seoul (KR)

(73) Assignee: Korea Kumho Petrochemical Co., Ltd., Seoul (KR)

( * ) Notice: Subject to any disclaimer, the term of this patent is extended or adjusted under 35 U.S.C. 154(b) by 128 days.

(21) Appl. No.: 12/416,988

(22) Filed: Apr. 2, 2009

(65) Prior Publication Data
US 2010/0143843 A1 Jun. 10, 2010

(30) Foreign Application Priority Data
Dec. 4, 2008 (KR) .................. 10-2008-0122403

(51) Int. Cl.
*G03F 7/004* (2006.01)
*G03F 7/30* (2006.01)
*C08F 10/00* (2006.01)
*C07C 69/773* (2006.01)

(52) U.S. Cl. ............... 430/270.1; 430/326; 430/330; 430/905; 430/910; 430/921; 526/282; 526/286; 560/221

(58) Field of Classification Search ............... 430/270.1, 430/326, 330, 910, 921; 526/282, 286; 560/221
See application file for complete search history.

(56) References Cited

U.S. PATENT DOCUMENTS

| | | | |
|---|---|---|---|
| 5,057,146 A * | 10/1991 | Anthony et al. | 504/255 |
| 5,130,392 A * | 7/1992 | Schwalm et al. | 526/288 |
| 6,586,152 B1 * | 7/2003 | Urano et al. | 430/170 |
| 7,618,765 B2 * | 11/2009 | Nishi et al. | 430/270.1 |
| 2006/0147836 A1 * | 7/2006 | Hatakeyama et al. | 430/270.1 |
| 2009/0186296 A1 * | 7/2009 | Ohsawa et al. | 430/270.1 |
| 2009/0186297 A1 * | 7/2009 | Ohsawa et al. | 430/270.1 |
| 2009/0186298 A1 * | 7/2009 | Ohsawa et al. | 430/270.1 |
| 2009/0233223 A1 * | 9/2009 | Tachibana et al. | 430/270.1 |

* cited by examiner

*Primary Examiner* — John Chu
(74) *Attorney, Agent, or Firm* — Ladas & Parry LLP

(57) ABSTRACT

Disclosed are a photoacid generator, a copolymer, a chemically amplified resist composition, and a method of forming a pattern using the chemically amplified resist composition. The photoacid is connected with a main chain of the copolymer, whereby the photoacid is equally dispersed within a resist layer, and characteristics of line edge roughness of a resist pattern is improved.

14 Claims, 28 Drawing Sheets

PHOTOACID GENERATOR, COPOLYMER, CHEMICALLY AMPLIFIED RESIST COMPOSITION, AND METHOD OF FORMING PATTERN USING THE CHEMICALLY AMPLIFIED RESIST COMPOSITION

CROSS-REFERENCE TO RELATED APPLICATION

This application claims the benefit of Korean Patent Application No. 10-2008-0122403, filed on Dec. 4, 2008 in the Korean Intellectual Property Office, the disclosure of which is incorporated herein by reference.

BACKGROUND

1. Field of the Invention

The present invention relates to semiconductor manufacturing, and more particularly, to a photoacid generator, a copolymer, a chemically amplified resist composition, and a method of forming a pattern using the chemically amplified resist composition, which are used in manufacturing a semiconductor.

2. Description of the Related Art

Currently, a technique of forming a line width of various patterns, provided in a semiconductor, by about 50 nm or less has been developed. Because the technique of forming these fine patterns is very difficult, improvement in characteristics of resist compositions as well as improvement in performance of an exposure device may be needed.

Of these resist compositions, a chemically amplified resist composition may be generally comprised of a photoacid generator (PAG), a copolymer, a solvent, and various additives. However, according to a conventional invention, the PAG may not be equally dispersed within a resist layer when the resist layer is formed on a substrate using the chemically amplified resist composition. In this regard, characteristics of line edge roughness of a resist pattern may be deteriorated, and thus encountering a difficulty in forming fine patterns.

Also, an acrylic copolymer may be generally used as the copolymer, however, etch resistance of the resist pattern with respect to a dry plasma may be reduced due to a large amount of oxygen atoms of the acrylic copolymer. To overcome this, a thickness of the resist pattern is required to be enlarged, however, when enlarging the resist pattern, a shape thereof may be destroyed or deformed.

SUMMARY

An aspect of the present invention provides a photoacid generator (PAG) equally dispersed within a resist layer formed on a substrate in a semiconductor manufacturing process, a copolymer including the PAG, a chemically amplified resist composition including the copolymer, and a method of forming a pattern using the chemically amplified resist composition.

An aspect of the present invention also provides a PAG that may improve characteristics of line edge roughness of a resist pattern formed on a substrate in a semiconductor manufacturing process, a copolymer including the PAG, a chemically amplified resist composition including the copolymer, and a method of forming a pattern using the chemically amplified resist composition.

An aspect of the present invention further provides a PAG that may improve an etch resistance of a resist pattern formed on a substrate in a semiconductor manufacturing process, a copolymer including the PAG, a chemically amplified resist composition including the copolymer, and a method of forming a pattern using the chemically amplified resist composition.

An aspect of the present invention still provides a PAG in which a resist layer formed on a substrate in a semiconductor manufacturing process may have a high sensitivity, a high thermal stability, a high adhesive strength with respect to the substrate, a high transparence with respect to an exposure light, and a resist pattern may have a high resolution, a copolymer including the PAG, a chemically amplified resist composition including the copolymer, and a method of forming a pattern using the chemically amplified resist composition.

According to an aspect of the present invention, there is provided a PAG represented as

[Chemical formula 1]

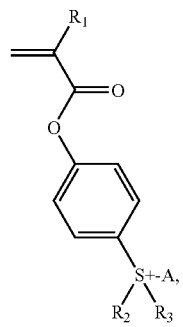

wherein $R_1$ is a hydrogen atom, a trifluoromethyl group, a $C_1$-$C_5$ alkyl group, or $C_1$-$C_5$ alkoxy group, $R_2$ and $R_3$ are respectively a linear or branched $C_1$-$C_{20}$ alkyl group, an aryl group, a linear or branched $C_1$-$C_{20}$ perfluoroalkyl group, a benzyl group, or a $C_6$-$C_{20}$ aryl group, and $A^-$ is a compound represented as

[Chemical formula 2]

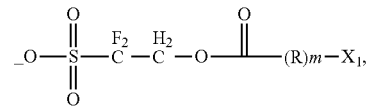

wherein $X_1$ is a monocyclic or polycyclic $C_3$-$C_{20}$ hydrocarbon group, a benzyl group, a $C_6$-$C_{20}$ aryl group, a $C_1$-$C_{10}$ alkyl group, a $C_1$-$C_{10}$ alkoxy group, a $C_1$-$C_{10}$ hydroxy alkyl group, or a cyano group, at least one hydrogen atom of the monocyclic or polycyclic $C_3$-$C_{20}$ hydrocarbon group is or is not substituted with an ether group, an ester group, a carbonyl group, an acetal group, a nitrile group, a cyano group, a hydroxy group, a carboxyl group, or an aldehyde group, R is a $C_1$-$C_{10}$ alkyl group, a $C_1$-$C_{10}$ alkoxy group, a nitrogen atom, a sulfur atom, or an oxygen atom, and m is a positive integer of 0 to 2.

In this instance, a copolymer according to an exemplary embodiment of the invention may be a chemically amplified resist composition, and the PAG represented as Chemical formula 1 may be connected with a main chain of the copolymer.

Also, a chemically amplified resist composition according to an exemplary embodiment of the invention may include a copolymer and a solvent, and the PAG represented as Chemical formula 1 may be connected with a main chain of the copolymer.

According to another aspect of the present invention, there is provided a method of forming a pattern, the method including: coating on a substrate with the chemically amplified resist composition including the copolymer and the solvent, a main chain of the copolymer being connected with the PAG represented as Chemical formula 1, and drying the coated composition to form a resist layer; selectively exposing the resist layer; and developing the exposed resist layer.

Additional aspects, features, and/or advantages of the invention will be set forth in part in the description which follows and, in part, will be apparent from the description, or may be learned by practice of the invention.

BRIEF DESCRIPTION OF THE DRAWINGS

These and/or other aspects, features, and advantages of the invention will become apparent and more readily appreciated from the following description of exemplary embodiments, taken in conjunction with the accompanying drawings of which.

DETAILED DESCRIPTION

Figure 1:
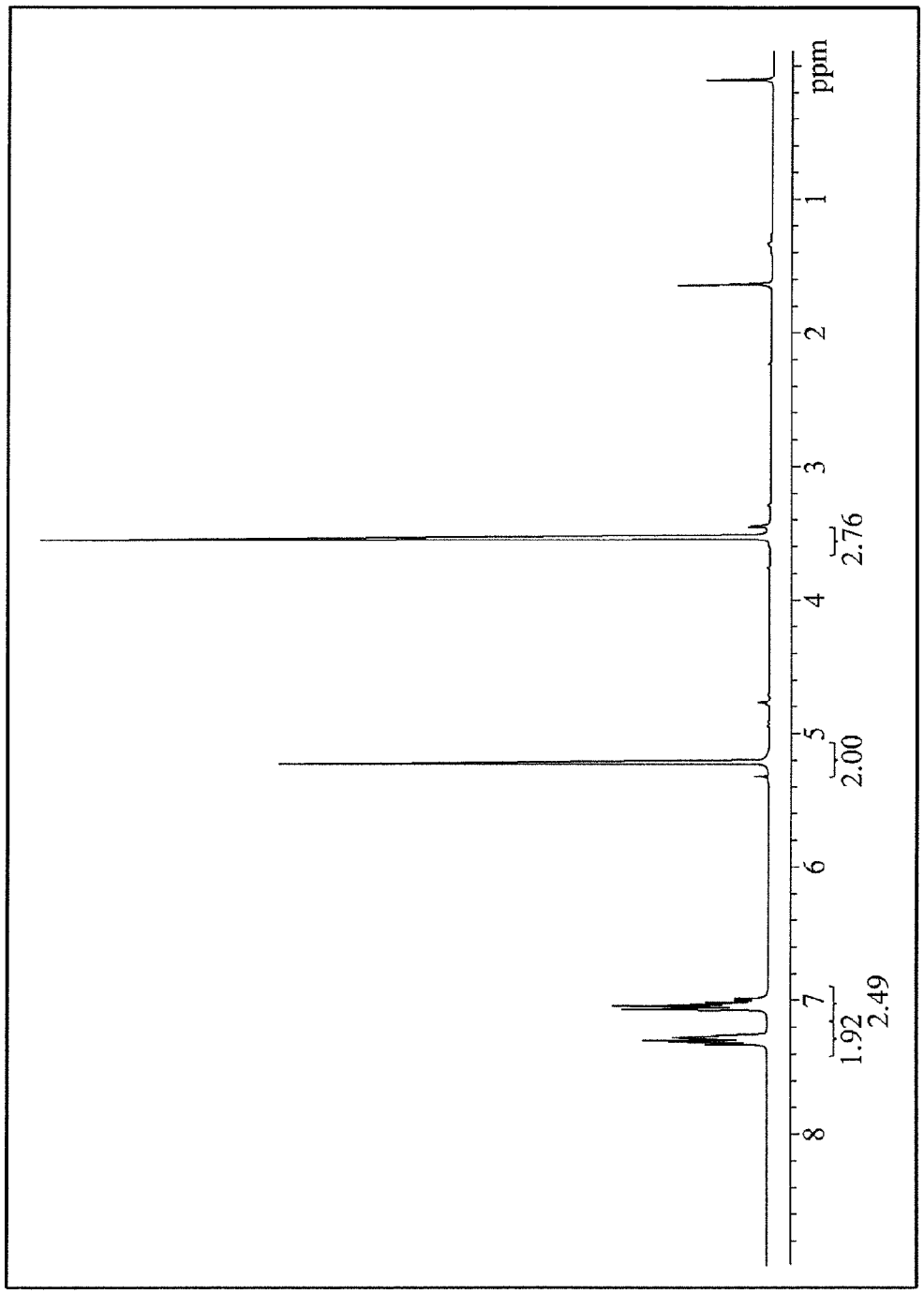
FIG. 1 illustrates a $^1$H-NMR spectrum of a compound obtained according to a synthesis example 1.

Reference will now be made in detail to exemplary embodiments of the present invention, examples of which are illustrated in the accompanying drawings, wherein like reference numerals refer to the like elements throughout. Exemplary embodiments are described below to explain the present invention by referring to the figures.

According to an exemplary embodiment of the invention, a photoacid generator (PAG), a copolymer including the PAG, a chemically amplified resist composition including the copolymer, and a method of forming a pattern using the chemically amplified resist composition will be herein described in detail.

The PAG according to the present exemplary embodiment may be represented as

[Chemical formula 1]

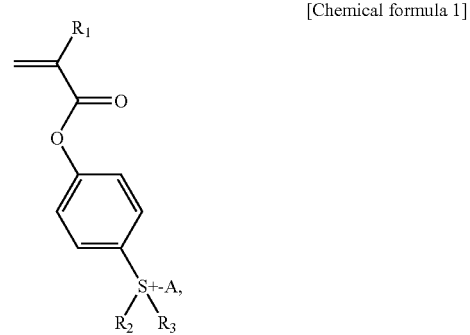

wherein $R_1$ is a hydrogen atom, a trifluoromethyl group, a $C_1$-$C_5$ alkyl group, or a $C_1$-$C_5$ alkoxy group, $R_2$ and $R_3$ are respectively a linear or branched $C_1$-$C_{20}$ alkyl group, an aryl group, a linear or branched $C_1$-$C_{20}$ perfluoroalkyl group, a benzyl group, or a $C_6$-$C_{20}$ aryl group, and $A^-$ is a compound represented as

[Chemical formula 2]

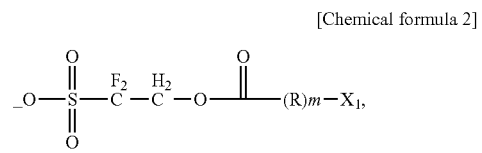

wherein $X_1$ is a monocyclic or polycyclic $C_3$-$C_{20}$ hydrocarbon group, a benzyl group, a $C_6$-$C_{20}$ aryl group, a $C_1$-$C_{10}$ alkyl group, a $C_1$-$C_{10}$ alkoxy group, a $C_1$-$C_{10}$ hydroxy alkyl group, or a cyano group, at least one hydrogen atom of the monocyclic or polycyclic $C_3$-$C_{20}$ hydrocarbon group is or is not substituted with an ether group, an ester group, a carbonyl group, an acetal group, a nitrile group, a cyano group, a hydroxy group, a carboxyl group, or an aldehyde group, R is a $C_1$-$C_{10}$ alkyl group, a $C_1$-$C_{10}$ alkoxy group, a nitrogen atom, a sulfur atom, or an oxygen atom, and m is a positive integer of 0 to 2.

The PAG according to an exemplary embodiment of the invention may be obtained through a synthesis reaction of a compound represented as Chemical formula 3 below and a salt represented as Chemical formula 4 below:

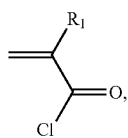

[Chemical formula 3]

wherein $R_1$ is a hydrogen atom, a trifluoromethyl group, a $C_1$-$C_5$ alkyl group, or $C_1$-$C_5$ alkoxy group.

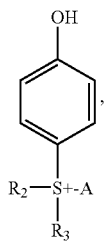

[Chemical formula 4]

wherein $R_2$ and $R_3$ are respectively a linear or branched $C_1$-$C_{20}$ alkyl group, an aryl group, a linear or branched $C_1$-$C_{20}$ perfluoroalkyl group, a benzyl group, or a $C_6$-$C_{20}$ aryl group, and $A^-$ is a compound represented as Chemical formula 2.

The salt represented as Chemical formula 2 may be, for example, obtained through a synthesis reaction between a salt represented as Chemical formula 5 below and a compound represented as Chemical formula 6 below, however, the present invention is not limited thereto, and thus various compounds and/or salts may be applicable. The synthesis reaction between the salt represented as Chemical formula 5 below and the compound represented as Chemical formula 6 below may be, for example, performed under a basic catalyst after reactants are dissolved in a reaction solvent at a temperature of about 0° C. to 100° C. Here, the reaction solvent is not particularly limited, however, for example, methylene chloride (MC), chloroform, dichloroethane, acetonitrile, toluene, and the like may be used alone or in a combination of two or more thereof as the reaction solvent. Also, the basic catalyst is not particularly limited, however, for example, triethylamine, diethylamine, pyridine, diethylisopropyl amine, N,N-dimethylaminopyridine may be used alone or in a combination of two or more thereof as the basic catalyst.

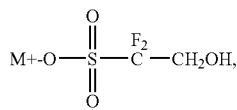

[Chemical formula 5]

wherein M is a lithium atom, a sodium atom, or a potassium atom.

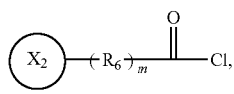

[Chemical formula 6]

wherein $X_2$ is a monocyclic or polycyclic $C_3$-$C_{20}$ hydrocarbon group, and at least one hydrogen atom of the monocyclic or polycyclic $C_3$-$C_{20}$ hydrocarbon group is or is not substituted with an ether group, an ester group, a carbonyl group, an acetal group, a nitrile group, a cyano group, a hydroxy group, a carboxyl group, or an aldehyde group, $R_6$ is a $C_1$-$C_{10}$ alkyl group, a $C_1$-$C_{10}$ alkoxy group, a nitrogen atom, a sulfur atom, or an oxygen atom, and m is a positive integer of 0 to 2.

In addition, the salt represented as Chemical formula 5 may be, for example, manufactured through a synthesis reaction using a salt represented as Chemical formula 7 below. First, the salt represented as Chemical formula 7 below is dissolved in a reaction solvent such as tetrahydrofuran, methanol, ethanol, propanol, and the like, and sodium borohydride (NaBH$_4$) is gradually dropped under an ice bath. Next, a reaction mixed liquid is stirred for about four hours under an oil bath of about 60° C., and is quenched with distilled water to remove the reaction solvent. Next, the reaction mixed liquid from which the reaction solvent is removed is dissolved with distilled water, and is acidified until a pH of the reaction mixed liquid becomes about 5 to 6 using a concentrated HCl. Next, the reaction mixed liquid is concentrated, methanol is added in the concentrated mixed liquid to form a slurry, and then the slurry is filtered. Next, a filtrate is cleansed using hexane, concentrated, crystallized using diethyl ether, and then filtered and dried to manufacture a salt represented as the above Chemical formula 5.

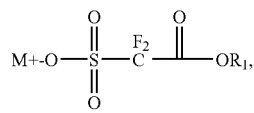

[Chemical formula 7]

wherein $R_1$ is a hydrogen atom, a methyl group, a trifluoromethyl group, a trichloromethyl group, a tribromomethyl group, or a triiodomethyl group, and M is a lithium atom, a sodium atom, or a potassium atom.

In addition, a main chain of the copolymer for the chemically amplified resist composition according to an exemplary embodiment may be connected with the PAG. The PAG may be connected with the main chain of the copolymer in a repeating unit type having the PAG, however, the present exemplary embodiment is not limited thereto. The copolymer may further include at least one of a repeating unit having an acid labile group, a repeating unit having a lactone ring, and a repeating unit having a hydroxy group, as necessary.

The copolymer according to an exemplary embodiment may be, for example, represented as

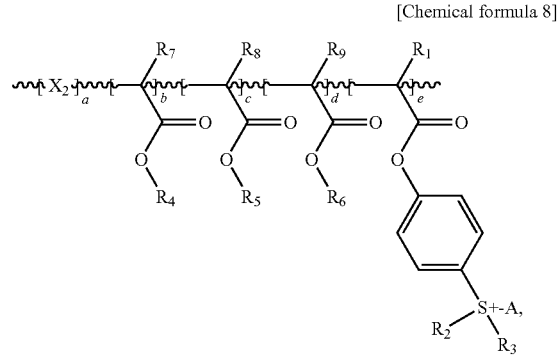

[Chemical formula 8]

wherein $R_1$ is a hydrogen atom, a trifluoromethyl group, a $C_1$-$C_5$ alkyl group, or $C_1$-$C_5$ alkoxy group, $R_2$ and $R_3$ are respectively a linear or branched $C_1$-$C_{20}$ alkyl group, an aryl group, a linear or branched $C_1$-$C_{20}$ perfluoroalkyl group, a benzyl group, or a $C_6$-$C_{20}$ aryl group, $R_4$, $R_5$ and $R_6$ are respectively a hydrogen atom, or a $C_1$-$C_{30}$ alkyl group including or not including an ether group, an ester group, a carbonyl group, an acetal group, an epoxy group, a nitrile group, or an aldehyde group, $R_7$, $R_8$ and $R_9$ are respectively a hydrogen atom, a methyl group, or a trifluoromethyl group, $X_2$ is olefin, vinyl, styrene, or a derivative thereof, a, b, c, d, and e respectively satisfy $0.01 \leq a/(a+b+c+d+e) < 0.4$; $0.01 < b/(a+b+c+d+e) < 0.3$; $0.01 < c/(a+b+c+d+e) < 0.3$; $0.01 \leq d/(a+b+c+d+e) < 0.3$; $0.01 \leq e/(a+b+c+d+e) < 0.15$, and $A^-$ is a compound represented as

[Chemical formula 2]

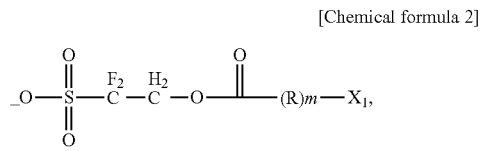

wherein $X_1$ is a monocyclic or polycyclic $C_3$-$C_{20}$ hydrocarbon group, a benzyl group, a $C_6$-$C_{20}$ aryl group, a $C_1$-$C_{10}$ alkyl group, a $C_1$-$C_{10}$ alkoxy group, a $C_1$-$C_{10}$ hydroxy alkyl group, or a cyano group, at least one hydrogen atom of the monocyclic or polycyclic $C_3$-$C_{20}$ hydrocarbon group is or is not substituted with an ether group, an ester group, a carbonyl group, an acetal group, a nitrile group, a cyano group, a hydroxy group, a carboxyl group, or an aldehyde group, R is a $C_1$-$C_{10}$ alkyl group, a $C_1$-$C_{10}$ alkoxy group, a nitrogen atom, a sulfur atom, or an oxygen atom, and m is a positive integer of 0 to 2.

The copolymer may be a block copolymer, a random copolymer, or a graft copolymer. The copolymer may be synthesized by a polymerization of monomers including the PAG, and a method of the polymerization is not particularly limited, however, for example, a radical polymerization may be used. As a polymerization initiator of the radical polymerization, azobisisobutyronitrile (AIBN), benzoyl peroxide (BPO), lauryl peroxide, azobisisocapronitrile, azobisisovaleronitrile, tert-butyl hydroperoxide, and the like may be used alone or in a combination of two or more thereof. A polymerization reaction may be performed by an arbitrary polymerization reaction selected from among bulk polymerization, solution polymerization, suspension polymerization, bulk-suspension polymerization, emulsion polymerization, and the like. As a polymerization solvent, at least one polymerization solvent selected from benzene, toluene, xylene, halogenated benzene, diethyl ether, tetrahydrofuran, 1,2-dichloroethane, esters, ethers, lactones, ketones, and amides may be used. Non-reaction monomer and by-products remaining in a reaction mixture may be preferably removed by a precipitation method performed by means of a solvent, after the polymerization is completed.

An amount of the PAG upon the polymerization of the copolymer may rely on an amount of a total solid of the chemically amplified resist composition including the copolymer. Specifically, the copolymer may perform the polymerization using the PAG of about 0.5 to 15 parts by weight with respect to about 100 parts by weight of the total solid of the chemically amplified resist composition. When the amount of the PAG is about 0.5 parts by weight or less with respect to about 100 parts by weight of the total solid of the composition, acid generation may be reduced to thereby reduce a resolution, and a resist pattern including a bottom layer may be not properly generated, that is, formed to be inclined, and when the amount of the PAG is about 15 parts by weight or more with respect to about 100 parts by weight of the same, the acid generation may overly occur to thereby increase in a thickness loss of an upper portion of the resist layer, and a light absorption of the PAG may increase to thereby reduce a transparence of a resin.

A weight-average molecular weight in terms of polystyrene measured by gel permeation chromatography (GPC) of the copolymer may be about 500 to 100,000. More specifically, the weight-average molecular weight may be about 3,000 to 30,000 considering coating property of the chemically amplified resist composition, developing property and heat resistance of the resist layer. When the weight-average molecular weight is about 500 or less, the resist pattern may be easily destroyed or deformed, and when the weight-average molecular weight exceeds about 100,000, the resolution of the resist pattern may be reduced. The molecular weight distribution of the copolymer may be about 0.9 to 5, and more particularly, about 1 to 3. The molecular weight distribution of the copolymer may be appropriately adjusted by changing a used amount and reaction time of a radical polymerization initiator.

As examples of the copolymer according to an exemplary embodiment of the invention, copolymers represented as Chemical formulas 9 to 21 may be given, and the present exemplary embodiments are not limited thereto.

[Chemical formula 9]

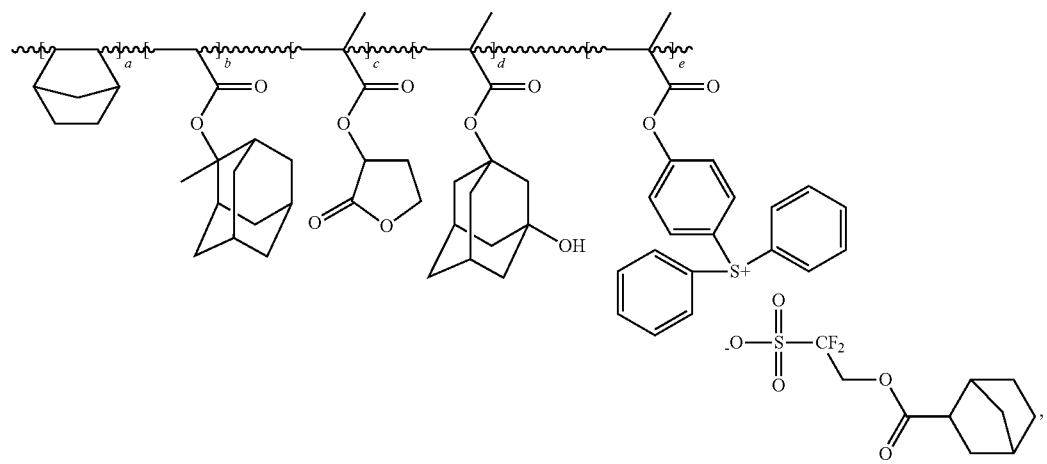

-continued
[Chemical formula 10]
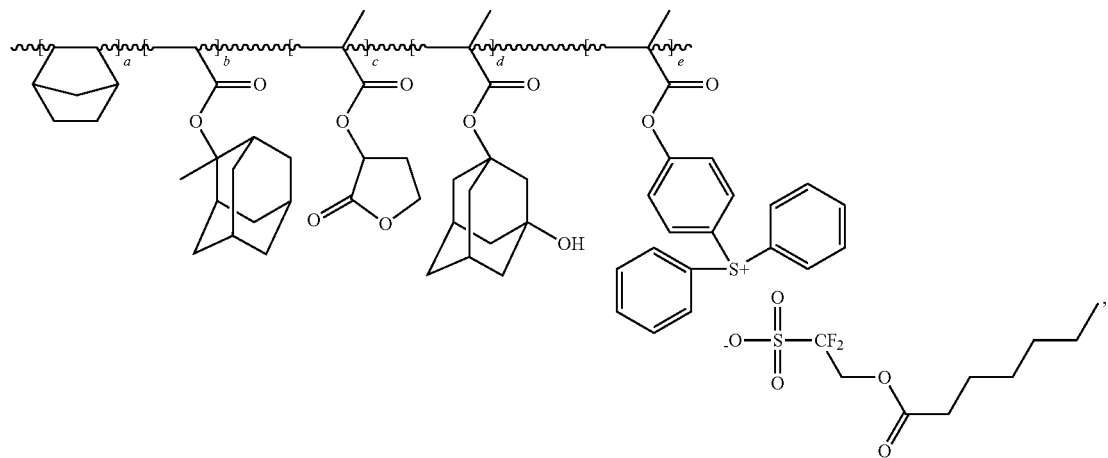
[Chemical formula 11]
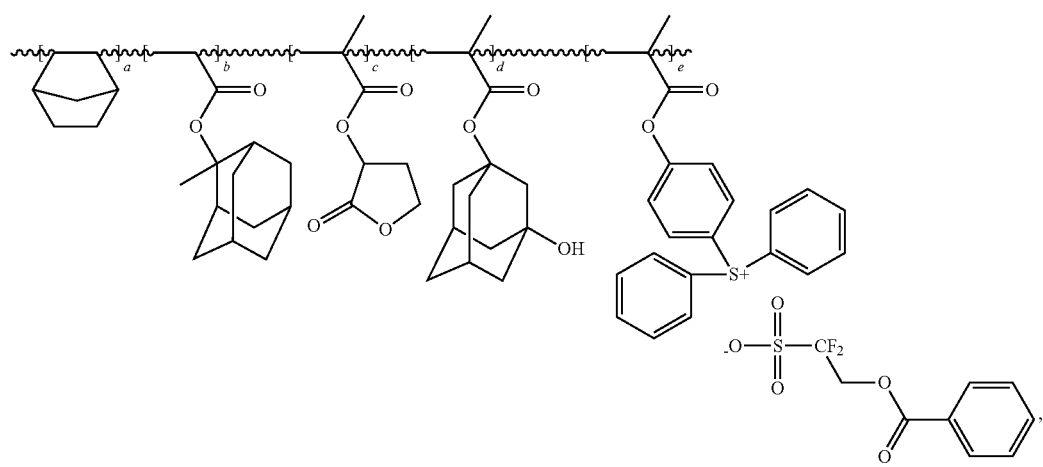
[Chemical formula 12]
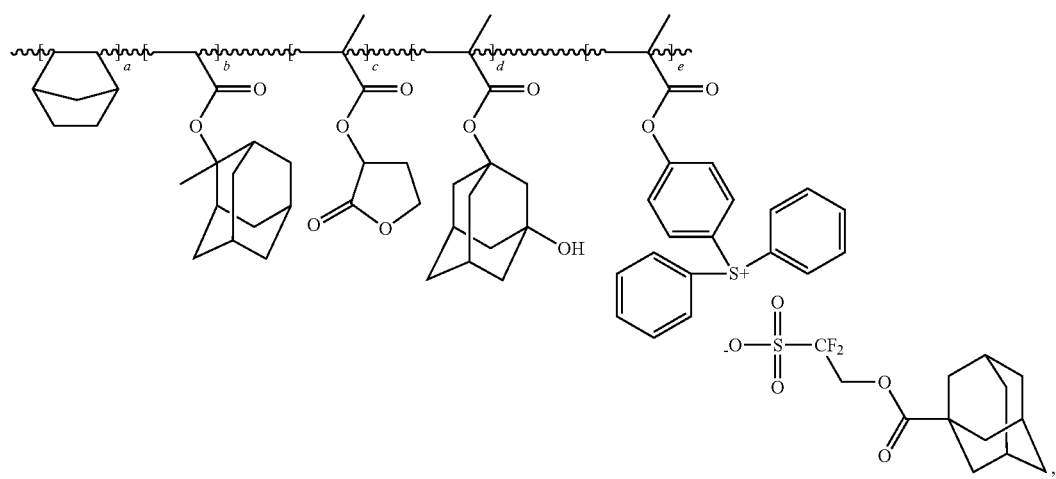

[Chemical formula 13]
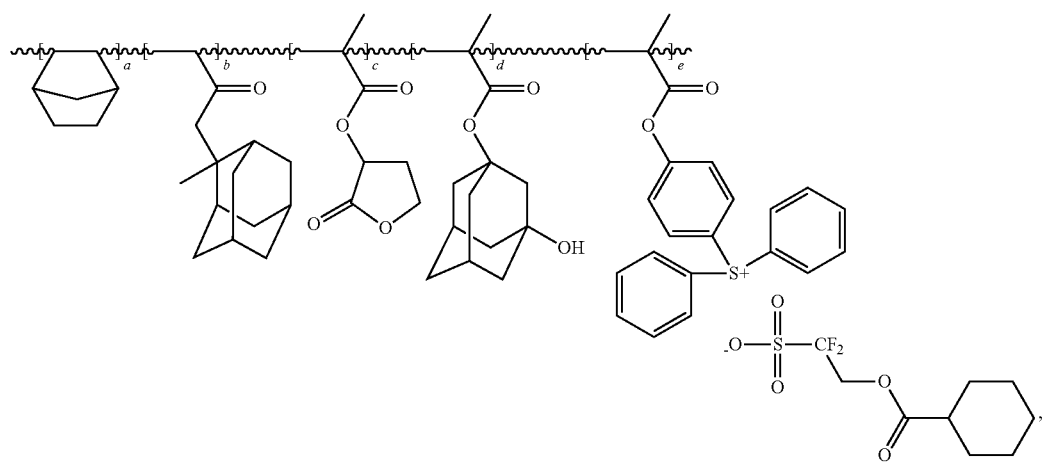
[Chemical formula 14]
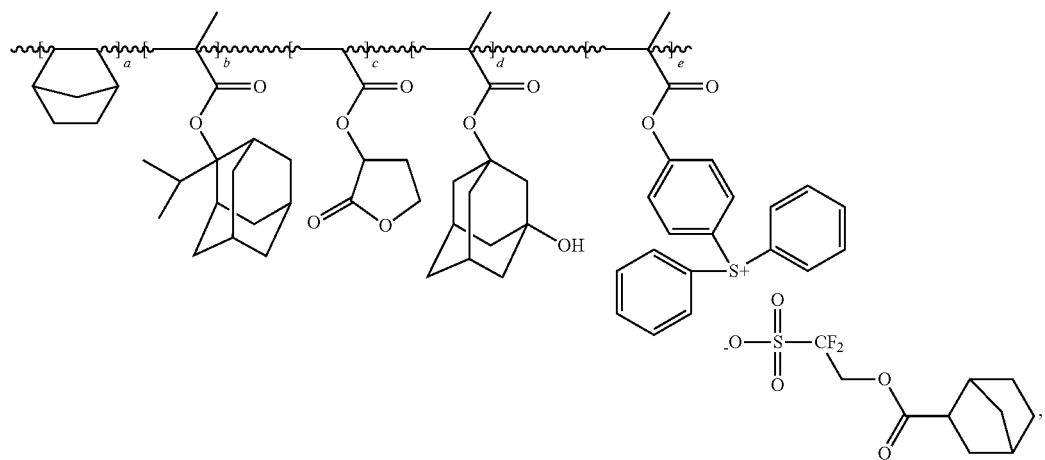
[Chemical formula 15]
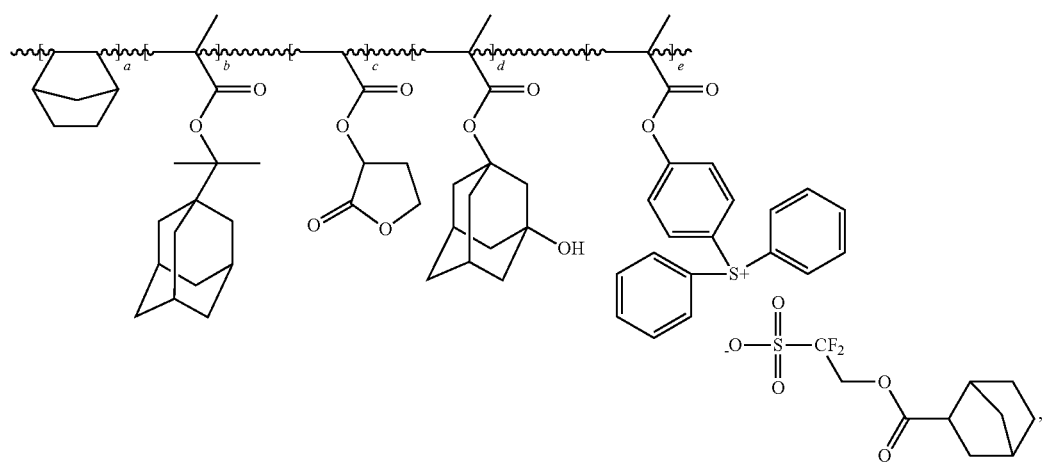

-continued
[Chemical formula 16]
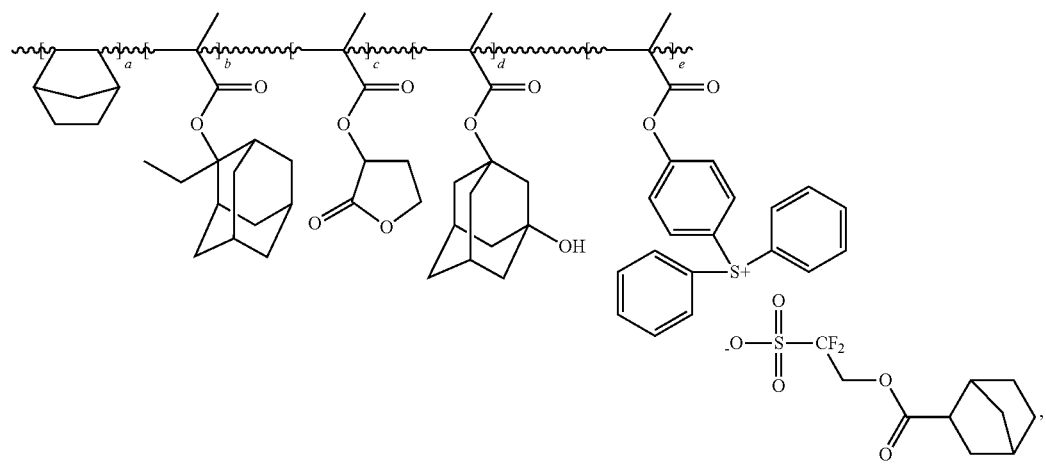
[Chemical formula 17]
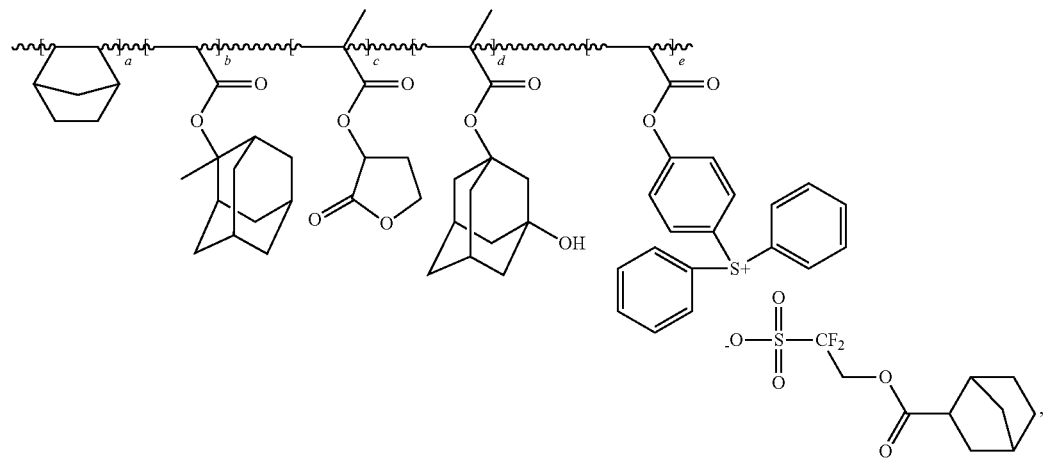
[Chemical formula 18]
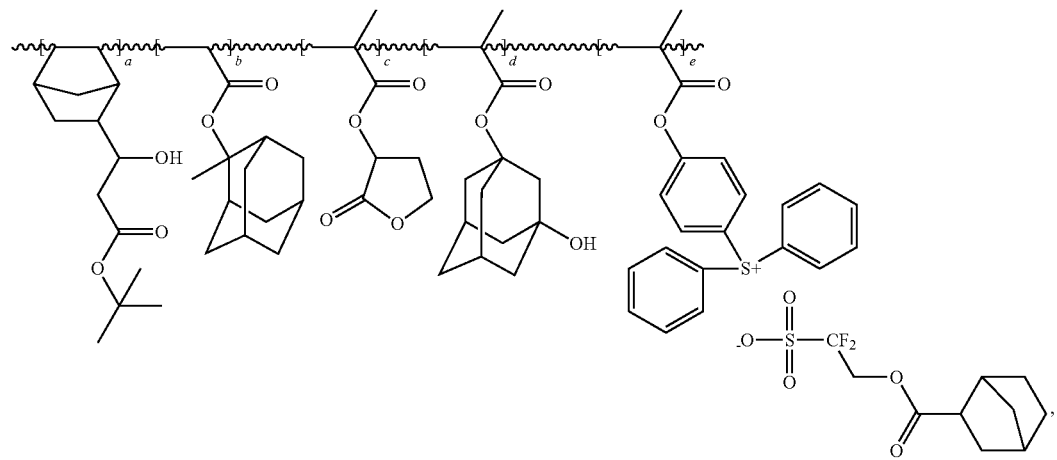

[Chemical formula 19]

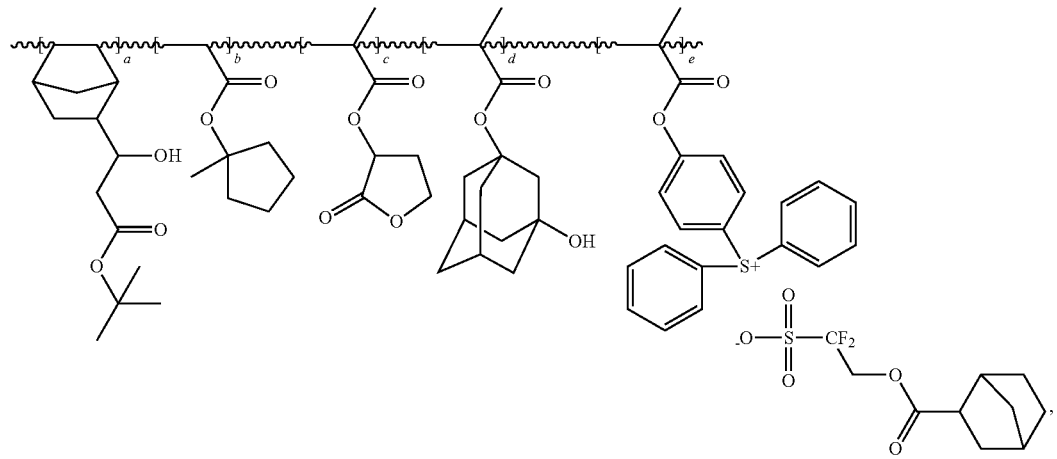

[Chemical formula 20]

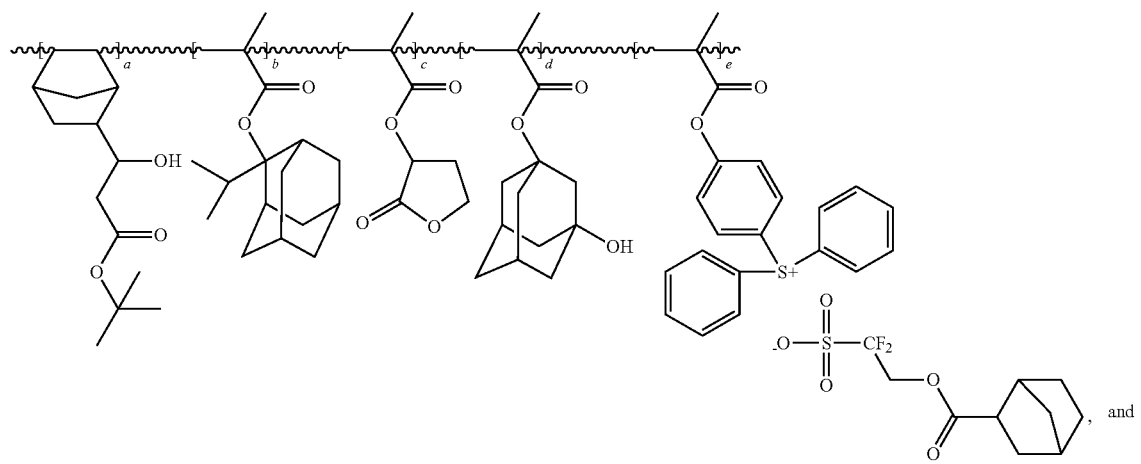
, and

[Chemical formula 21]

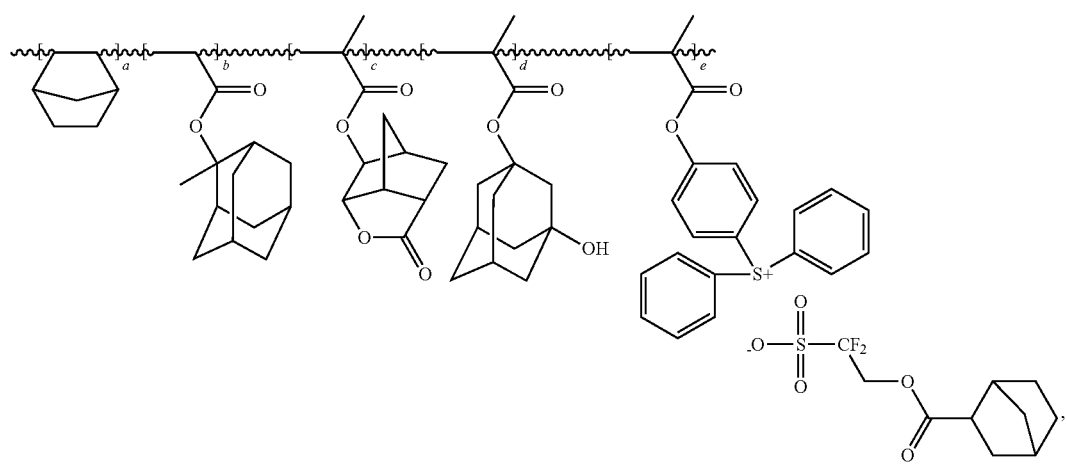
, wherein, a, b, c, d, and e may respectively satisfy $0.01 \leq a/(a+b+c+d+e)<0.4$; $0.01<b/(a+b+c+d+e)<0.3$; $0.01<c/(a+b+c+d+e)<0.3$; $0.01\leq d/(a+b+c+d+e)<0.3$; $0.01\leq e/(a+b+c+d+e)<0.15$.

In addition, the chemically amplified resist composition according to an exemplary embodiment of the invention may include the copolymer and a solvent, and a main chain of the copolymer is connected with the PAG. The chemically amplified resist composition according to an exemplary embodiment of the invention may further include other additives. The other additives are not particularly limited, however, for example, a surfactant and water-soluble alcohols may be used alone or in any combination thereof. The chemically amplified resist composition according to an exemplary embodiment of the invention may further include a separate PAG.

An amount of the copolymer may be about 3 wt. % to 20 wt. % with respect to the total amount of the chemically amplified resist composition. When the amount of the copolymer is less than about 3 wt. %, a thickness of the resist layer may be significantly reduced to encounter a difficulty in obtaining a desired resist pattern thickness, and when the amount of the copolymer exceeds about 20 wt. %, the thickness of the resist layer may significantly increase.

The solvent included in the chemically amplified resist composition may be not particularly limited as long as the solvent is able to dissolve a solid of the composition, and having an appropriate drying speed, however, for example, glycol ether esters such as ethyl cellosolve acetate, methyl cellosolve acetate, and propylene glycol methyl ether acetate; esters such as ethyl lactate, butyl acetate, amyl acetate, and ethyl pyruvate; ketones such as acetone, methyl isobutyl ketone, 2-heptanone, and cyclohexanone; and cyclic ester such as γ-butyrolactone, and the like may be used alone or in a combination of two or more thereof.

In addition, a method of forming a pattern according to an exemplary embodiment of the invention may use the chemically amplified resist composition to form a resist pattern on a substrate, however the present exemplary embodiment is not limited thereto. For example, the method of the present exemplary embodiment may include forming a pattern of a semiconductor device and/or display device using the resist pattern, that is, a transistor, a capacitor, and metal wiring. The method of forming the pattern according to an exemplary embodiment may include coating on a substrate with the chemically amplified resist composition, drying the coated composition to form a resist layer, selectively exposing the resist layer, and developing the exposed resist layer. The method according to the present exemplary embodiment may be hereinafter described in detail.

First, the chemically amplified resist composition may be coated on the substrate prepared in advance. The substrate is not particularly limited, however, an arbitrary substrate selected from a silicon wafer, a glass substrate, a flexible substrate, and the like may be used. The coating method is arbitrarily selected from spin coating, dipping, spraying, transfering.

Next, a light may be irradiated to the chemically amplified resist composition coated on the substrate, or a heat may be applied thereto. As a result, a solvent of the composition may be evaporated to form the resist layer. In this instance, hardening of the resist layer may be slightly performed.

Next, the resist layer may be selectively exposed. Here, selectively exposing the resist layer may denote exposing the resist layer so as to obtain a desired resist pattern. For example, a mask for forming the desired resist pattern may be used upon selectively exposing. A light source upon the selectively exposing may be any light source arbitrarily selected form a KrF excimer laser, an ArF excimer laser, an Extreme Ultra Violet (EUV) light, an X-ray, and an electron-beam (e-beam). A light wavelength of the light source upon the exposing may be arbitrarily selected from about 180 nm to 250 nm, as necessary. The exposed resist layer may be hardened after the exposing, as necessary.

Next, the exposed resist layer may be developed using a developing solution. As a result, the resist pattern may be formed. As the developing solution, sodium hydroxide, potassium hydroxide, sodium carbonate, sodium silicate, sodium metasilicate, ammonia water, ethylamin, n-propylamine, triethylamine, tetramethylammonium hydroxide, tetraethylammonium hydroxide, and the like may be used alone or in a combination of two or more thereof. From among these, an aqueous solution including the tetramethylammonium hydroxide may be used.

According to an exemplary embodiment, the PAG may be connected with a main chain of the copolymer, thereby enabling the PAG to be equally dispersed within the resist layer. In this regard, characteristics of line edge roughness and etch resistance of the resist pattern may be improved. In addition, the resist layer may have a high sensitivity, a high thermal stability, a high adhesive strength with respect to the substrate, a high transparence with respect to an exposure light, and the resist pattern may have a high resolution.

Hereinafter, the present invention will be described in detail by examples. It is to be understood, however, that these examples are for illustrative purpose only, and are not construed to limit the scope of the present invention.

SYNTHESIS EXAMPLES

Synthesis Example 1

Methoxymethoxybenzene Synthesis

Under an ice bath, about 200 g of phenol and about 256 g of chloromethyl methyl ether were mixed and stirred in about 2 L of methylene chloride (MC), and about 740 ml of diisopropylethylamine (DIPEA) was gradually dropped. Next, the ice bath was removed and a temperature was increased, and then a synthesis reaction (see Equation 1 below) was performed while stirring for about 12 hours at room temperature. Next, distilled water was added in a reaction mixed liquid to complete the synthesis reaction and to extract an organic phase. Next, the organic phase was washed using about 0.5 N of HCl aqueous solution, distilled water, about 1 N of NaOH aqueous solution, and distilled water in the stated order, and then dried using magnesium sulphate. Next, the organic phase was filtered and concentrated to obtain about 240 g (a yield: about 81.7%) of methoxymethoxybenzene, and a structure of the methoxymethoxybenzene was observed by $^1$H-NMR (see FIG. 1):

$^1$H-NMR (DMSO, reference: tetramethylsilane): (ppm) 3.48 (s, 3H), 5.17 (s, 2H), 7.03 (m, 3H), 7.28 (m, 2H),

[Equation 1]

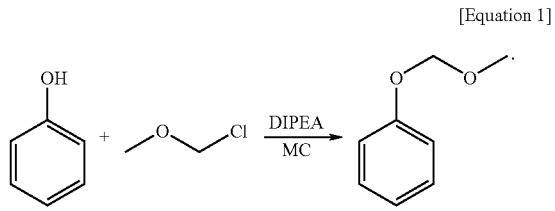

Synthesis Example 2

Figure 2:
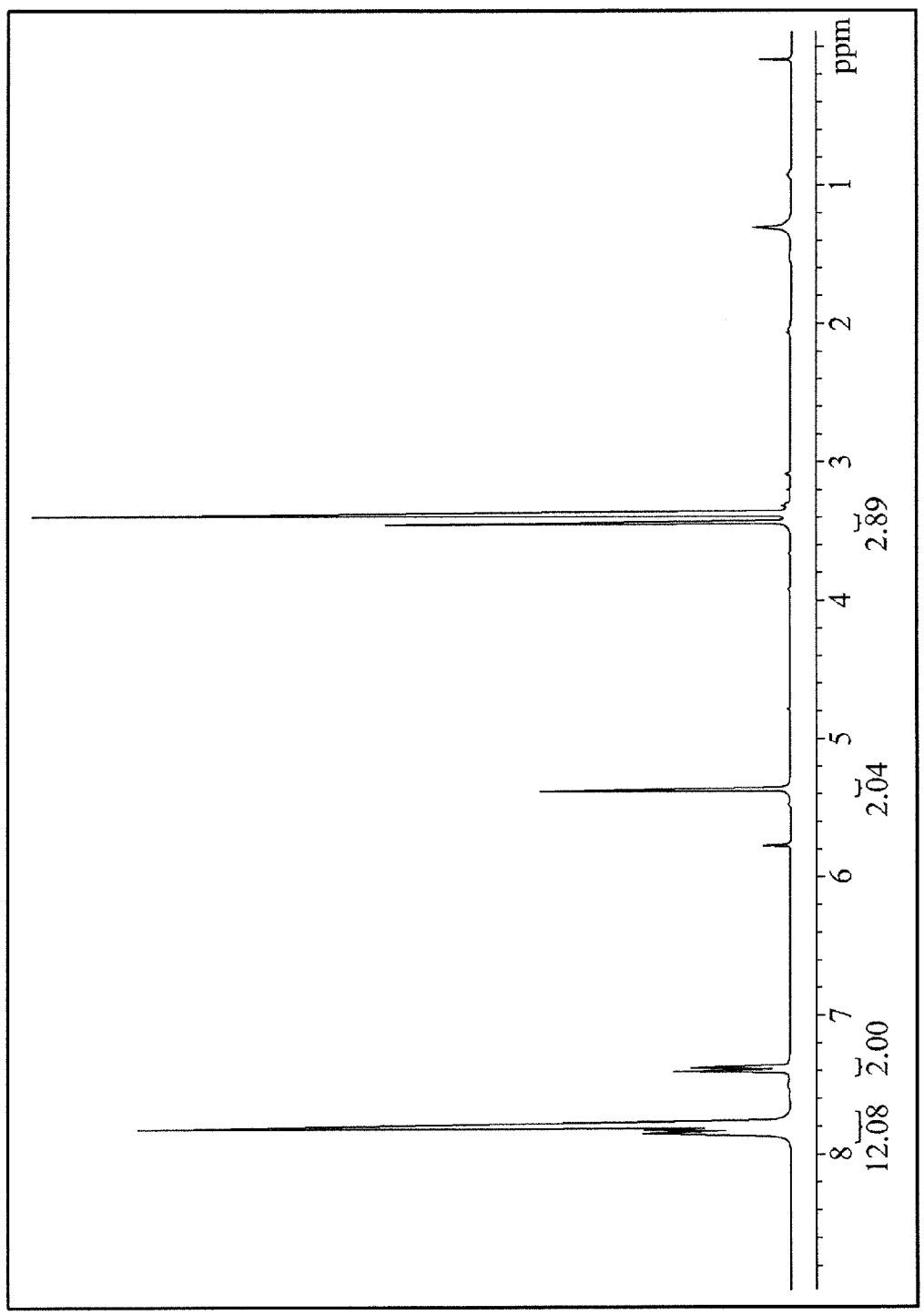
FIG. 2 illustrates a $^1$H-NMR spectrum of a salt obtained according to a synthesis example 2.
Figure 3:
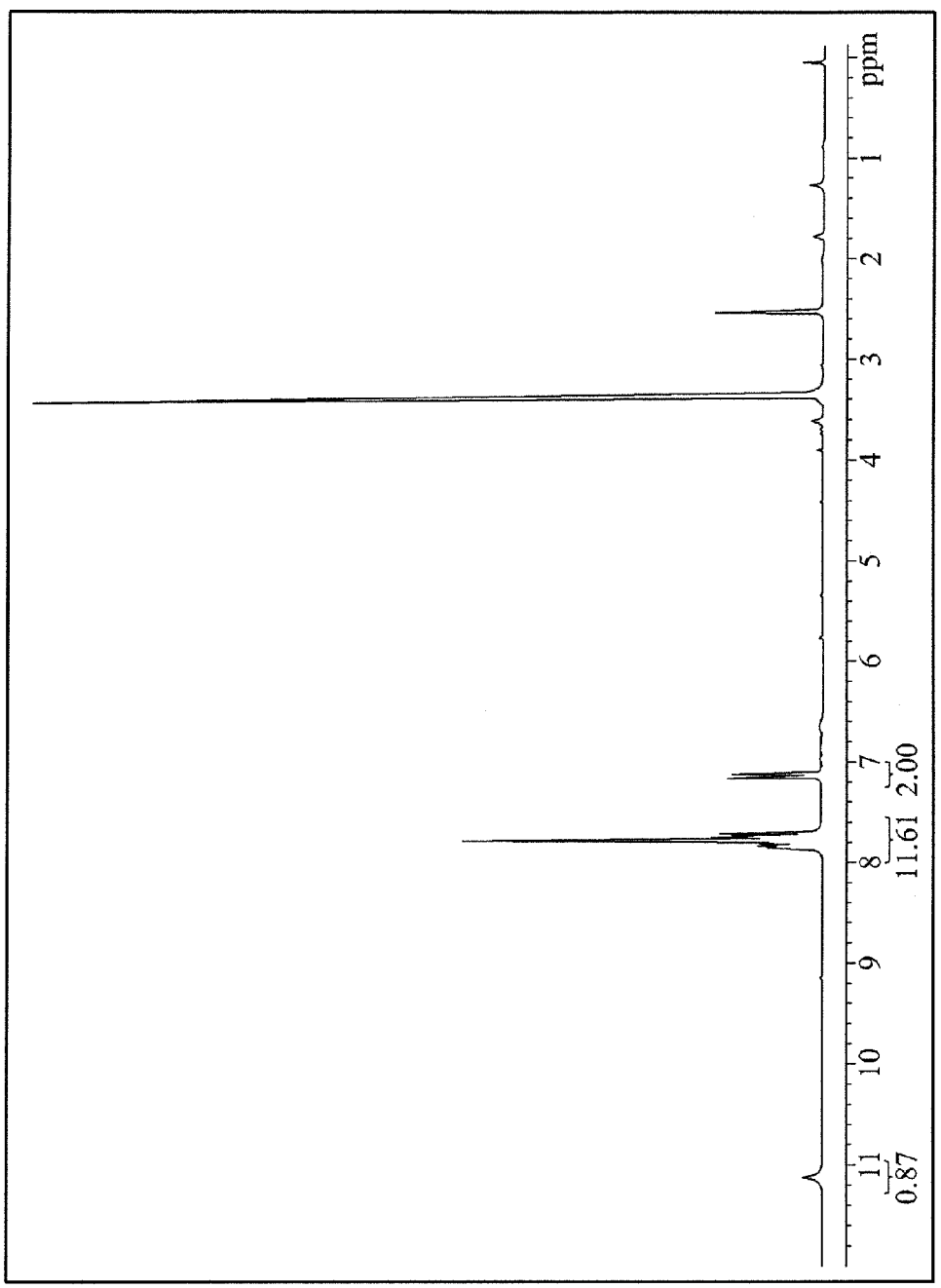
FIG. 3 illustrates a $^1$H-NMR spectrum of a salt obtained according to a synthesis example 3.
Figure 4:
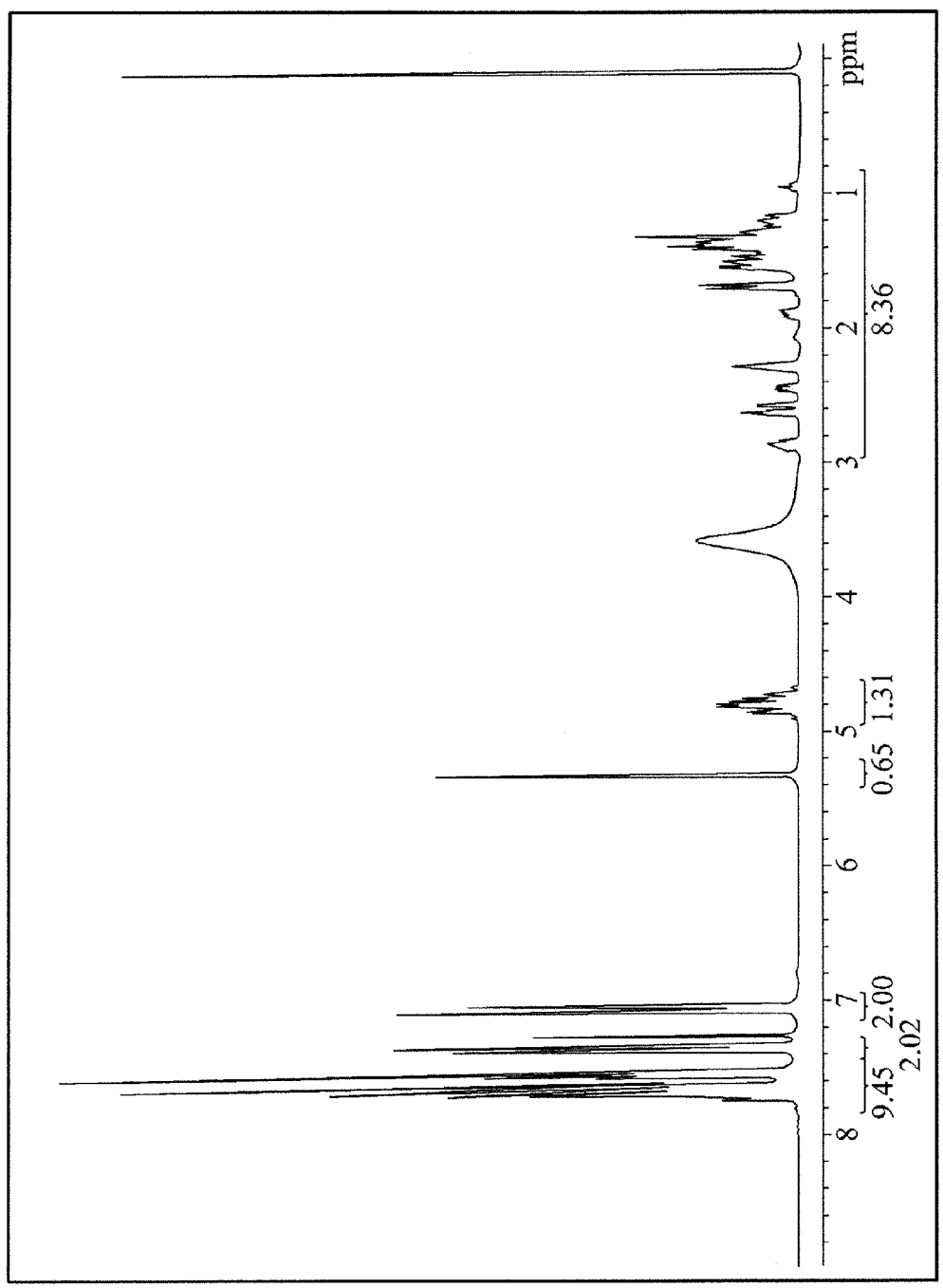
FIG. 4 illustrates a $^1$H-NMR spectrum of a salt obtained according to a synthesis example 4.
Figure 5:
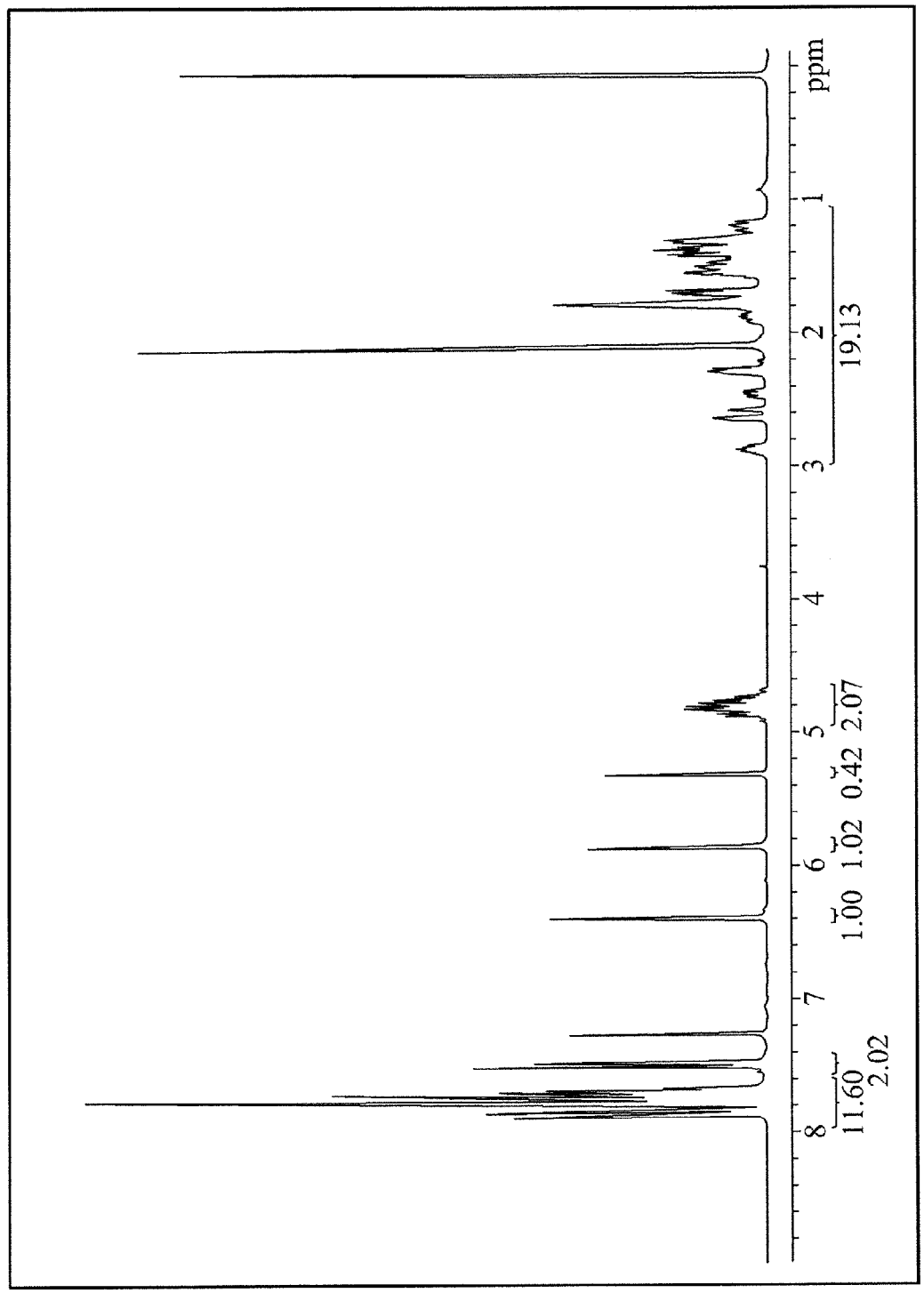
FIG. 5 illustrates a $^1$H-NMR spectrum of a salt obtained according to a synthesis example 5.

Diphenyl-4-methoxymethoxyphenylsulfonium Trifluoromethanesulfonate Salt Synthesis About 100 g of the methoxymethoxybenzene manufactured in the synthesis example 1 and about 133.1 g of phenyl sulfoxide were mixed and stirred in about 1,200 ml of an MC, and then a temperature was reduced to about −78° C. using a dry ice-aceton. Next, about 240 g of trifluoromethanesulfonic anhydride was gradually dropped and stirred for about three hours using a dropping funnel at about −78° C. to perform a synthesis reaction (See Equation 2 below). Next, the synthesis reaction was terminated when an initiator on a thin layer chromatography (TLC) disappeared. Next, about 200 g of calcium carbonate was dissolved in about 1.5 L of water, and the reaction mixed liquid was added in a solvent cooled to about 0° C. and strongly stirred for about 20 minutes. Next, an organic phase was extracted, and further stirred in a calcium carbonate aqueous solution. Next, the extracted organic phase was washed using brine, and dried using magnesium sulphate. Next, the organic was filtered and concentrated to obtain about 200 g (a yield: about 58.5%) of a diphenyl-4-methoxymethoxyphenylsulfonium trifluoromethanesulfonate salt, and a structure of the diphenyl-4-methoxymethoxyphenylsulfonium trifluoromethanesulfonate salt was observed by $^1$H-NMR (See FIG. 2):

$^1$H-NMR (CDCl$_3$, reference: tetramethylsilane): (ppm) 5.34 (s, 2H), 7.38 (d, 2H), 7.77-7.84 (m, 2H), the diphenyl-4-hydroxyphenylsulfonium trifluoromethanesulfonate salt was observed by $^1$H-NMR (see FIG. 3):

$^1$H-NMR (CDCl$_3$, reference: tetramethylsilane): (ppm) 7.12 (d, 2H), 7.69-7.83 (m, 12H), 11.12(br, 1H),

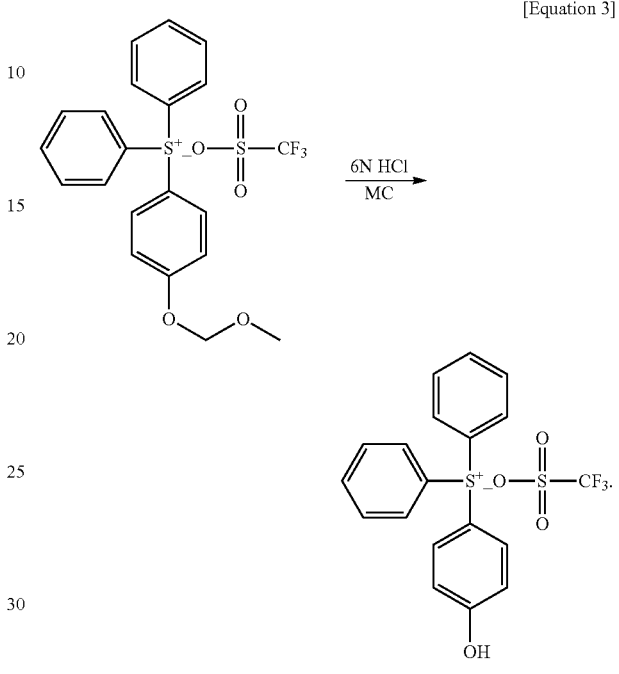

[Equation 3]

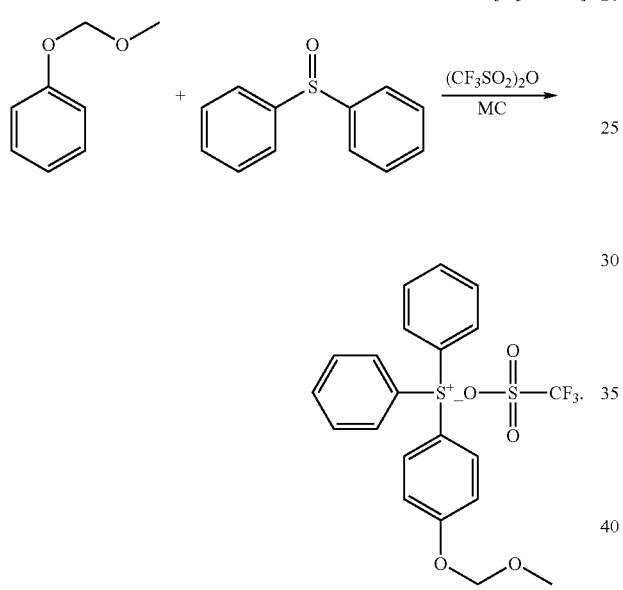

[Equation 2]

Synthesis Example 3

Diphenyl-4-hydroxyphenylsulfonium Trifluoromethanesulfonate Salt Synthesis

About 100 g of diphenyl-4-methoxymethoxyphenylsulfonium trifluoromethanesulfonate salt manufactured in the synthesis example 2 was mixed and stirred in about 300 ml of the MC, and about 548 ml of 6 N HCl aqueous solution was dropped and stirred at about 50° C. to perform a synthesis reaction (see Equation 3). Next, the synthesis reaction was terminated when the initiator on the TLC disappeared, and then the MC was added, and separation of phases was performed. Next, an organic phase was extracted, washed twice using brine, and dried using magnesium sulphate. Next, the organic phase was filtered and concentrated to obtain about 100 g (a yield: about 71%) of a diphenyl-4-hydroxyphenylsulfonium trifluoromethanesulfonate salt, and a structure of Synthesis Example 4

Bicyclo[2.2.1]heptane-2-carboxylic acid-2,2-difluoro-2-sulfo-ethyl Ester Diphenyl-4-hydroxyphenylsulfonium Salt Synthesis About 10 g of the diphenyl-4-hydroxyphenylsulfonium trifluoromethanesulfonate salt manufactured in the synthesis example 3 and about 10 g of a bicyclo[2.2.1]heptane-2-carboxylic acid-2,2-difluoro-2-sulfo-ethyl ester sodium salt were dissolved in about 100 ml of MC and about 100 ml of water, and a synthesis reaction (see Equation 4 below) was performed while stirring for about three hours. In this instance, a process of the synthesis reaction was observed by $^{19}$F NMR using a small amount of an extracted organic phase. The organic phase was extracted when the synthesis reaction was terminated, a solvent was removed, and the organic phase was washed using an MC of a soluble solvent and hexane of a sparingly soluble solvent. Next, the solvents were removed, and drying under a reduced pressure was performed to obtain about 9.42 g of a bicyclo[2.2.1]heptane-2-carboxylic acid-2, 2-difluoro-2-sulfo-ethyl ester diphenyl-4-hydroxyphenylsulfonium salt, and a structure of the bicyclo[2.2.1]heptane-2-carboxylic acid-2,2-difluoro-2-sulfo-ethyl ester diphenyl-4-hydroxyphenylsulfonium salt was observed by $^1$H-NMR:

$^1$H-NMR (chloroform-d3, reference: tetramethylsilane): (ppm) 1.13-2.85 (m, 11H), 4.78 (m, 2H), 7.05 (d, 2H), 7.38 (d, 2H), 7.55-7.78 (m, 10H),

[Equation 4]

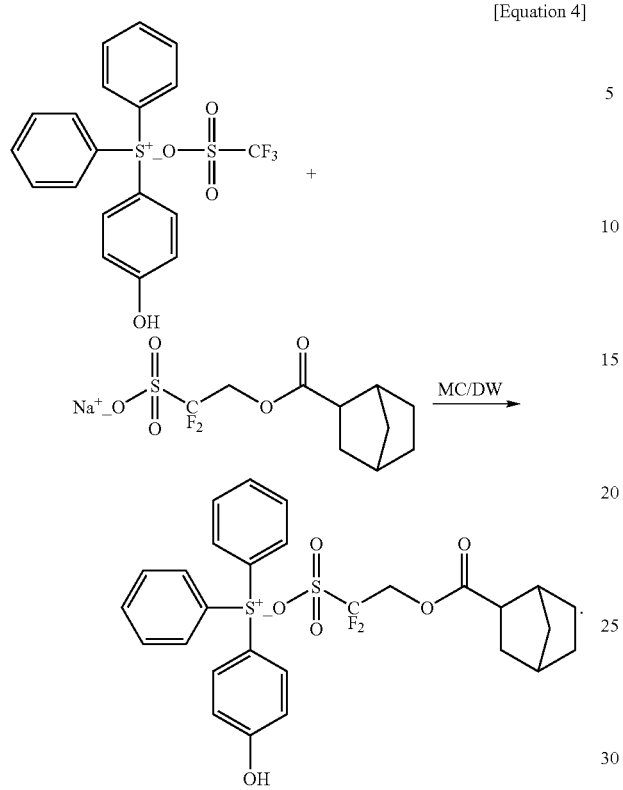

Synthesis Example 5

Bicyclo[2.2.1]heptane-2-carboxylic acid-2,2-difluoro-2-sulfo-ethyl Ester Diphenyl-4-methacroyloxy-phenylsulfonium Salt Synthesis About 9.42 g of the bicyclo[2.2.1]heptane-2-carboxylic acid-2,2-difluoro-2-sulfo-ethyl ester diphenyl-4-hydroxyphenylsulfonium salt synthesis, about 1.72 ml of methacryloyl chloride, and about 20 mg of 4-methoxyphenol (MEHQ) acting as a polymerization inhibitor were mixed and stirred in about 150 ml of the MC, about 4.37 ml of diisopropylethylamine (DIPEA) was gradually dropped using a dropping funnel under an ice bath, and a synthesis reaction (see Equation 5 below) was performed while stirring for about three hours at room temperature. In this instance, 4-dimethylaminopyridine (DMAP) was used as a reaction catalyst, and a process of the synthesis reaction was observed by $^{19}$F NMR using a small amount of an extracted organic phase. The organic phase was extracted when the synthesis reaction was terminated, and washed using 1N HCl, distilled water, a saturated sodium bicarbonate aqueous solution, and distilled water in the stated order (three times). Next, a solvent was removed, and the organic phase washed using the MC of a soluble solvent and hexane of a sparingly soluble solvent. Next, the solvents were removed, and drying under a reduced pressure was performed to obtain about 7.4 g (a yield: 70.1%) of a bicyclo[2.2.1]heptane-2-carboxylic acid-2,2-difluoro-2-sulfo-ethyl ester diphenyl-4-methacroyloxy-phenylsulfonium salt, and a structure of the bicyclo[2.2.1]heptane-2-carboxylic acid-2,2-difluoro-2-sulfo-ethyl ester diphenyl-4-methacroyloxy-phenylsulfonium salt was observed by $^1$H-NMR:

$^1$H-NMR (chloroform-d3, reference: tetramethylsilane): (ppm) 1.12-2.83 (m, 14H), 4.78 (m, 2H), 5.85 (s, 1H), 6.39 (s, 1H), 7.48 (d, 2H), 7.67-7.76 (m, 10H), 7.86 (d, 2H),

[Equation 5]

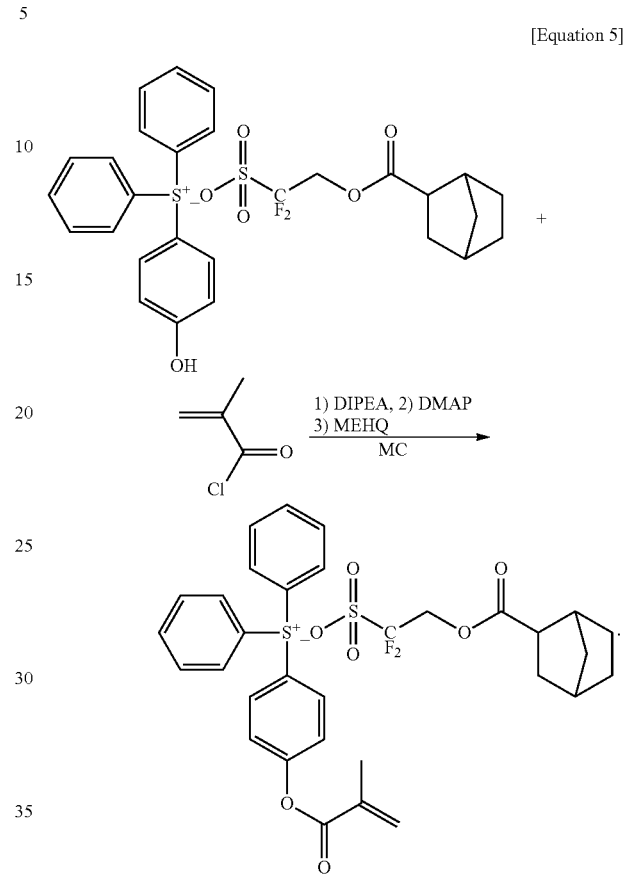

Synthesis Example 6

Bicyclo[2.2.1]heptane-2-carboxylic acid-2,2-difluoro-2-sulfo-ethyl Ester Diphenyl-4-acroyloxy-phenylsulfonium Salt Synthesis About 8.2 g of the bicyclo[2.2.1]heptane-2-carboxylic acid-2,2-difluoro-2-sulfo-ethyl ester diphenyl-4-hydroxyphenylsulfonium salt manufactured in the synthesis example 4, about 1.21 ml of acryloyl chloride, and about 15 mg of 4-methoxyphenol (MEHQ) were mixed and stirred in about 150 ml of an MC, about 4.24 ml of diisopropylethylamine (DIPEA) was gradually dropped using a dropping funnel under an ice bath, and a synthesis reaction (see Equation 6 below) was performed while stirring for about three hours at room temperature. In this instance, 4-dimethylaminopyridine (DMAP) was used as a reaction catalyst, and a process of the synthesis reaction was observed by $^{19}$F NMR using a small amount of an extracted organic phase. The organic phase was extracted when the synthesis reaction was terminated, and washed using 1N HCl, distilled water, a saturated sodium bicarbonate aqueous solution, and distilled water in the stated order (three times). Next, a solvent was removed, and washing with the MC of a soluble solvent and hexane of a sparingly soluble solvent was performed.

Figure 6:
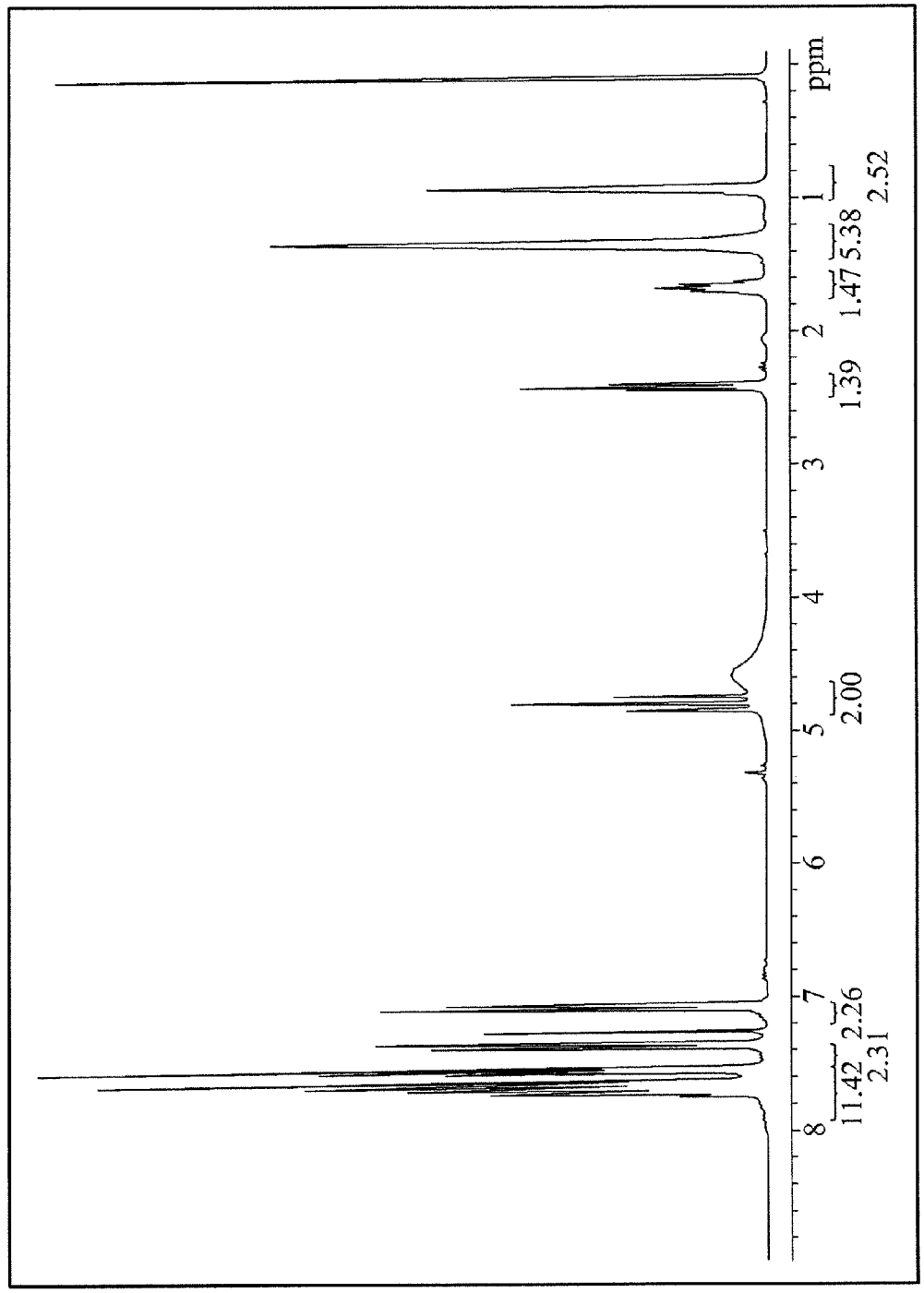
FIG. 6 illustrates a $^1$H-NMR spectrum of a salt obtained according to a synthesis example 7.

Next, the solvents were removed, and drying under a reduced pressure was performed to obtain about 6.4 g (a yield: 68%) of a bicyclo[2.2.1]heptane-2-carboxylic acid-2,2-difluoro-2-sulfo-ethyl ester diphenyl-4-acroyloxy-phenyl-sulfonium salt, and a structure of the bicyclo[2.2.1]heptane-2-carboxylic acid-2,2-difluoro-2-sulfo-ethyl ester diphenyl-4-acroyloxy-phenylsulfonium salt was observed by $^1$H-NMR:

$^1$H-NMR (chloroform-d3, reference: tetramethylsilane): (ppm) 1.21-2.79 (m, 14H), 4.54 (m, 2H), 6.21 (d, 1H), 6.39 (t, 1H), 6.87 (d, 1H) 7.45 (d, 2H), 7.65-7.76 (m, 10H), 7.86 (d, 2H), difluoro-2-sulfo-ethyl ester diphenyl-4-hydroxyphenylsulfonium salt was observed by $^1$H-NMR (see FIG. 6):

$^1$H-NMR (chloroform-d3, reference: tetramethylsilane): (ppm) 0.83 (t, 3H), 1.32 (m, 6H), 1.61 (m, 2H), 1.38 (t, 2H), 4.78 (t, 2H), 7.05 (d, 2H), 7.35 (d, 2H), 7.55-7.78 (m, 10H),

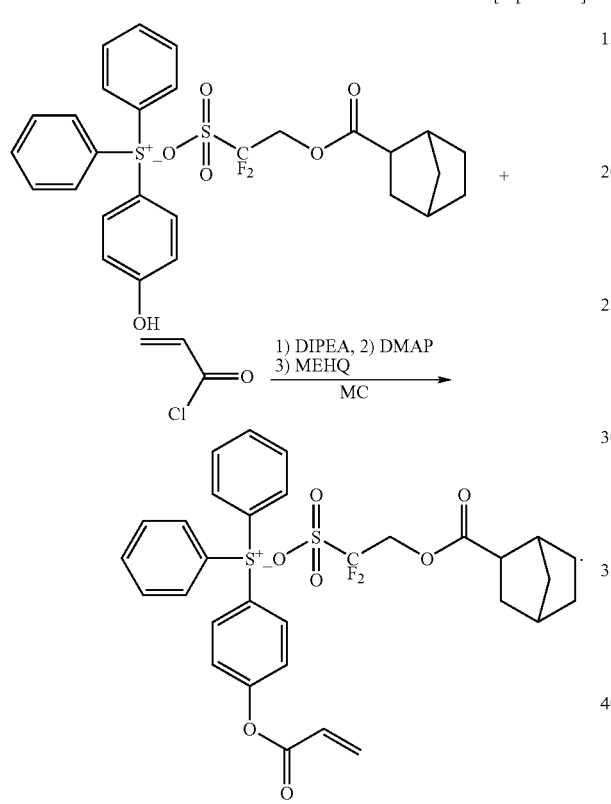

[Equation 6]

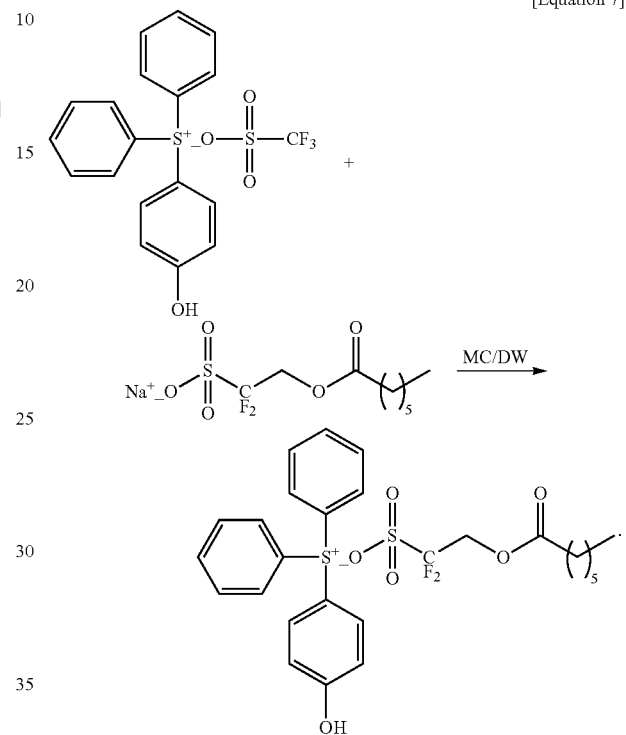

[Equation 7]

Synthesis Example 7

Heptanoic acid-2,2-difluoro-2-sulfo-ethyl Ester Diphenyl-4-hydroxyphenylsulfonium Salt Synthesis About 7 g of the diphenyl-4-hydroxyphenylsulfonium tri-fluoromethanesulfonate salt and about 5.81 g of a heptanoic acid-2,2-difluoro-2-sulfo-ethyl ester sodium salt were dissolved in about 100 ml of an MC and about 100 ml of water, and a synthesis reaction (see Equation 7 below) was performed while strongly stirring for three hours. In this instance, a process of the synthesis reaction was observed by $^{19}$F NMR using a small amount of an extracted organic phase.

The organic phase was extracted when the synthesis reaction was terminated, and a solvent was removed. Next, washing with the MC of a soluble solvent and hexane of a sparingly soluble solvent was performed. Next, the solvents were removed, and drying under a reduced pressure was performed to obtain about 8.87 g (a yield: 98.5%) of a heptanoic acid-2,2-difluoro-2-sulfo-ethyl ester diphenyl-4-hydroxyphenyl-sulfonium salt, and a structure of the heptanoic acid-2,2-

Synthesis Example 8

Heptanoic acid-2,2-difluoro-2-sulfo-ethyl Ester Diphenyl-4-methacroyloxy-phenylsulfonium Salt Synthesis About 8.87 g of the heptanoic acid-2,2-difluoro-2-sulfo-ethyl ester diphenyl-4-hydroxyphenylsulfonium salt manufactured in the synthesis example 7, about 1.5 ml of methacryloyl chloride, and about 17.4 mg of 4-methoxyphenol (MEHQ) were mixed and stirred in about 150 ml of an MC, about 3.71 ml of diisopropylethylamine (DIPEA) was gradually dropped using a dropping funnel under an ice bath, and a synthesis reaction (see Equation 8 below) was performed while stirring for about three hours at room temperature. In this instance, 4-dimethylaminopyridine (DMAP) was used as a reaction catalyst, and a process of the synthesis reaction was observed by $^{19}$F NMR using a small amount of an extracted organic phase. The organic phase was extracted when the synthesis reaction was terminated, and washed using 1N HCl, distilled water, a saturated sodium bicarbonate aqueous solution, and distilled water in the stated order (three times). Next, a solvent was removed, and washing with the MC of a soluble solvent and hexane of a sparingly soluble solvent was performed.

Figure 7:
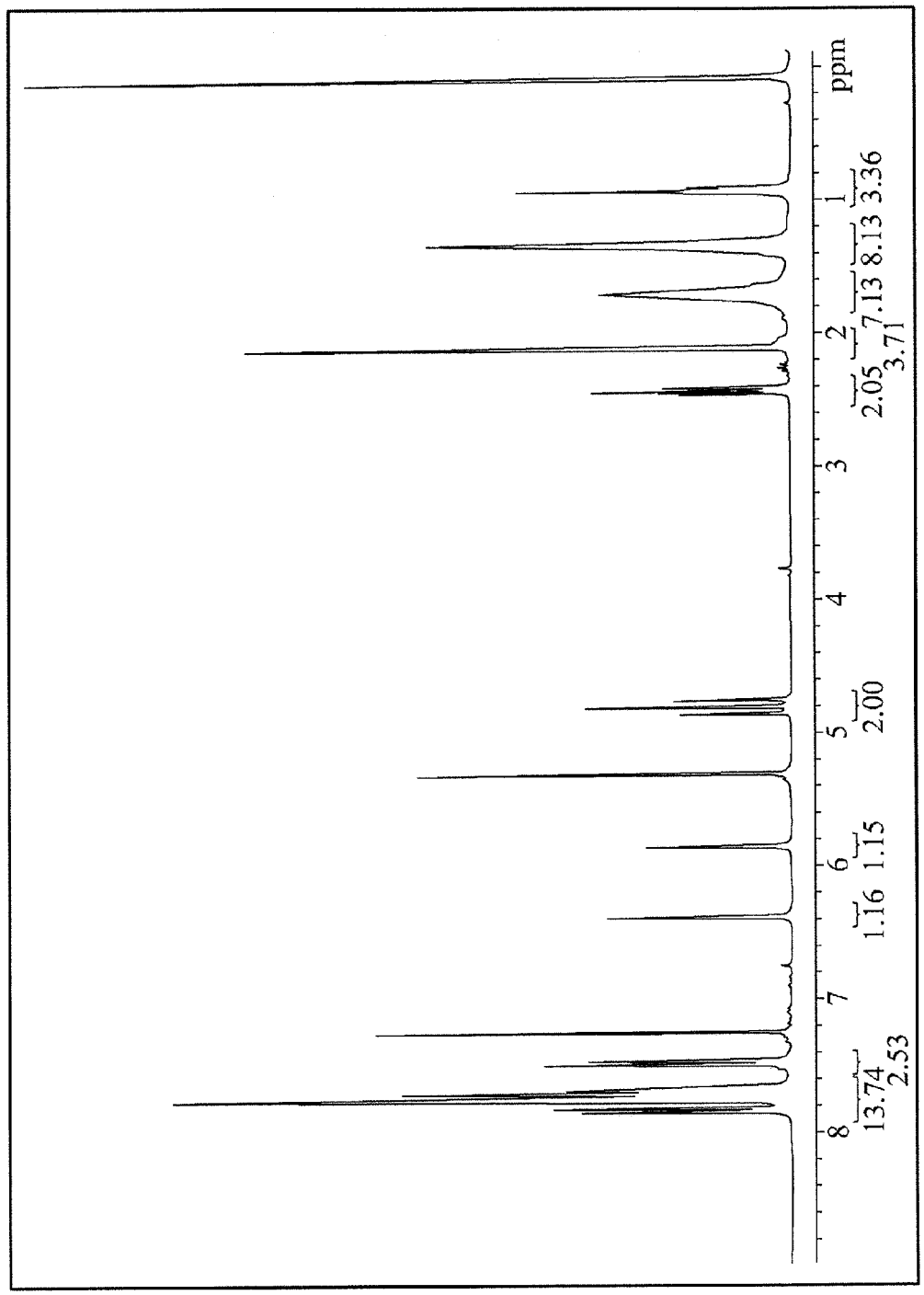
FIG. 7 illustrates a $^1$H-NMR spectrum of a salt obtained according to a synthesis example 8.

Next, the solvents were removed, and drying under a reduced pressure was performed to obtain about 8.46 g (a yield: 97.2%) of a heptanoic acid-2,2-difluoro-2-sulfo-ethyl ester diphenyl-4-methacroyloxy-phenylsulfonium salt, and a structure of the heptanoic acid-2,2-difluoro-2-sulfo-ethyl ester diphenyl-4-methacroyloxy-phenylsulfonium salt was observed by $^1$H-NMR (see FIG. 7):

$^1$H-NMR (chloroform-d3, reference: tetramethylsilane): (ppm) 0.83 (t, 3H), 1.32 (m, 6H), 1.61 (m, 2H), 1.38 (t, 2H), 2.05 (s, 3H), 4.78 (t, 2H), 5.83 (s, 1H), 6.40 (s, 1H), 7.51 (d, 2H), 7.65-7.78 (m, 10H), 7.85 (d, 2H), $^1$H-NMR (chloroform-d3, reference: tetramethylsilane): (ppm) 4.98 (t, 2H), 7.05 (d, 2H), 7.38-7.78 (m, 15H), 8.12 (d, 2H),

[Equation 8]

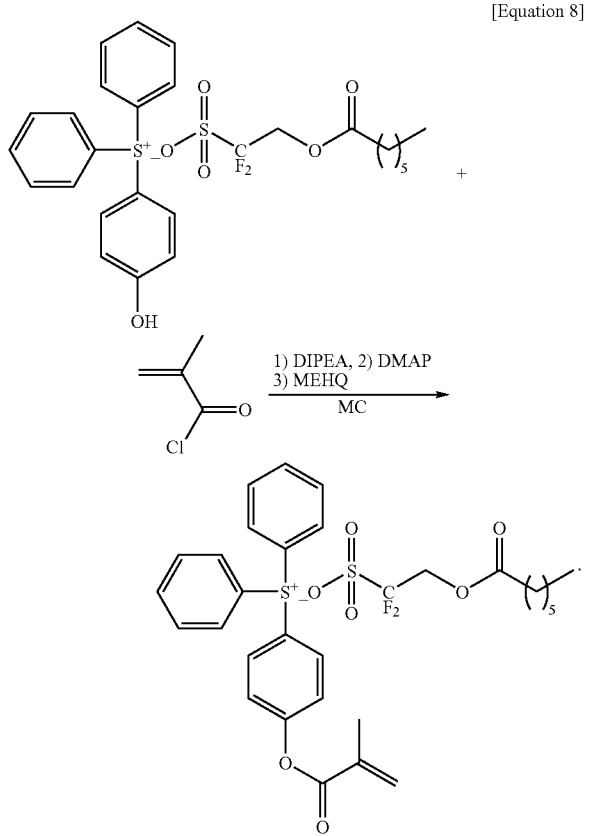

[Equation 9]

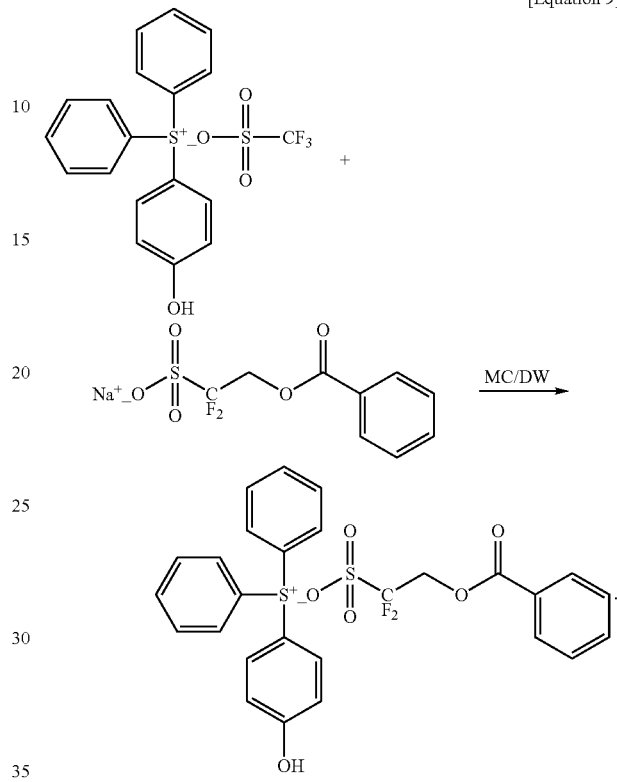

Synthesis Example 9

Figure 8:
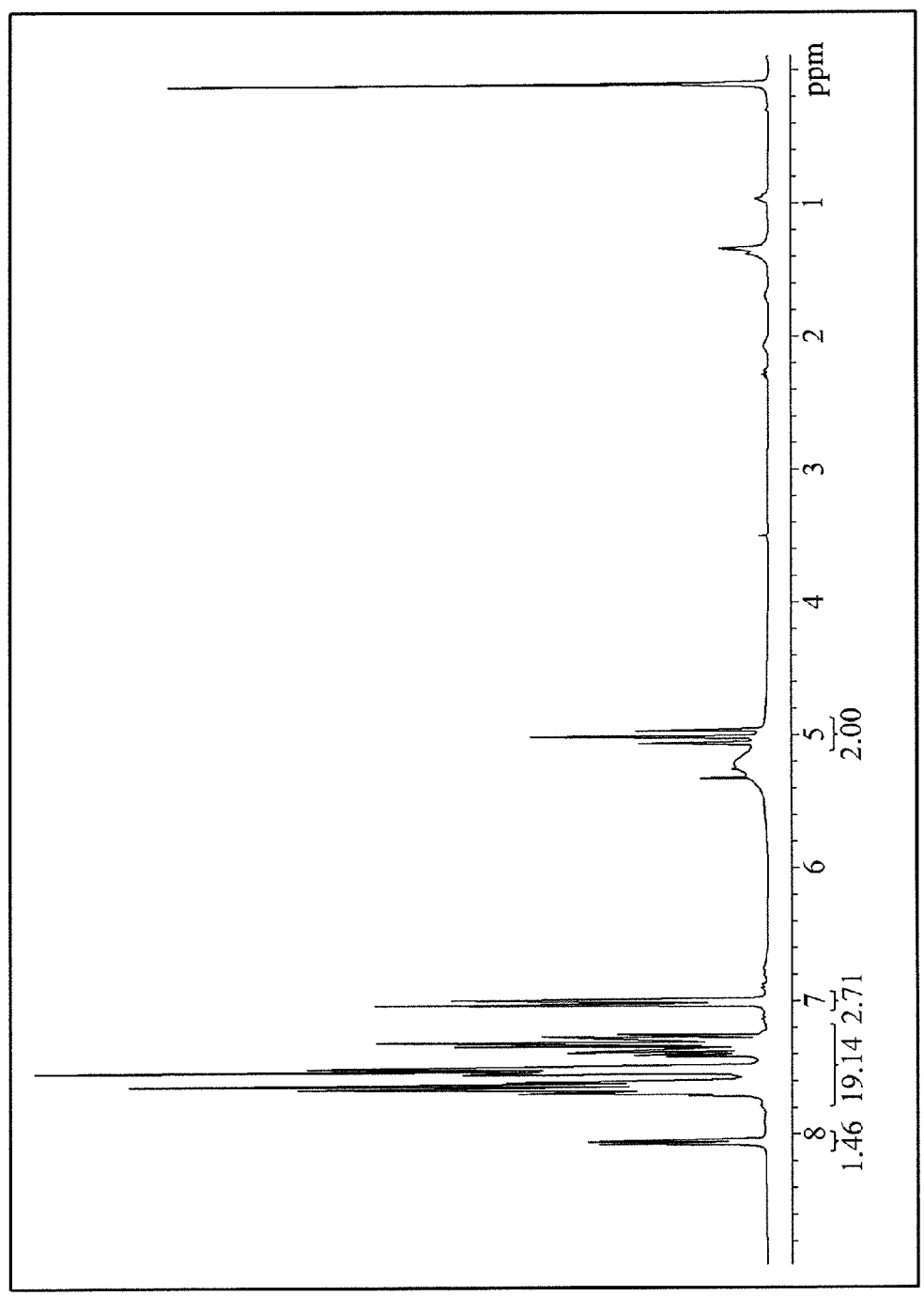
FIG. 8 illustrates a $^1$H-NMR spectrum of a salt obtained according to a synthesis example 9.

Benzoic acid-2,2-difluoro-2-sulfo-ethyl Ester Diphenyl-4-hydroxyphenylsulfonium Salt Synthesis About 6 g of the diphenyl-4-hydroxyphenylsulfonium trifluoromethanesulfonate salt manufactured in the synthesis example 3 and about 4.84 g of a benzoic acid-2,2-difluoro-2-sulfo-ethyl ester sodium salt were dissolved in about 100 ml of an MC and about 100 ml of water, and a synthesis reaction (see Equation 9 below) was performed while strongly stirring for about three hours. In this instance, a process of the synthesis reaction was observed by $^{19}$F NMR using a small amount of an extracted organic phase. The organic phase was extracted when the synthesis reaction was terminated, and washed using the MC of a soluble solvent and hexane of a sparingly soluble solvent. Next, the solvents were removed, and drying under a reduced pressure was performed to obtain about 4.3 g (a yield: about 56.4%) of a benzoic acid-2,2-difluoro-2-sulfo-ethyl ester diphenyl-4-hydroxyphenylsulfonium salt, and a structure of the benzoic acid-2,2-difluoro-2-sulfo-ethyl ester diphenyl-4-hydroxyphenylsulfonium salt was observed by $^1$H-NMR (see FIG. 8):

Synthesis Example 10

Benzoic acid-2,2-difluoro-2-sulfo-ethyl Ester Diphenyl-4-methacroyloxy-phenylsulfonium Salt Synthesis About 4.3 g of the benzoic acid-2,2-difluoro-2-sulfo-ethyl ester diphenyl-4-hydroxyphenylsulfonium salt manufactured in the synthesis example 9, about 0.81 ml of methacryloyl chloride, and about 9.7 mg of 4-methoxyphenol (MEHQ) were mixed and stirred in about 150 ml of an MC, about 2.1 ml of diisopropylethylamine (DIPEA) was gradually dropped using a dropping funnel under an ice bath, and a synthesis reaction (see Equation 10 below) was performed while stirring about three hours at room temperature. In this instance, 4-dimethylaminopyridine (DMAP) was used as a reaction catalyst, and a process of the synthesis reaction was observed by $^{19}$F NMR using a small amount of an extracted organic phase. The organic phase was extracted when the synthesis reaction was terminated, and washed using 1N HCl, distilled water, a saturated sodium bicarbonate aqueous solution, and distilled water in the stated order (three times).

Figure 9:
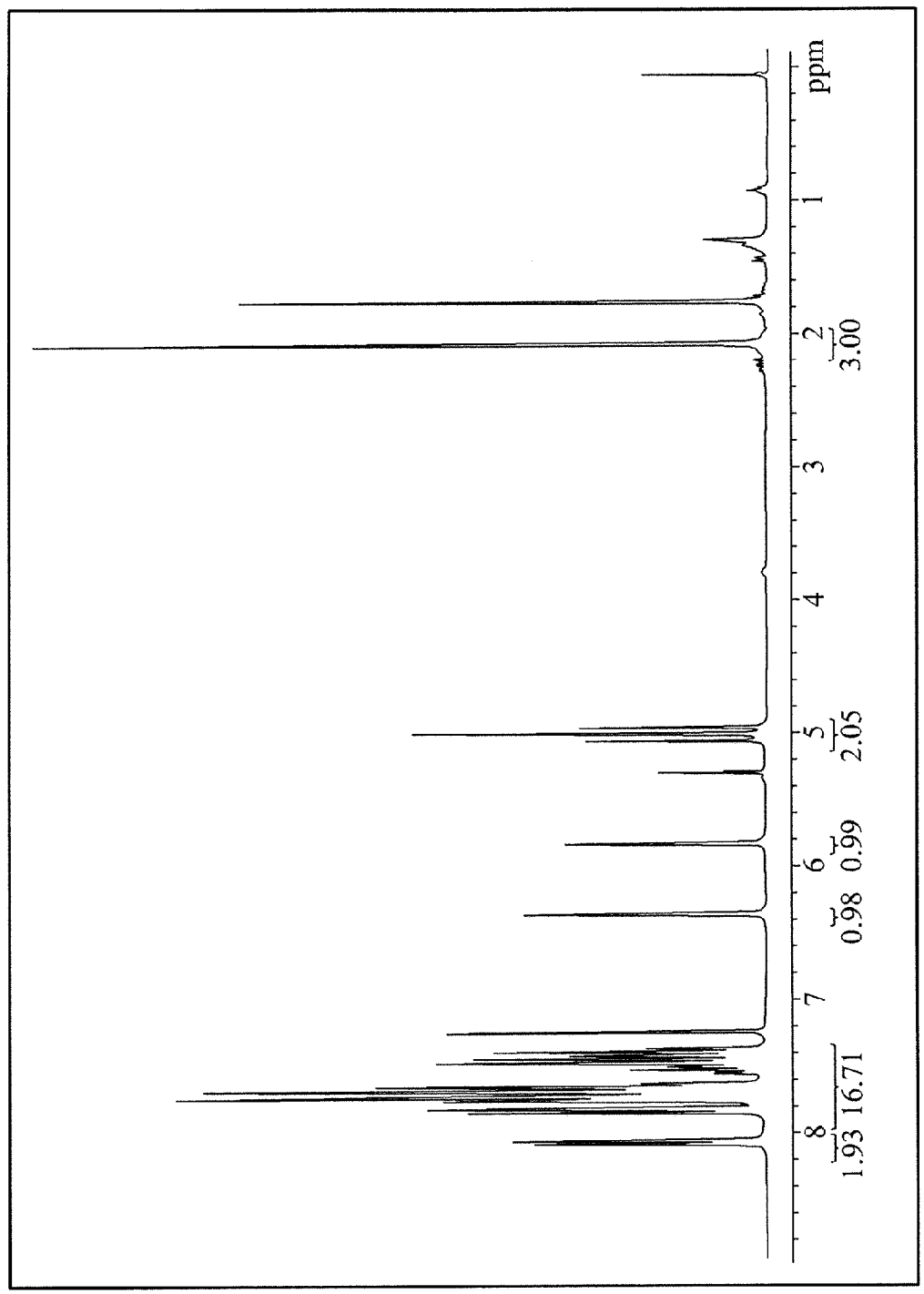
FIG. 9 illustrates a $^1$H-NMR spectrum of a salt obtained according to a synthesis example 10.

Next, a solvent was removed, and washing with the MC of a soluble solvent and hexane of a sparingly soluble solvent was performed. Next, the solvents were removed, and drying under a reduced pressure was performed to obtain about 3.87 g (a yield: about 80%) of a benzoic acid-2,2-difluoro-2-sulfo-ethyl ester diphenyl-4-methacroyloxy-phenylsulfonium salt, and a structure of the benzoic acid-2,2-difluoro-2-sulfo-ethyl ester diphenyl-4-methacroyloxy-phenylsulfonium salt was observed by $^1$H-NMR (see FIG. 9):

$^1$H-NMR (chloroform-d3, reference: tetramethylsilane): (ppm) 2.05 (s, 3H), 4.98 (t, 2H), 7.38-7.78 (m, 15H), 7.91 (d, 2H), 8.12 (d, 2H), $^1$H-NMR (chloroform-d3, reference: tetramethylsilane): (ppm) 1.63-2.05 (m, 15H), 4.78 (m, 2H), 7.05 (d, 2H), 7.38 (d, 2H), 7.55-7.78 (m, 10H), and

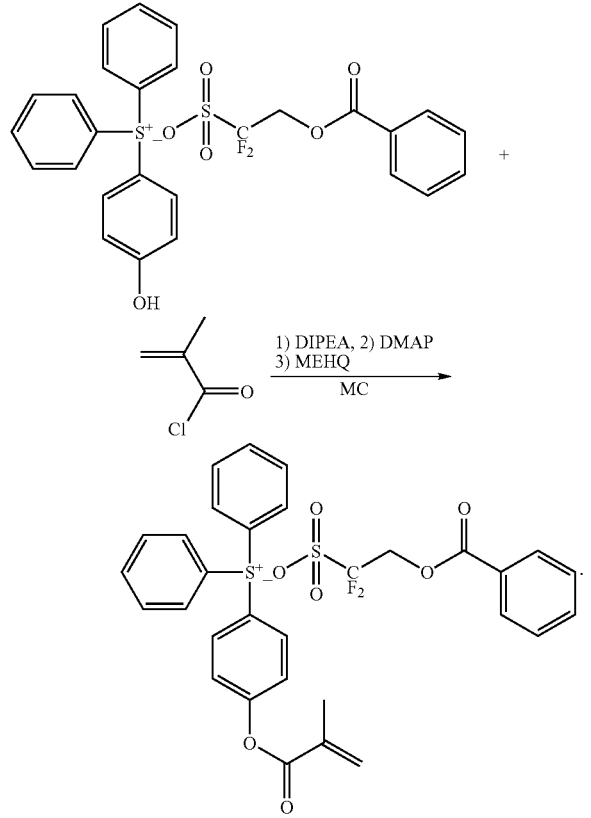

[Equation 10]

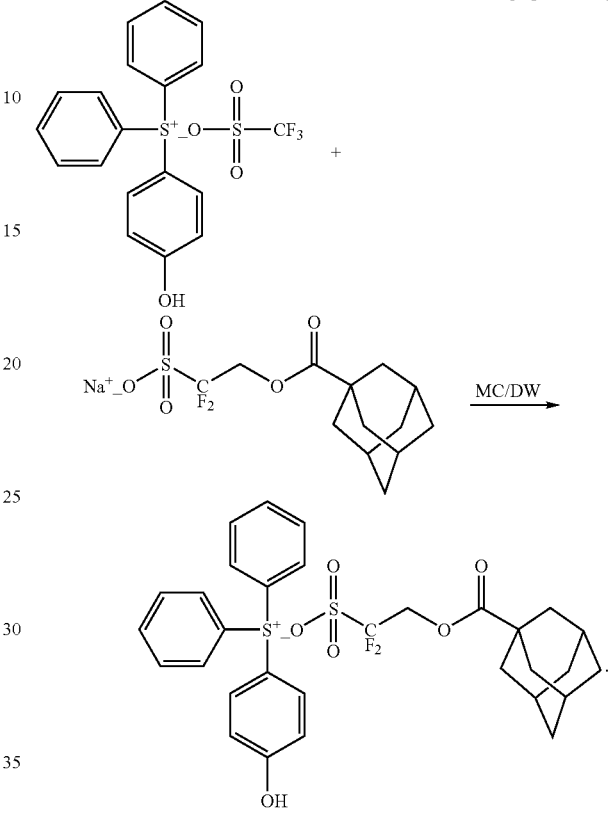

[Equation 11]

Synthesis Example 11

Figure 10:
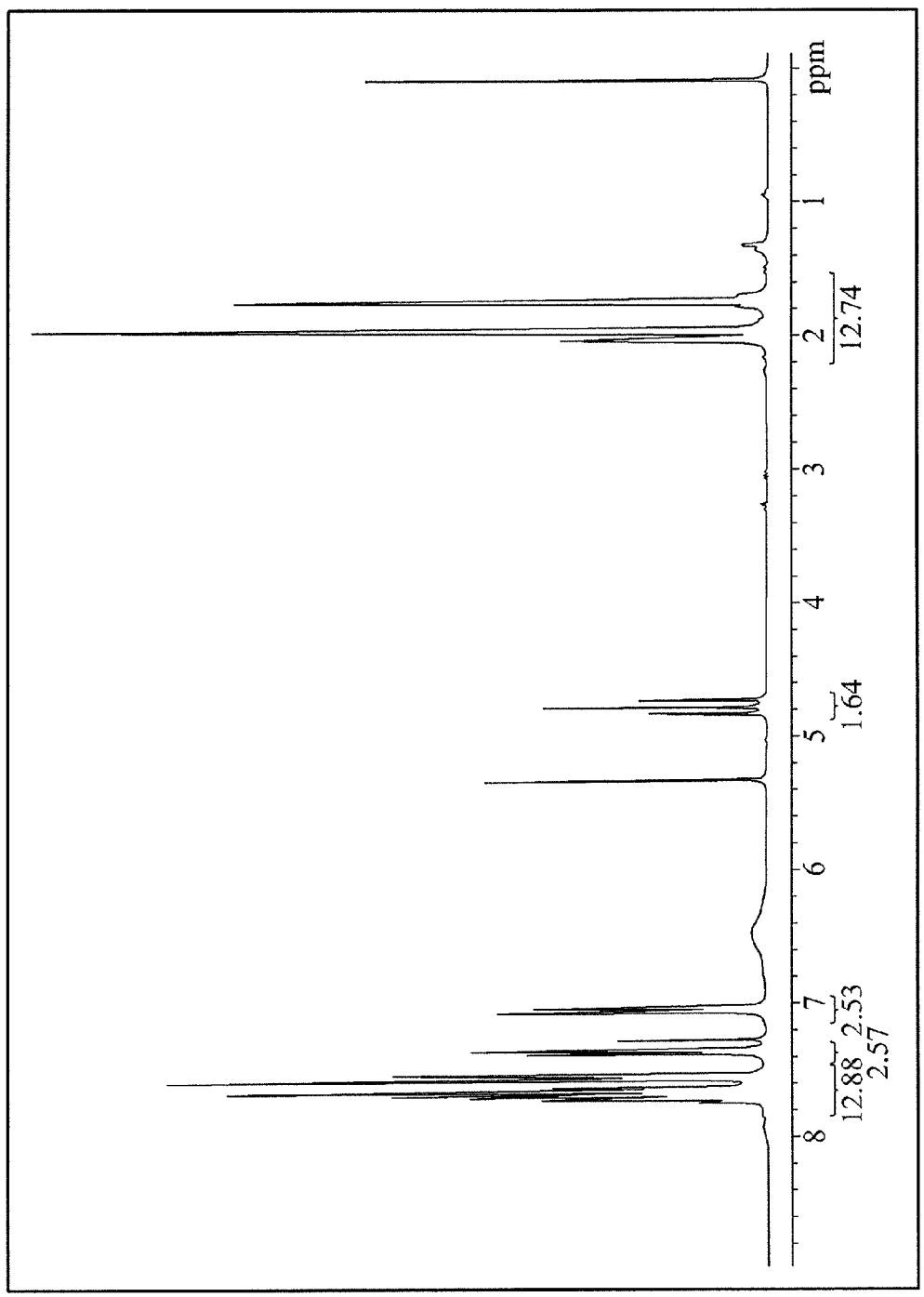
FIG. 10 illustrates a $^1$H-NMR spectrum of a salt obtained according to a synthesis example 11.

Adamantane-1-carboxylic acid-2,2-difluoro-2-sulfo-ethyl Ester Diphenyl-4-hydroxyphenylsulfonium Salt Synthesis About 10 g of the diphenyl-4-hydroxyphenylsulfonium trifluoromethanesulfonate salt manufactured in the synthesis example 3 and about 9.7 g of an adamantane-1-carboxylic acid-2,2-difluoro-2-sulfo-ethyl ester sodium salt were dissolved in about 100 ml of an MC and about 100 ml of water, and a synthesis reaction (see Equation 11 below) was performed while strongly stirring for three hours. In this instance, a process of the synthesis reaction was observed by $^{19}$F NMR using a small amount of an extracted organic phase. The organic phase was extracted when the synthesis reaction was terminated, and washed using the MC of a soluble solvent and hexane of a sparingly soluble solvent. Next, the solvents were removed, and drying under a reduced pressure was performed to obtain about 11.47 g (a yield: about 81.7%) of an adamantane-1-carboxylic acid-2,2-difluoro-2-sulfo-ethyl ester diphenyl-4-hydroxyphenylsulfonium salt, and a structure of the adamantane-1-carboxylic acid-2,2-difluoro-2-sulfo-ethyl ester diphenyl-4-hydroxyphenylsulfonium salt was observed by $^1$H-NMR (see FIG. 10):

Synthesis Example 12

Adamantane-1-carboxylic Acid-2,2-difluoro-2-sulfo-ethyl Ester Diphenyl-4-methacroyloxy-phenylsulfonium Salt Synthesis About 11.47 g of the adamantane-1-carboxylic acid-2,2-difluoro-2-sulfo-ethyl ester diphenyl-4-hydroxyphenylsulfonium salt, about 1.95 ml of methacryloyl chloride, and about 25.5 mg of 4-methoxyphenol (MEHQ) were mixed and stirred in about 150 ml of an MC, about 5 ml of diisopropylethylamine (DIPEA) was gradually dropped using a dropping funnel under an ice bath, and a synthesis reaction (see Equation 12 below) was performed while stirring for about three hours at room temperature. In this instance, 4-dimethylaminopyridine (DMAP) was used as a reaction catalyst, and a process of the synthesis reaction was observed by $^{19}$F NMR using a small amount of an extracted organic phase. The organic phase was extracted when the synthesis reaction was terminated, and washed using 1N HCl, distilled water, a saturated sodium bicarbonate aqueous solution, and distilled water in the stated order (three times).

Figure 11:
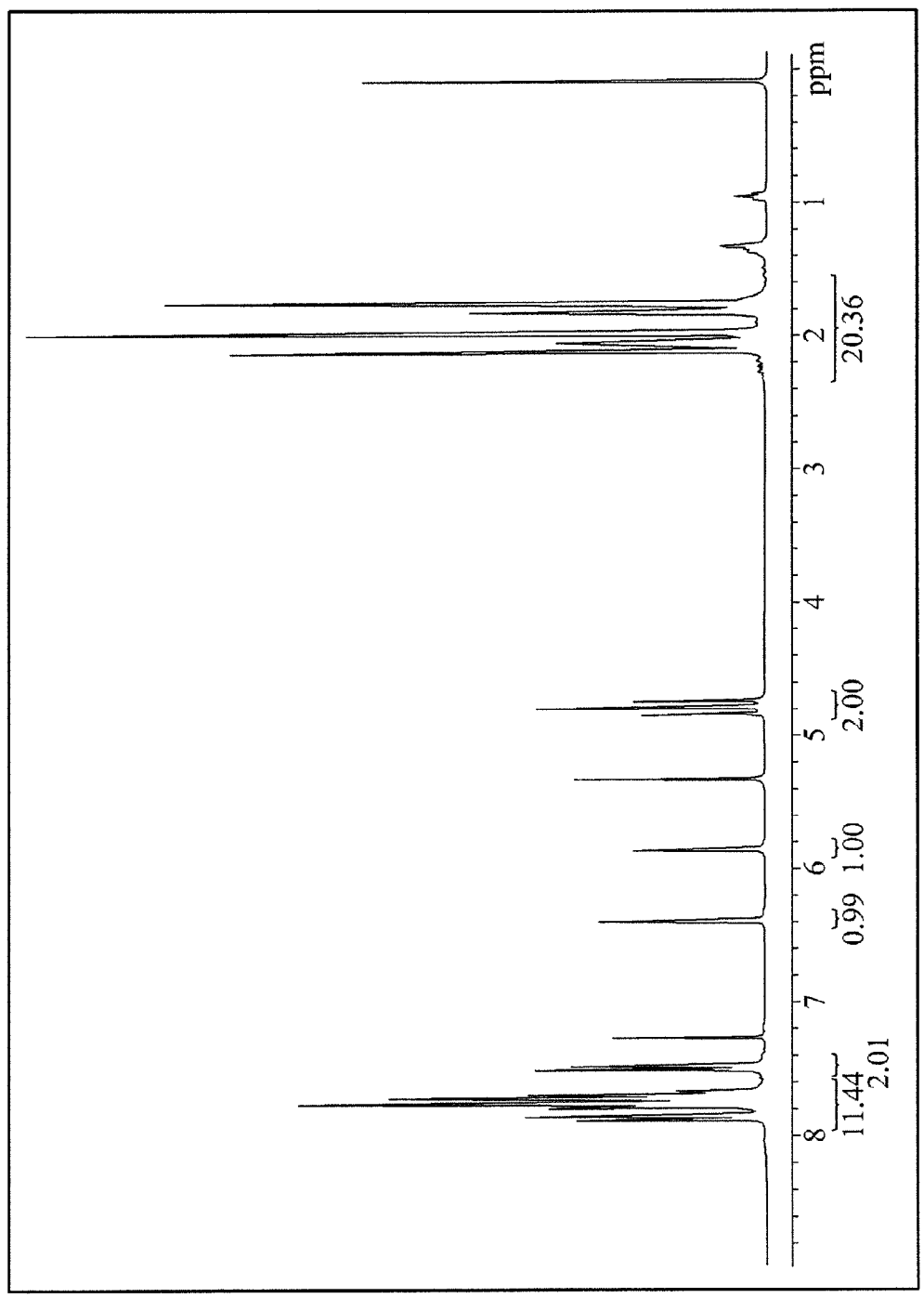
FIG. 11 illustrates a $^1$H-NMR spectrum of a salt obtained according to a synthesis example 12.

Next, a solvent was removed, and washing with the MC of a soluble solvent and hexane of a sparingly soluble solvent was preformed. Next, the solvents were removed, and drying under a reduced pressure was performed to obtain about 10.8 g (a yield: about 85%) of an adamantane-1-carboxylic acid- 2,2-difluoro-2-sulfo-ethyl ester diphenyl-4-methacroyloxy-phenylsulfonium salt, and a structure of the adamantane-1-carboxylic acid-2,2-difluoro-2-sulfo-ethyl ester diphenyl-4-methacroyloxy-phenylsulfonium salt was observed by $^1$H-NMR (see FIG. 11):

$^1$H-NMR (chloroform-d3, reference: tetramethylsilane): (ppm) 1.63-2.05 (m, 18H), 4.78 (m, 2H), 7.38 (d, 2H), 7.55-7.78 (m, 10H), 7.91(d, 2H), and

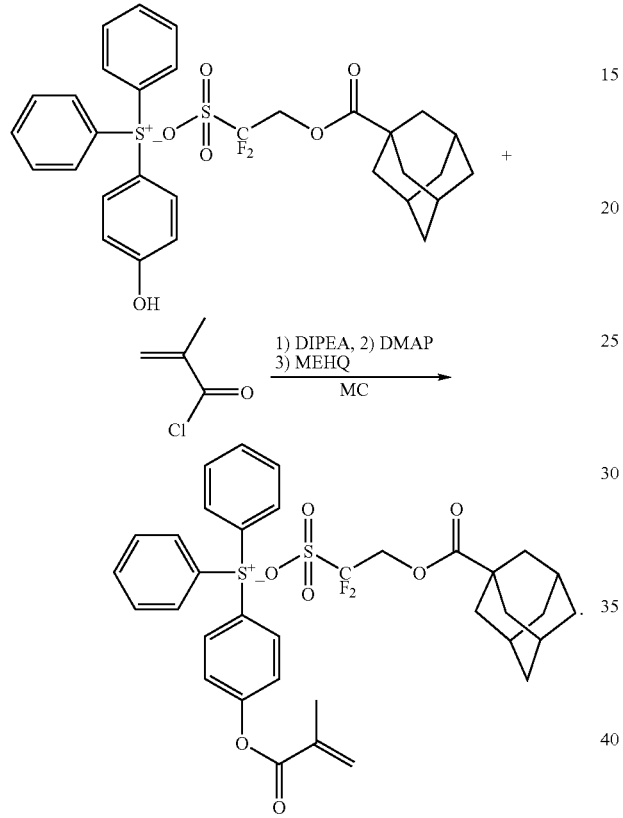

[Equation 12]

Synthesis Example 13

Figure 12:
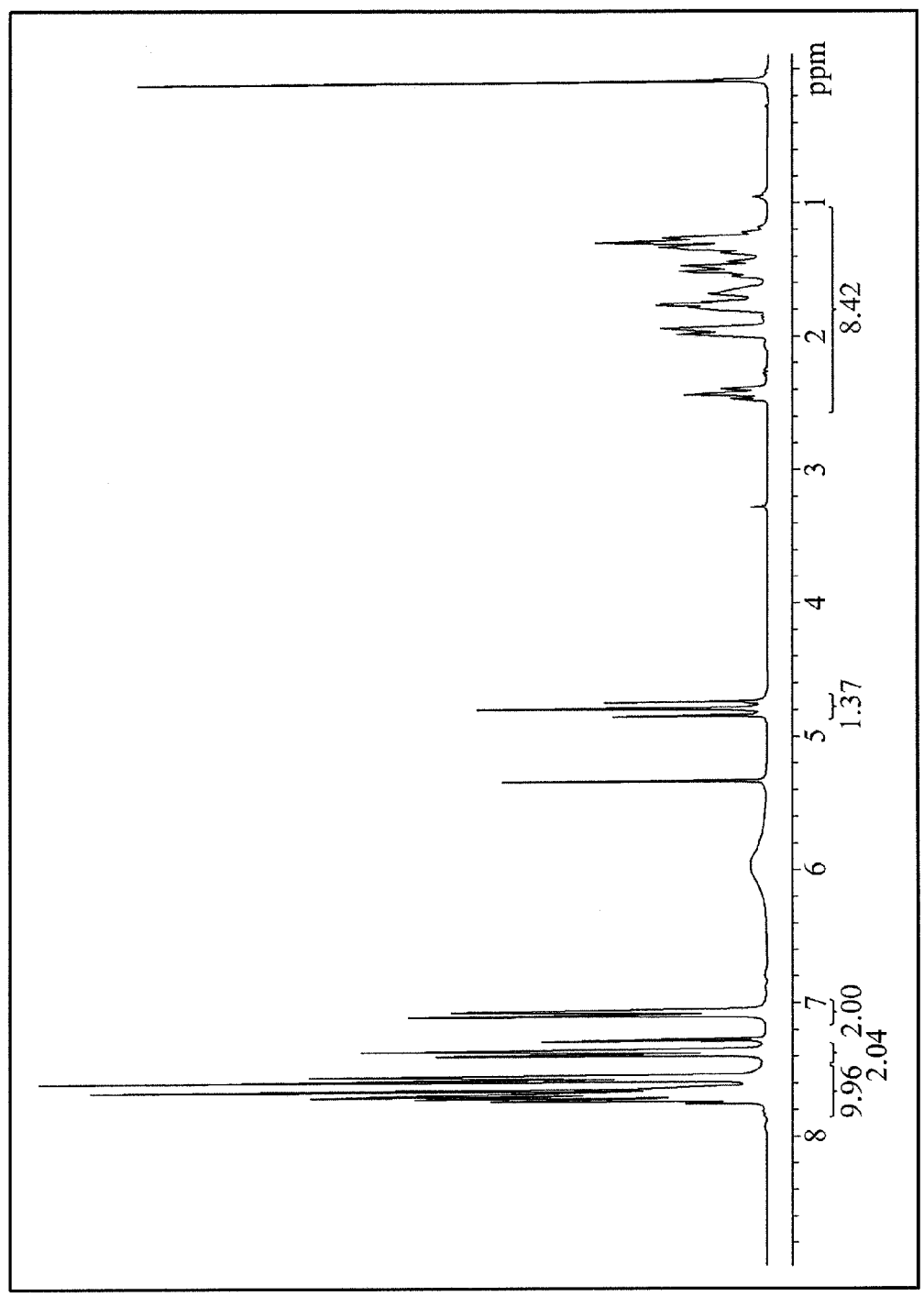
FIG. 12 illustrates a $^1$H-NMR spectrum of a salt obtained according to a synthesis example 13.

Cyclohexanecarboxylic
Acid-2,2-difluoro-2-sulfo-ethyl Ester
Diphenyl-4-hydroxyphenylsulfonium Salt Synthesis About 8 g of the diphenyl-4-hydroxyphenylsulfonium trifluoromethanesulfonate salt manufactured in the synthesis example 3 and about 9.05 g of a cyclohexanecarboxylic acid-2,2-difluoro-2-sulfo-ethyl ester sodium salt were dissolved in about 100 ml of an MC and about 100 ml of water, and a synthesis reaction (see Equation 12 below) was performed while strongly stirring for about three hours. In this instance, a process of the synthesis reaction was observed by $^{19}$F NMR using a small amount of an extracted organic phase. The organic phase was extracted when the synthesis reaction was terminated, and washed using the MC and hexane. Next, the solvents were removed, and drying under a reduced pressure was performed to obtain about 10.67 g (a yield: about 99%) of a cyclohexanecarboxylic acid-2,2-difluoro-2-sulfo-ethyl ester diphenyl-4-hydroxyphenylsulfonium salt, and a structure of the cyclohexanecarboxylic acid-2,2-difluoro-2-sulfo-ethyl ester diphenyl-4-hydroxyphenylsulfonium salt was observed by $^1$H-NMR (see FIG. 12):

$^1$H-NMR (chloroform-d3, reference: tetramethylsilane): (ppm) 1.18-1.85 (m, 10H), 2.39 (m, 1H), 4.78 (m, 2H), 7.05 (d, 2H), 7.38 (d, 2H), 7.55-7.78 (m, 10H), and

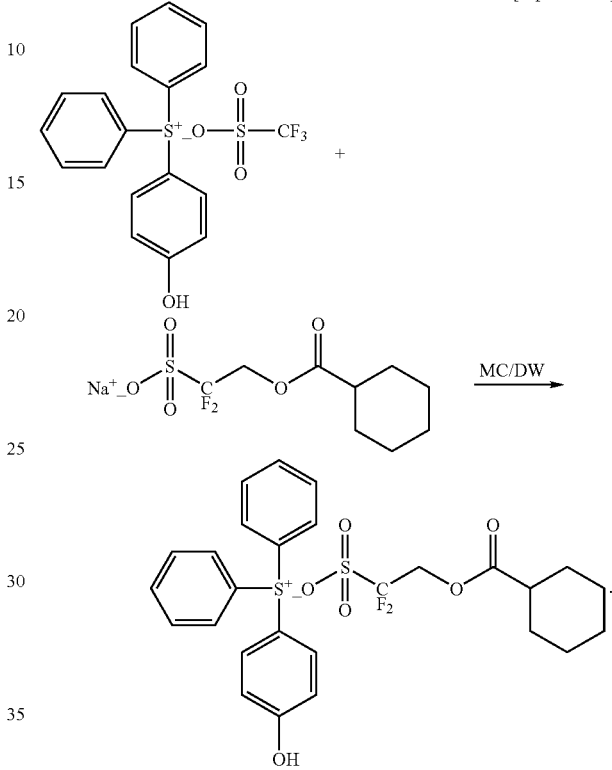

[Equation 13]

Synthesis Example 14

Cyclohexanecarboxylic
Acid-2,2-difluoro-2-sulfo-ethyl Ester
Diphenyl-4-methacroyloxy-phenylsulfonium Salt
Synthesis About 10 g of the cyclohexanecarboxylic acid-2,2-difluoro-2-sulfo-ethyl ester diphenyl-4-hydroxyphenylsulfonium salt manufactured in the synthesis example 13, about 2 ml of methacryloyl chloride, and about 24 mg of 4-methoxyphenol (MEHQ) were mixed and stirred in about 150 ml of an MC, about 5.06 ml of DIPEA was gradually dropped using a dropping funnel under an ice bath, and a synthesis reaction (see Equation 14 below) was performed while stirring for three hours at room temperature. In this instance, DMAP was used as a reaction catalyst, and a process of the synthesis reaction was observed by $^{19}$F NMR using a small amount of an extracted organic phase. The organic phase was extracted when the synthesis reaction was terminated, and washed using 1N HCl, distilled water, a saturated sodium bicarbonate aqueous solution, and distilled water in the stated order (three times).

Figure 13:
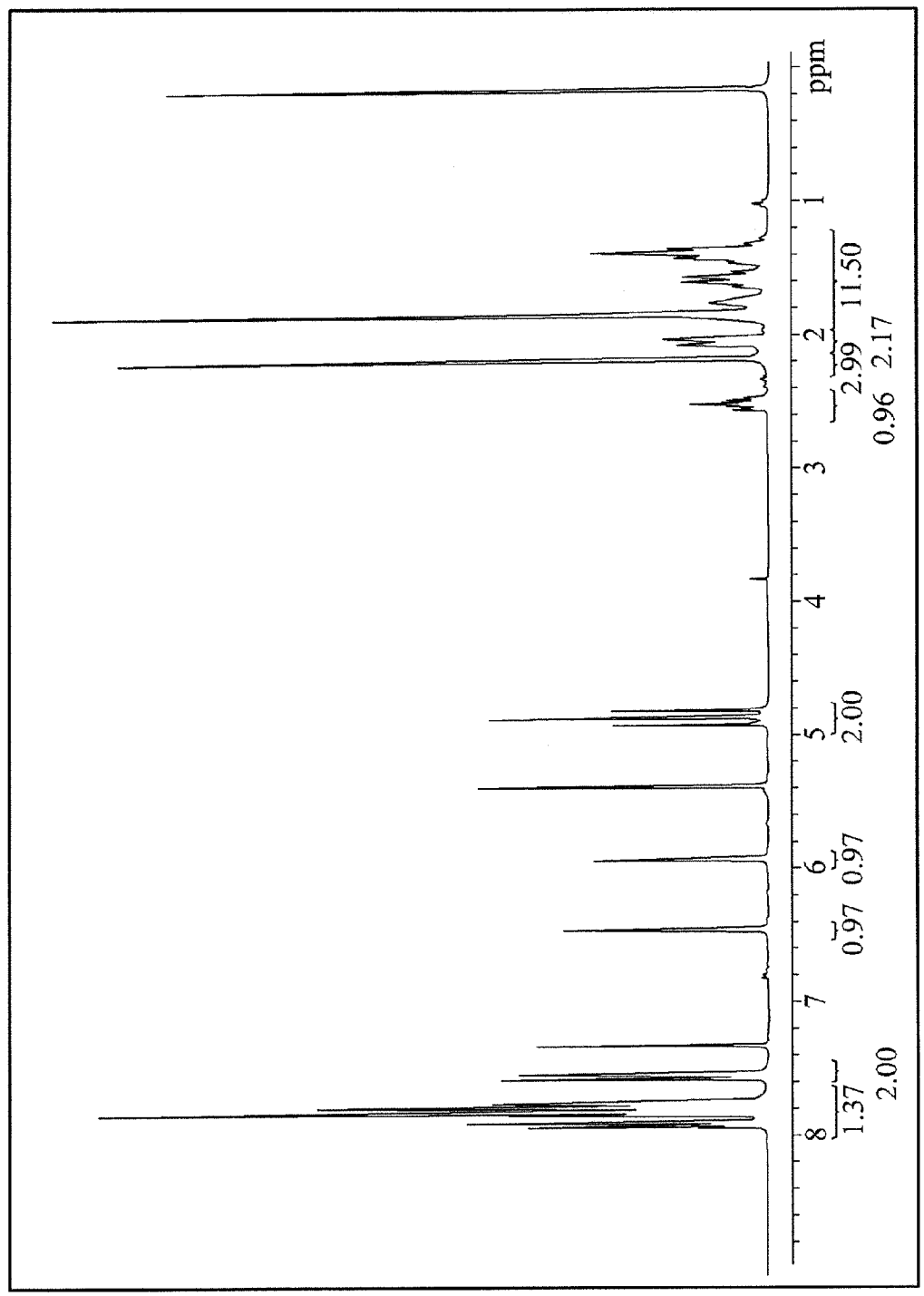
FIG. 13 illustrates a $^1$H-NMR spectrum of a salt obtained according to a synthesis example 14.

Next, a solvent was removed, and washing with the MC and hexane was performed. Next, the solvents was removed, and drying under a reduced pressure was performed to obtain about 7.88 g (a yield: about 65.7%) of a cyclohexanecarboxylic acid-2,2-difluoro-2-sulfo-ethyl ester diphenyl-4-methacroyloxy-phenylsulfonium salt, and a structure of the cyclohexanecarboxylic acid-2,2-difluoro-2-sulfo-ethyl ester diphenyl-4-methacroyloxy-phenylsulfonium salt was observed by $^1$H-NMR (see FIG. 13):

$^1$H-NMR (chloroform-d3, reference: tetramethylsilane): (ppm) 1.18-1.85 (m, 13H), 2.39 (m, 1H), 4.78 (m, 2H), 5.82 (s, 1H), 6.38 (s, 1H), 7.38 (d, 2H), 7.65-7.78 (m, 10H), 7.83 (d, 2H), and

[Equation 14]

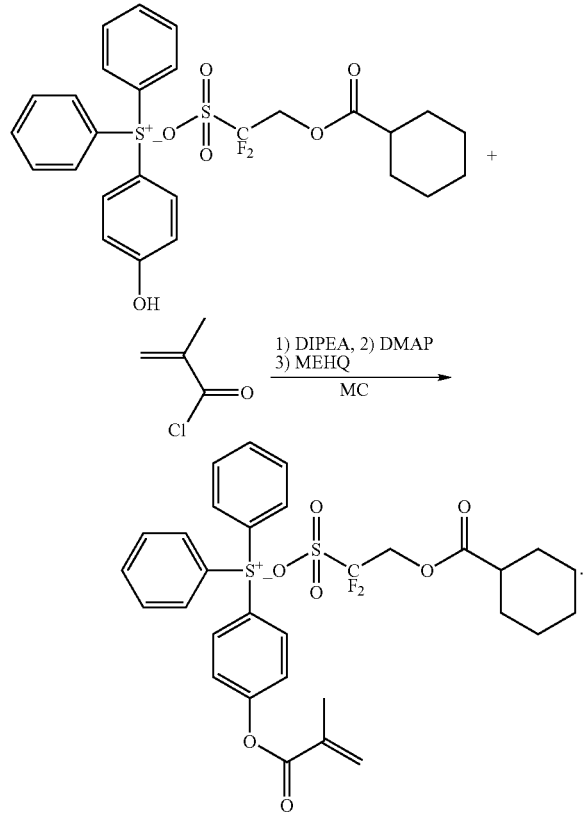

Synthesis Example 15

Copolymer Synthesis

Figure 14:
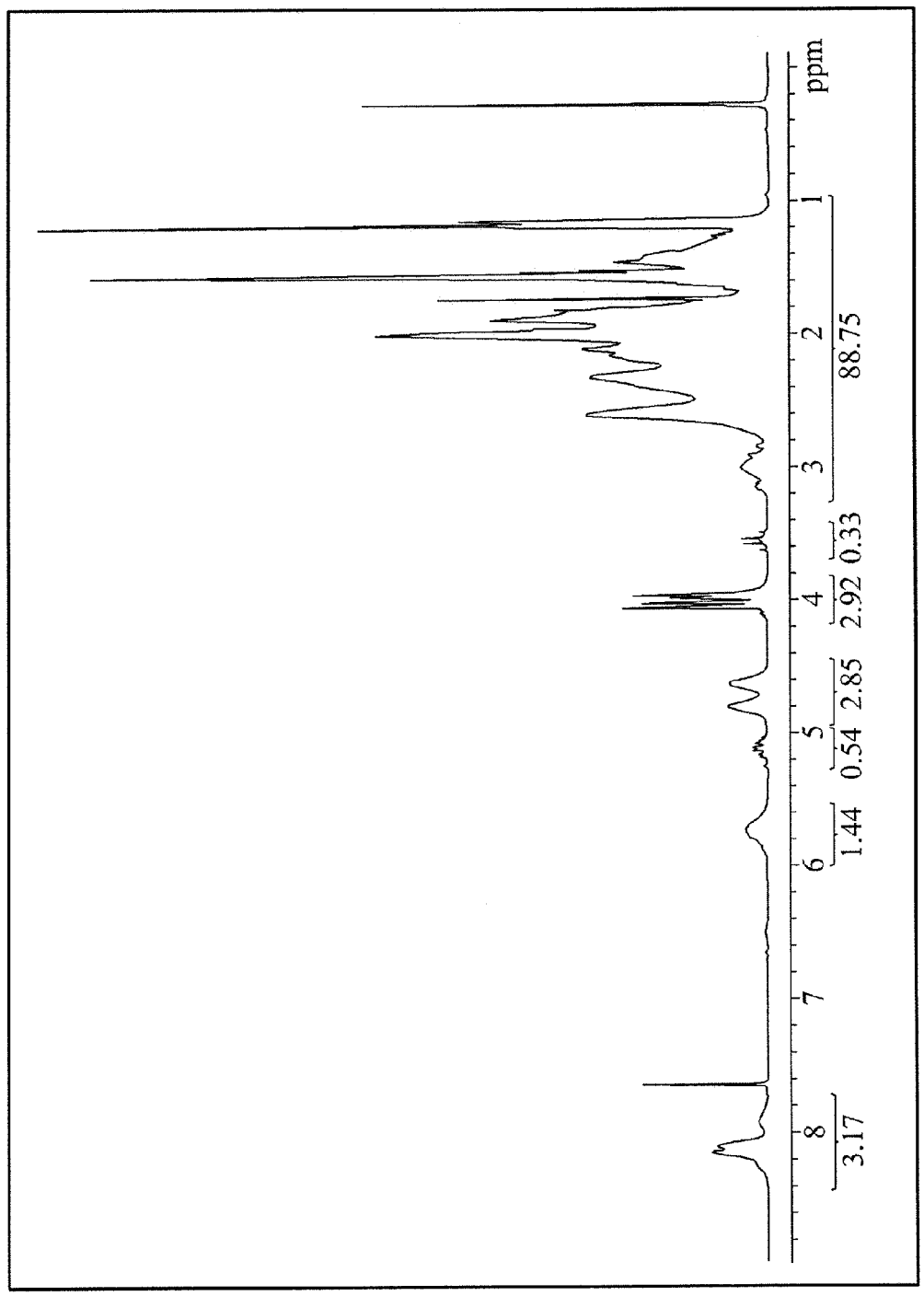
FIG. 14 illustrates a $^1$H-NMR spectrum of a salt obtained according to a synthesis example 15.
Figure 15:
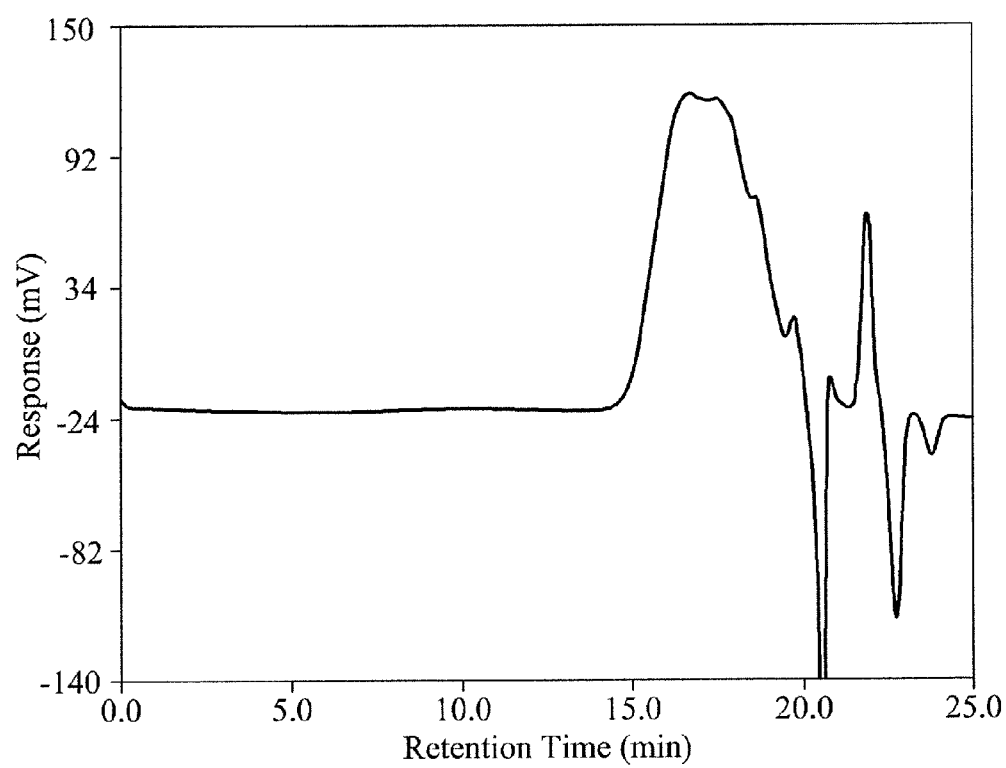
FIG. 15 is a graph illustrating gel permeation chromatography (GPC) data of a copolymer obtained according to a synthesis example 15.

About 15.9 g of 2-methyl-2-adamantyl acrylate, about 10.2 g of γ-butyrolactyl methacrylate, about 14.1 g of 3-hydroxy-1-adamantyl methacrylate, and about 6.76 g of the bicyclo[2.2.1]heptane-2-carboxylic acid-2,2-difluoro-2-sulfo-ethyl ester diphenyl-4-methacroyloxy-phenylsulfonium salt manufactured in the synthesis example 5 which act as monomers for polymerization were prepared, and dissolved in about 62 g of 1,2-dichloroethane. Next, about 2.26 g of norbornene, about 5.3 g of azobisisobutyronitrile (AIBN) of a polymerization initiator, and about 123.9 g of 1,2-dichloroethane of a polymerization solvent were added in a flask of about 500 ml, and stirred for about one hour at room temperature under injection of a nitrogen gas. Next, the monomers for polymerization were gradually dropped on the flask for about one hour while maintaining a temperature of a reaction container at about 65° C., and then a polymerization reaction was performed on the monomers for about 16 hours. Next, a reaction solution in which the polymerization reaction was completed was cooled to room temperature. Next, the reaction solution cooled to room temperature was precipitated in hexane, and then filtered. Next, the filtered solution was washed several times using an identical solvent to a solvent used when being filtered, and then was subjected to drying under a reduced pressure to obtain about 47 g (a yield: 95%) of a copolymer represented as Chemical formula 9, and a structure of the copolymer was observed by $^1$H-NMR (see FIG. 14). Next, characteristics of a synthesized copolymer were measured using gel permeation chromatography (GPC), and the results are shown in FIG. 15. The GPC was performed under conditions in which a system was a DM400+External RI, a column was G4000Hhr+G2500Hhr, a solvent was tetrahydrofuran (THF), a flow rate was about 1.000 mL/min, a concentration was about 0.000 mg/mL, and Inj. Vol was about 100.0 μl. According to the results of the GPC, a weight-average molecular weight (Mw) in terms of polystyrene of the copolymer was about 1,680, and a number-average molecular weight (Mn) was about 920, and a molecular weight distribution (Mw/Mn) was about 1.83.

Synthesis Example 16

Copolymer Synthesis

Figure 16:
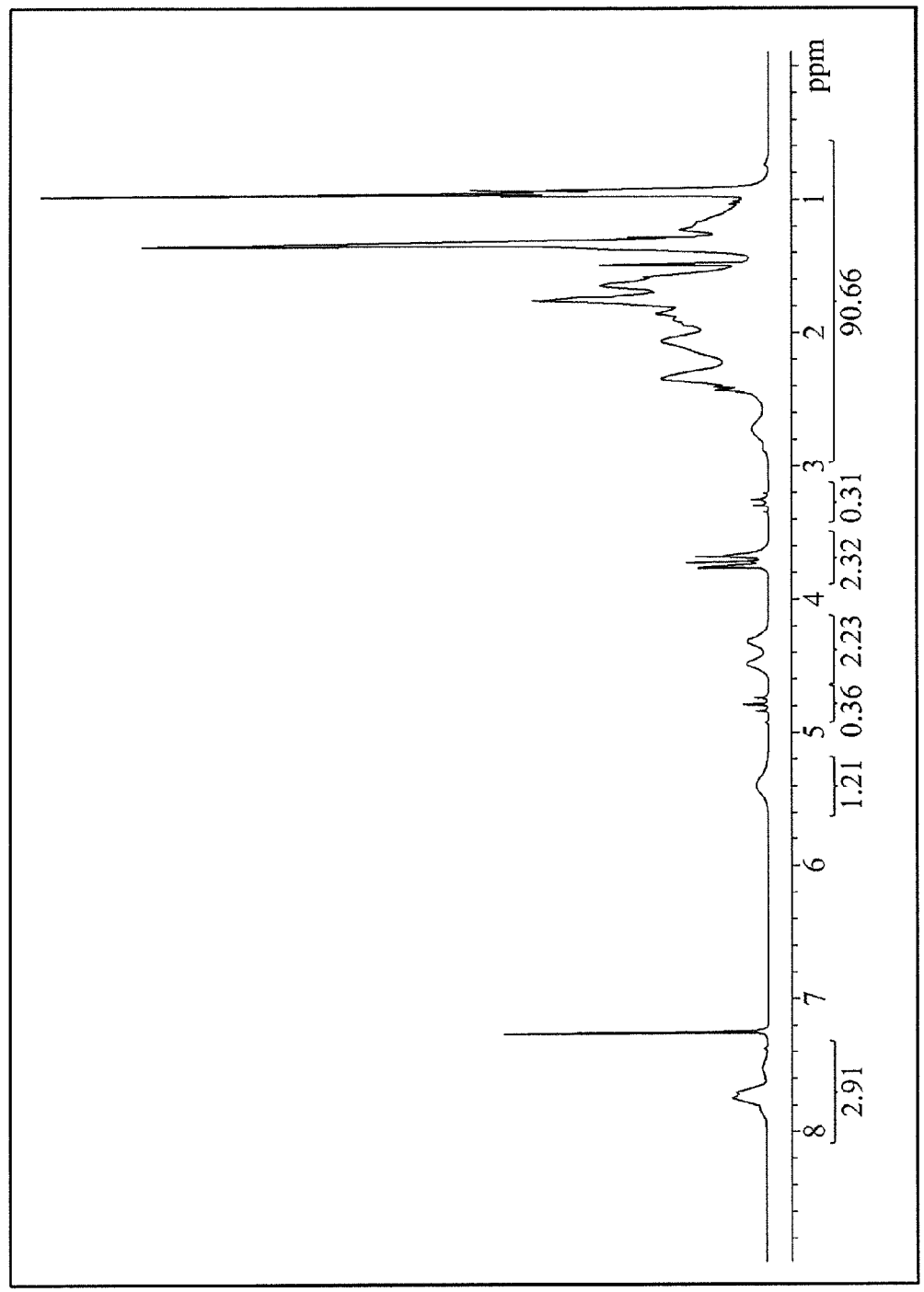
FIG. 16 illustrates a $^1$H-NMR spectrum of a copolymer obtained according to a synthesis example 16.

About 15.9 g of 2-methyl-2-adamantyl acrylate, about 10.2 g of γ-butyrolactyl methacrylate, about 4.9 g of 3-hydroxy-1-adamantyl methacrylate, and about 6.1 g of the bicyclo[2.2.1]heptane-2-carboxylic acid-2,2-difluoro-2-sulfo-ethyl ester diphenyl-4-acroyloxy-phenylsulfonium salt manufactured in the synthesis example 6 which act as monomers for polymerization were prepared, and dissolved in about 62 g of 1,2-dichloroethane. Next, about 2.26 g of norbornene, about 5.3 g of AIBN of a polymerization initiator, and about 123.9 g of 1,2-dichloroethane of a polymerization solvent were added in a flask of about 500 ml, and stirred for about one hour at room temperature under injection of a nitrogen gas. Next, the monomers for polymerization were gradually dropped on the flask for about one hour while maintaining a temperature of a reaction container at about 65° C., and then a polymerization reaction was performed on the monomers for about 16 hours. Next, a reaction solution in which the polymerization reaction was completed was cooled to room temperature. Next, the reaction solution cooled to room temperature was precipitated in hexane, and then filtered. Next, the filtered solution was washed several times using an identical solvent to a solvent used when being filtered, and then was subjected to drying under a reduced pressure to obtain about 36 g (a yield: 75%) of a copolymer represented as Chemical formula 17, and a structure of the copolymer was observed by $^1$H-NMR (see FIG. 16). Next, characteristics of a synthesized copolymer were measured using GPC. The GPC was performed under the same conditions as those in the synthesis example 15. According to the results of the GPC, a weight-average molecular weight (Mw) in terms of polystyrene of the copolymer was about 1,550, and a number-average molecular weight (Mn) was about 900, and a molecular weight distribution (Mw/Mn) was about 1.72.

Synthesis Example 17

Copolymer Synthesis

Figure 17:
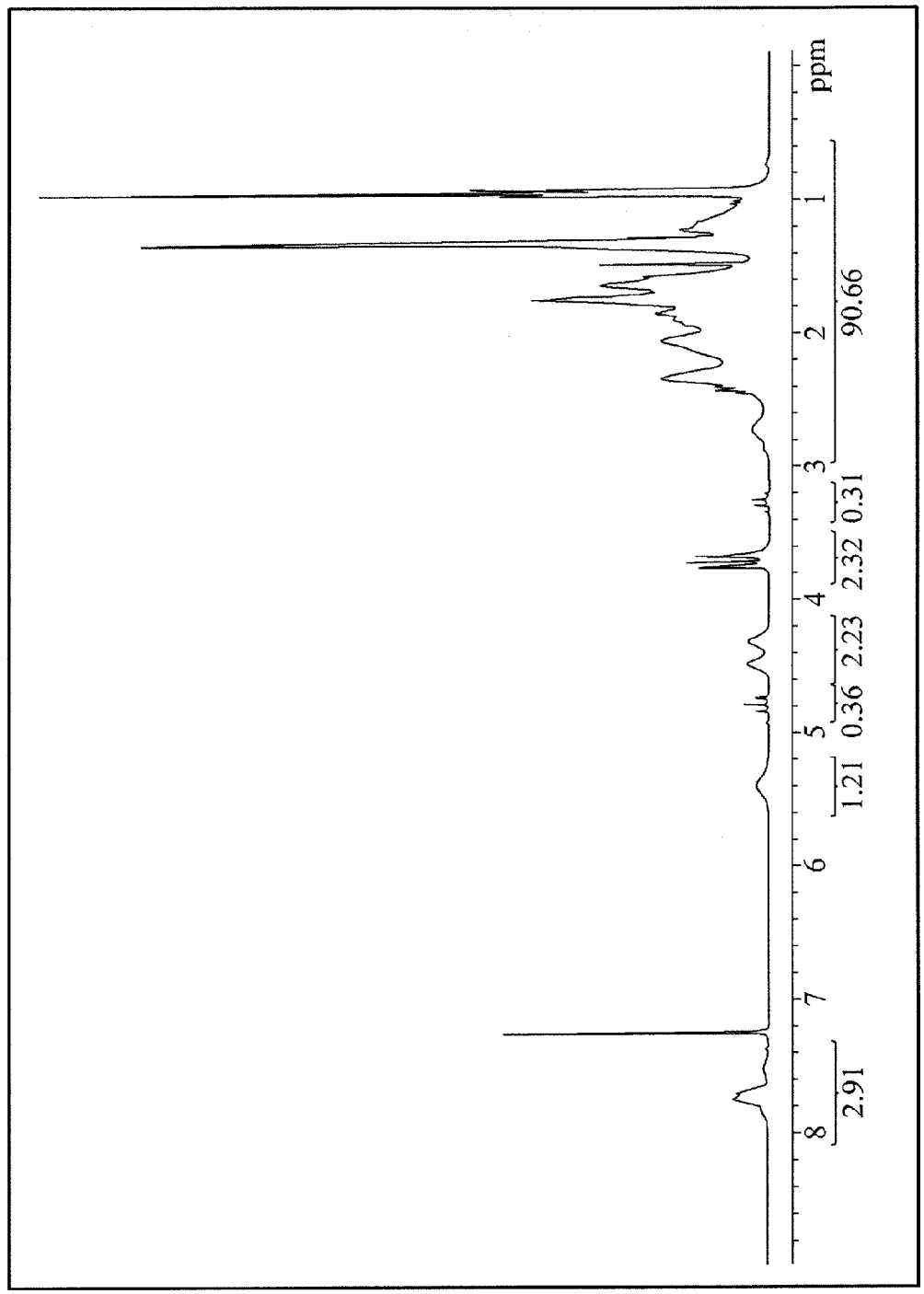
FIG. 17 illustrates a $^1$H-NMR spectrum of a copolymer obtained according to a synthesis example 17.
Figure 18:
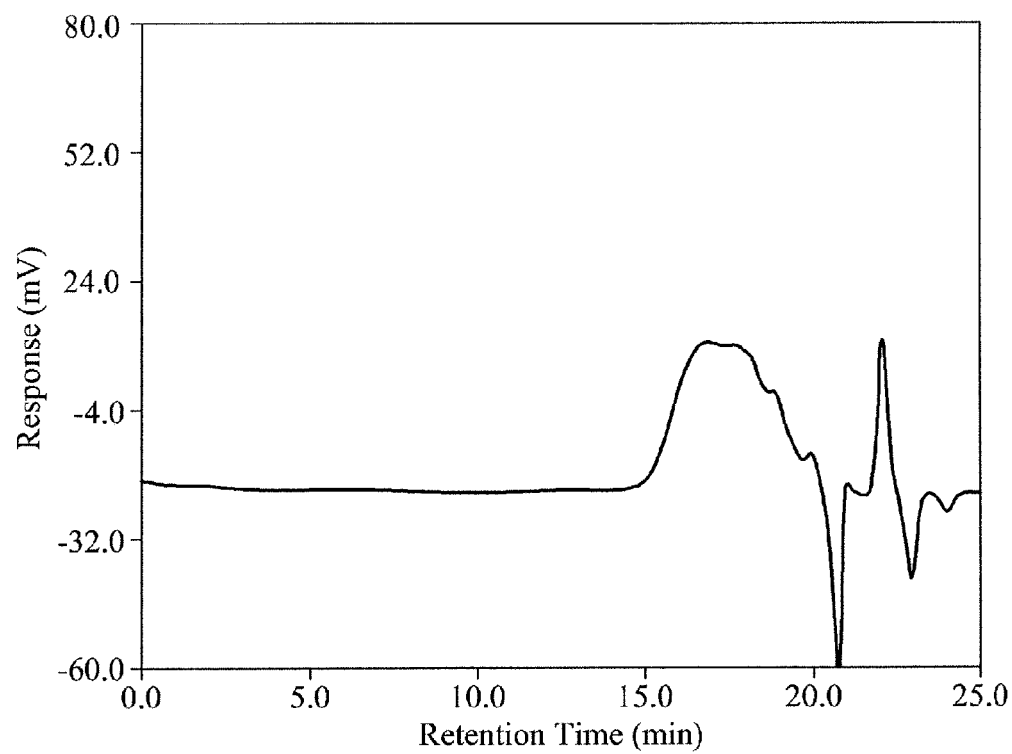
FIG. 18 is a graph illustrating GPC data of a copolymer obtained according to a synthesis example 17.

About 18.0 g of 2-methyl-2-adamantyl acrylate, about 11.6 g of γ-butyrolactyl methacrylate, about 16.1 g of 3-hydroxy-1-adamantyl methacrylate, and about 8.46 g of the heptanoic acid-2,2-difluoro-2-sulfo-ethyl ester diphenyl-4-methacroyloxy-phenylsulfonium salt manufactured in the synthesis example 8 which act as monomers for polymerization were prepared, and dissolved in about 71.2 g of 1,2-dichloroethane. Next, about 2.6 g of norbornene, about 6 g of AIBN of a polymerization initiator, and about 142.5 g of 1,2-dichloroethane of a polymerization solvent were added in a flask of about 500 ml, and stirred for about one hour at room temperature under injection of a nitrogen gas. Next, the monomers for polymerization were gradually dropped on the flask for about one hour while maintaining a temperature of a reaction container at about 65° C., and then a polymerization reaction was performed on the monomers for about 16 hours. Next, a reaction solution in which the polymerization reaction was completed was cooled to room temperature. Next, the reaction solution cooled to room temperature was precipitated in hexane, and then filtered. Next, the filtered solution was washed several times using an identical solvent to a solvent used when being filtered, and then was subjected to drying under a reduced pressure to obtain about 46 g (a yield: 81%) of a copolymer represented as Chemical formula 10, and a structure of the copolymer was observed by $^1$H-NMR (see FIG. 17). Next, characteristics of a synthesized copolymer were measured using GPC, and the results are shown in FIG. 18. The GPC was performed under the same conditions as those in the synthesis example 15. According to the results of the GPC, a weight-average molecular weight (Mw) in terms of polystyrene of the copolymer was about 1,620, and a number-average molecular weight (Mn) was about 780, and a molecular weight distribution (Mw/Mn) was about 2.08.

Synthesis Example 18

Copolymer Synthesis

Figure 19:
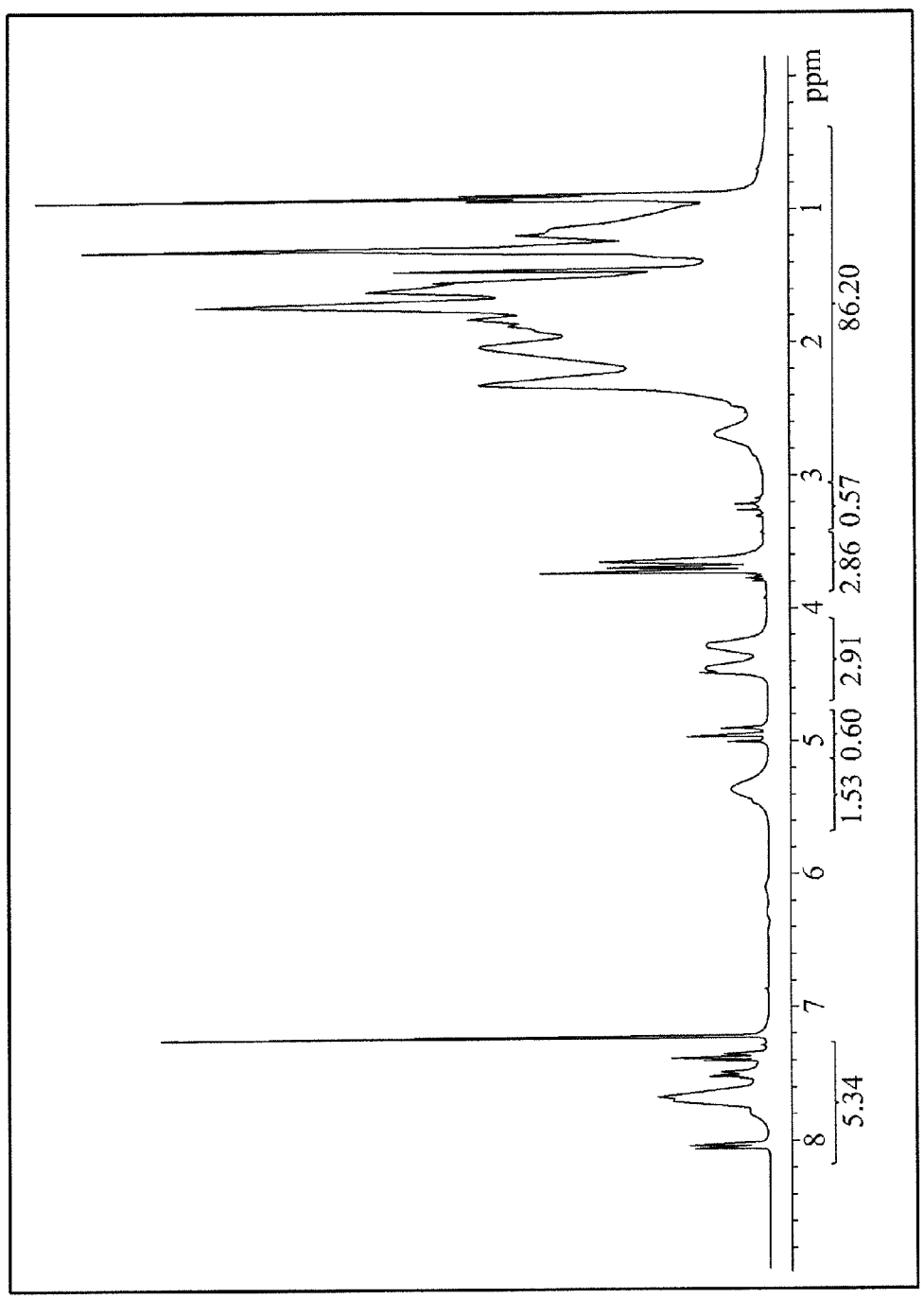
FIG. 19 illustrates a $^1$H-NMR spectrum of a copolymer obtained according to a synthesis example 18.
Figure 20:
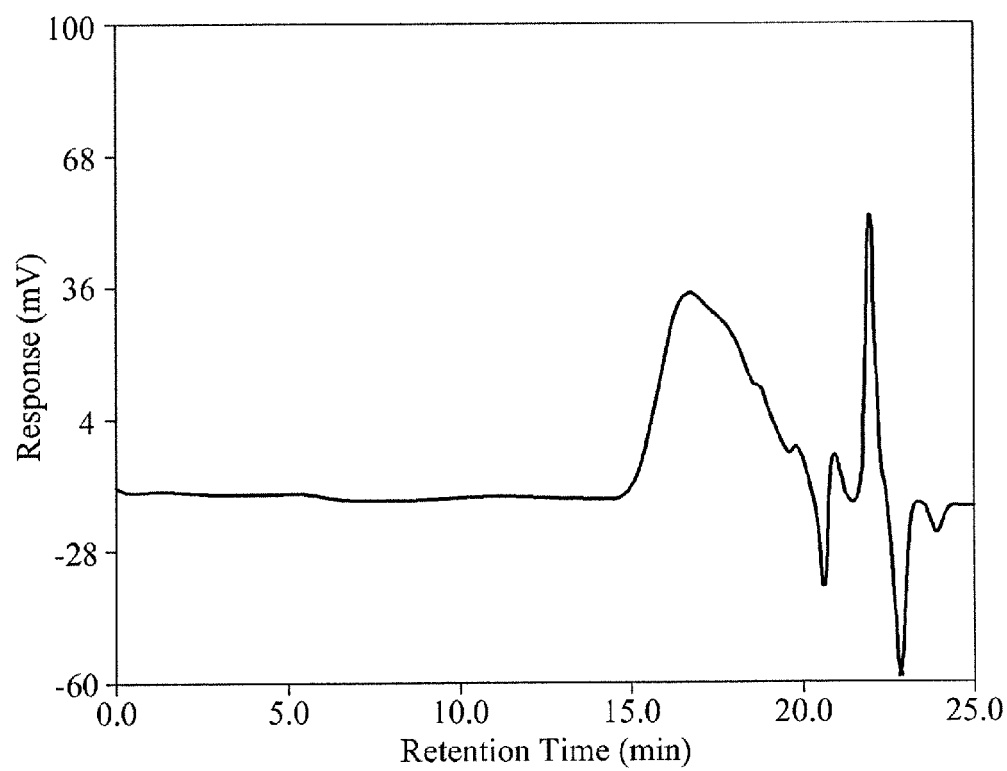
FIG. 20 is a graph illustrating GPC data of a copolymer obtained according to a synthesis example 18.

About 5.3 g of 2-methyl-2-adamantyl acrylate, about 3.4 g of γ-butyrolactyl methacrylate, about 4.7 g of 3-hydroxy-1-adamantyl methacrylate, and about 2.5 g of the benzoic acid-2,2-difluoro-2-sulfo-ethyl ester diphenyl-4-methacroyloxy-phenylsulfonium salt manufactured in the synthesis example 10 which act as monomers for polymerization were prepared, and dissolved in about 21 g of 1,2-dichloroethane. Next, about 0.75 g of norbornene, about 1.8 g of AIBN of a polymerization initiator, and about 42 g of 1,2-dichloroethane of a polymerization solvent were added in a flask of about 250 ml, and stirred for about one hour at room temperature under injection of a nitrogen gas. Next, the monomers for polymerization were gradually dropped on the flask for about one hour while maintaining a temperature of a reaction container at about 65° C., and then a polymerization reaction was performed on the monomers for about 16 hours. Next, a reaction solution in which the polymerization reaction was completed was cooled to room temperature. Next, the reaction solution cooled to room temperature was precipitated in hexane, and then filtered. Next, the filtered solution was washed several times using an identical solvent to a solvent used when being filtered, and then was subjected to drying under a reduced pressure to obtain about 14.3 g (a yield: 86%) of a copolymer represented as Chemical formula 11, and a structure of the copolymer was observed by $^1$H-NMR (see FIG. 19). Next, characteristics of a synthesized copolymer were measured using GPC, and the results are shown in FIG. 20. The GPC was performed under the same conditions as those in the synthesis example 15. According to the results of the GPC, a weight-average molecular weight (Mw) in terms of polystyrene of the copolymer was about 1,810, and a number-average molecular weight (Mn) was about 920, and a molecular weight distribution (Mw/Mn) was about 1.97.

Synthesis Example 19

Copolymer Synthesis

Figure 21:
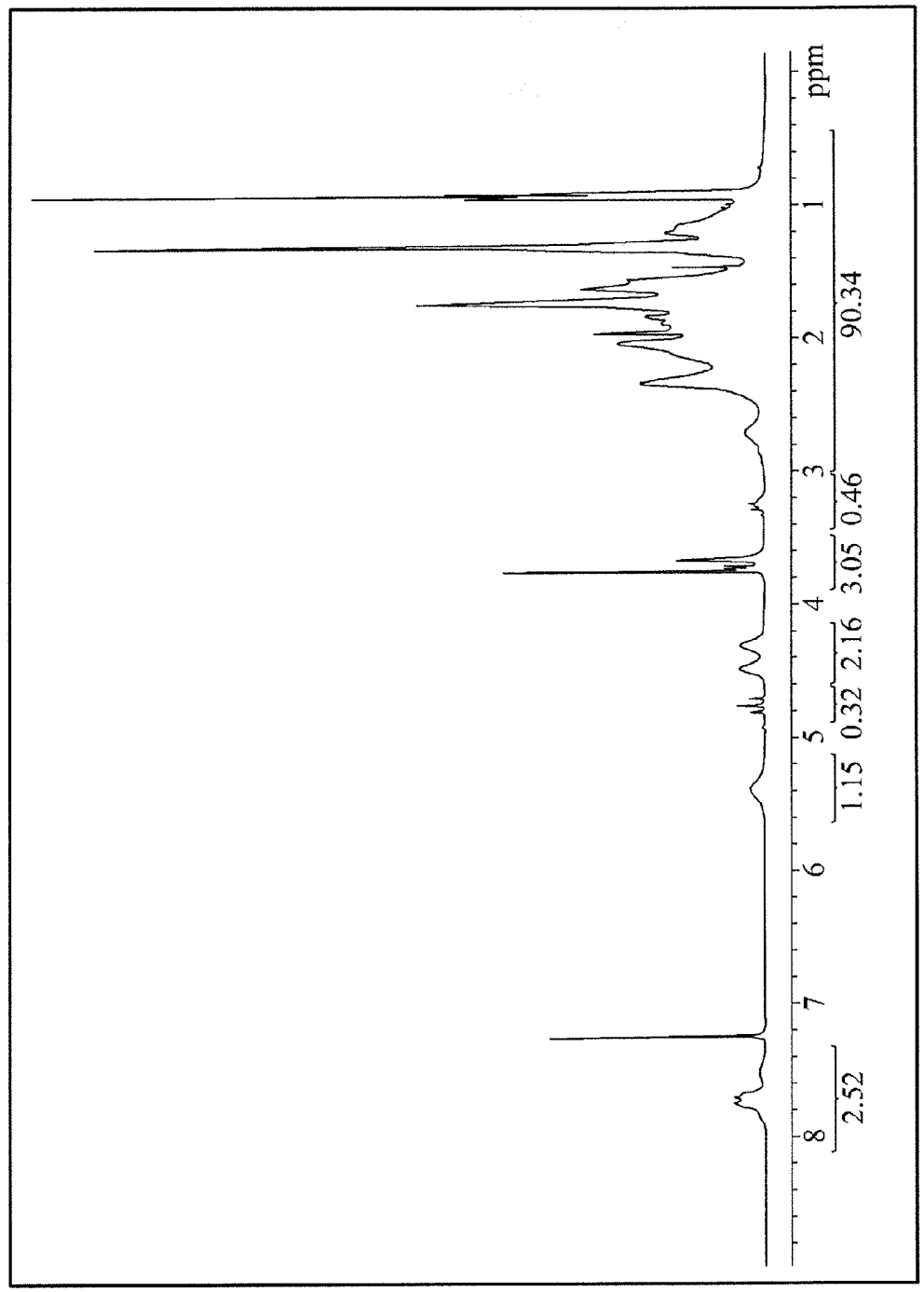
FIG. 21 illustrates a $^1$H-NMR spectrum of a copolymer obtained according to a synthesis example 19.
Figure 22:
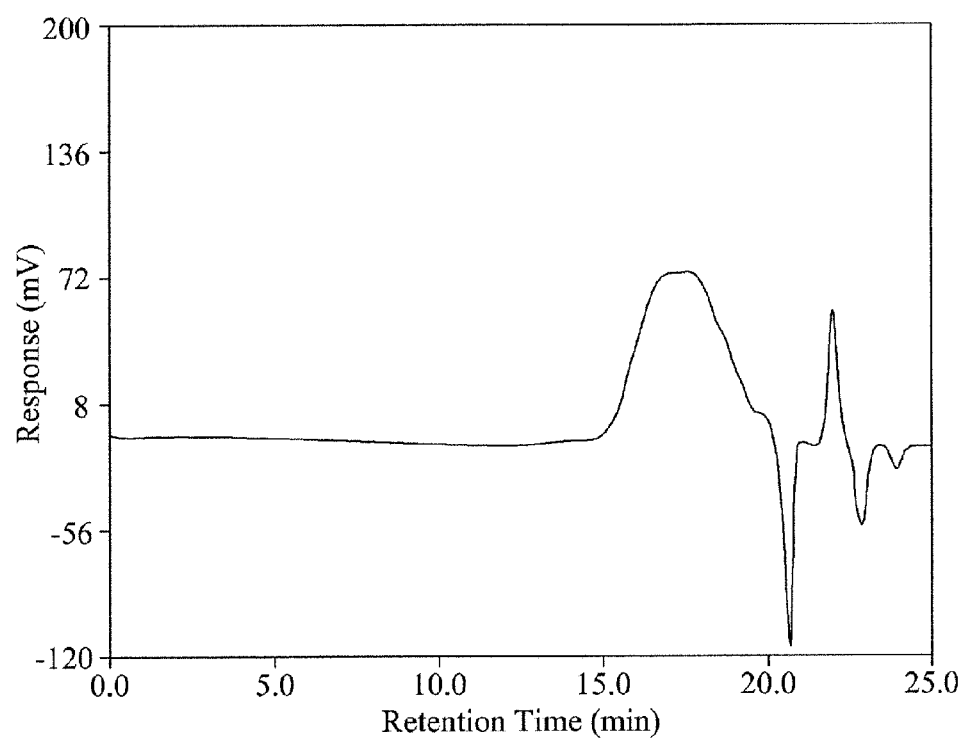
FIG. 22 is a graph illustrating GPC data of a copolymer obtained according to a synthesis example 19.

About 19.4 g of 2-methyl-2-adamantyl acrylate, about 12.5 g of γ-butyrolactyl methacrylate, about 17.3 g of 3-hydroxy-1-adamantyl methacrylate, and about 9.1 g of the adamantane-1-carboxylic acid-2,2-difluoro-2-sulfo-ethyl ester diphenyl-4-methacroyloxy-phenylsulfonium salt manufactured in the synthesis example 12 which act as monomers for polymerization were prepared, and dissolved in about 76.6 g of 1,2-dichloroethane. Next, about 2.8 g of norbornene, about 6.4 g of AIBN of a polymerization initiator, and about 153.3 g of 1,2-dichloroethane of a polymerization solvent were added in a flask of about 500 ml, and stirred for about one hour at room temperature under injection of a nitrogen gas. Next, the monomers for polymerization were gradually dropped on the flask for about one hour while maintaining a temperature of a reaction container at about 65° C., and then a polymerization reaction was performed on the monomers for about 16 hours. Next, a reaction solution in which the polymerization reaction was completed was cooled to room temperature. Next, the reaction solution cooled to room temperature was precipitated in hexane, and then filtered. Next, the filtered solution was washed several times using an identical solvent to a solvent used when being filtered, and then was subjected to drying under a reduced pressure to obtain about 50.6 g (a yield: 83%) of a copolymer represented as Chemical formula 12, and a structure of the copolymer was observed by $^1$H-NMR (see FIG. 21). Next, characteristics of a synthesized copolymer were measured using GPC, and the results are shown in FIG. 22. The GPC was performed under the same conditions as those in the synthesis example 15. According to the results of the GPC, a weight-average molecular weight (Mw) in terms of polystyrene of the copolymer was about 1,530, a number-average molecular weight (Mn) was about 790, and a molecular weight distribution (Mw/Mn) was about 1.947.

Synthesis Example 20

Copolymer Synthesis

Figure 23:
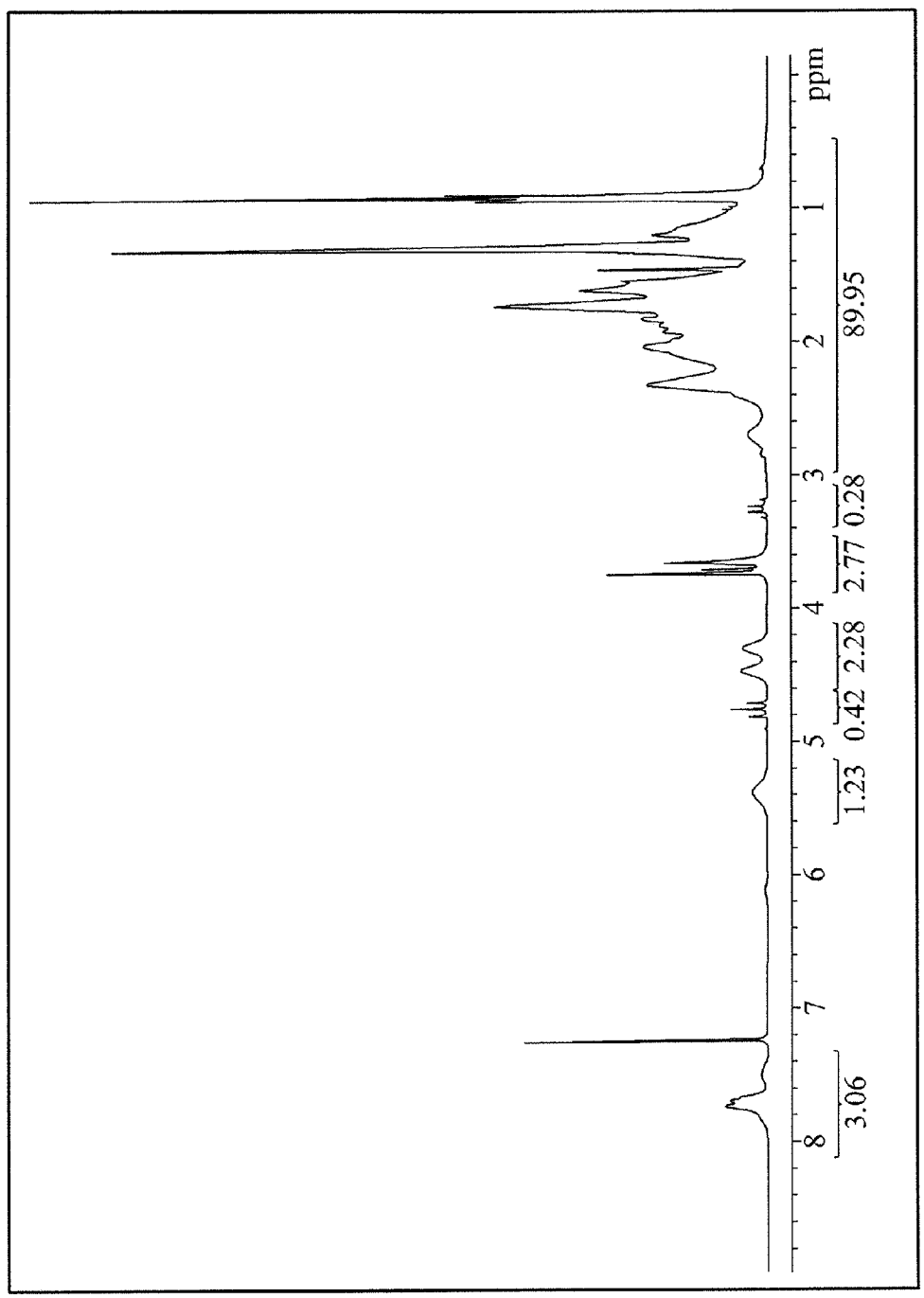
FIG. 23 illustrates a $^1$H-NMR spectrum of a copolymer obtained according to a synthesis example 20.
Figure 24:
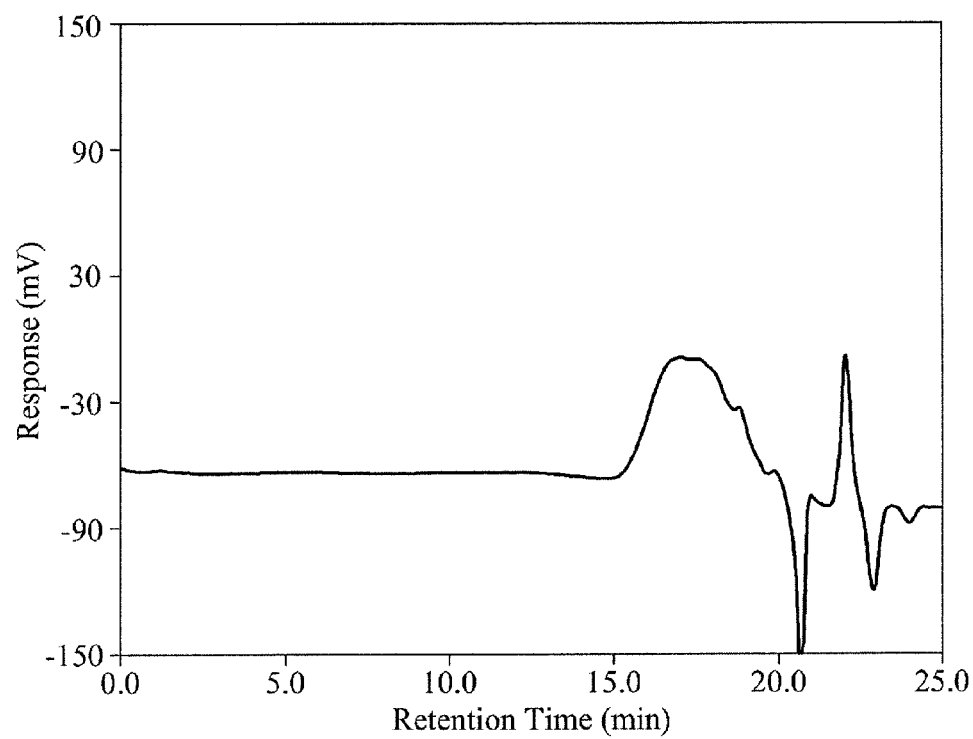
FIG. 24 is a graph illustrating GPC data of a copolymer obtained according to a synthesis example 20.

About 16.8 g of 2-methyl-2-adamantyl acrylate, about 10.8 g of γ-butyrolactyl methacrylate, about 15.0 g of 3-hydroxy-1-adamantyl methacrylate, and about 7.9 g of the cyclohexanecarboxylic acid-2,2-difluoro-2-sulfo-ethyl ester diphenyl-4-methacroyloxy-phenylsulfonium salt manufactured in the synthesis example 14 which act as monomers for polymerization were prepared, and dissolved in about 66.5 g of 1,2-dichloroethane. Next, about 2.4 g of norbornene, about 5.6 g of AIBN of a polymerization initiator, and about 133.1 g of 1,2-dichloroethane of a polymerization solvent were added in a flask of about 500 ml, and stirred for about one hour at room temperature under injection of a nitrogen gas. Next, the monomers for polymerization were gradually dropped on the flask for about one hour while maintaining a temperature of a reaction container at about 65° C., and then a polymerization reaction was performed on the monomers for about 16 hours. Next, a reaction solution in which the polymerization reaction was completed was cooled to room temperature. Next, the reaction solution cooled to room temperature was precipitated in hexane, and then filtered. Next, the filtered solution was washed several times using an identical solvent to a solvent used when being filtered, and then was subjected to drying under a reduced pressure to obtain about 42 g (a yield: 79%) of a copolymer represented as Chemical formula 13, and a structure of the copolymer was observed by $^1$H-NMR (see FIG. 23). Next, characteristics of a synthesized copolymer were measured using GPC, and the results are shown in FIG. 24. The GPC was performed under the same conditions as those in the synthesis example 15. According to the results of the GPC, a weight-average molecular weight (Mw) in terms of polystyrene of the copolymer was about 1,420, and a number-average molecular weight (Mn) was about 730, and a molecular weight distribution (Mw/Mn) was about 1.95.

Synthesis Example 21

Copolymer Synthesis

Figure 25:
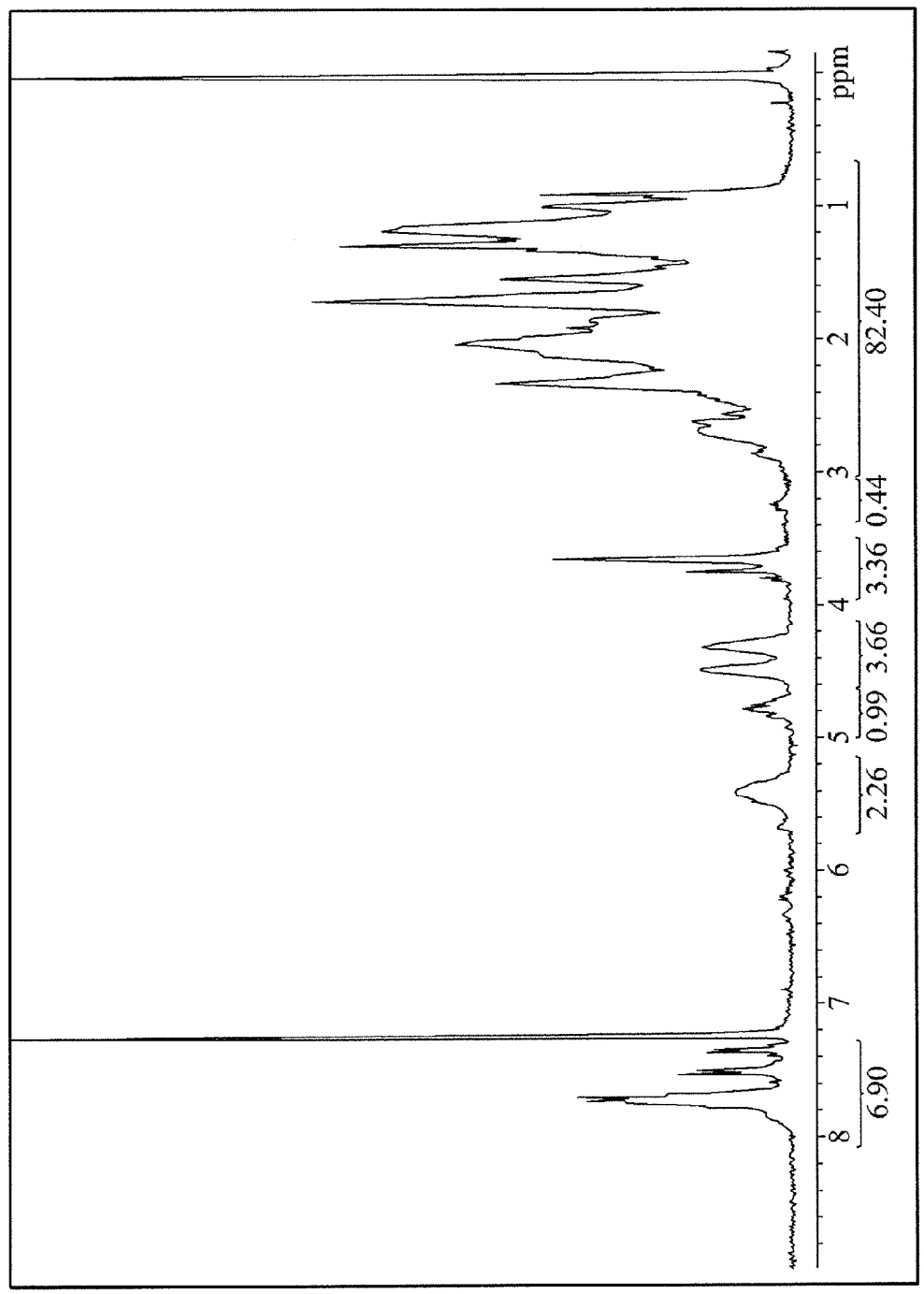
FIG. 25 illustrates a $^1$H-NMR spectrum of a copolymer obtained according to a synthesis example 21.
Figure 26:
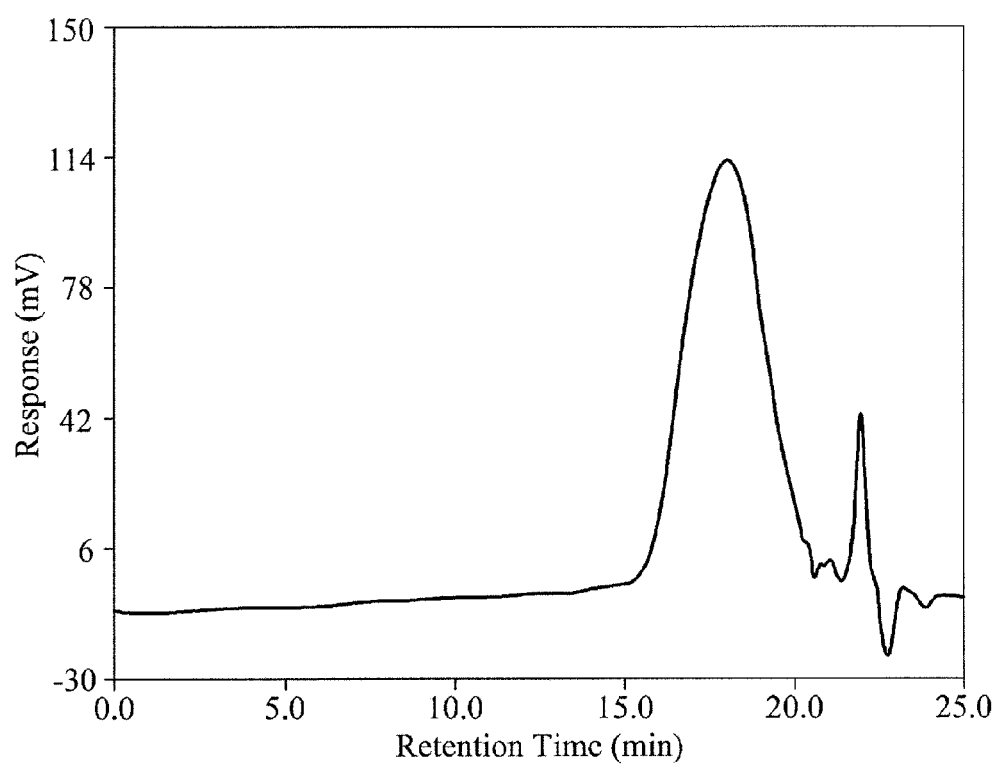
FIG. 26 is a graph illustrating GPC data of a copolymer obtained according to a synthesis example 21.

About 10.9 g of 2-Isopropyl-2-adamantyl methacrylate, about 10.8 g of γ-butyrolactyl acrylate, about 8.2 g of 3-hydroxy-1-adamantyl methacrylate, and about 4.3 g of the bicyclo[2.2.1]heptane-2-carboxylic acid-2,2-difluoro-2-sulfoethyl ester diphenyl-4-methacroyloxy-phenylsulfonium salt manufactured in the synthesis example 5 which act as monomers for polymerization were prepared, and dissolved in about 38.4 g of 1,2-dichloroethane. Next, about 1.3 g of norbornene, about 3.0 g of AIBN of a polymerization initiator, and about 76.8 g of 1,2-dichloroethane of a polymerization solvent were added in a flask of about 500 ml, and stirred for about one hour at room temperature under injection of a nitrogen gas. Next, the monomers for polymerization were gradually dropped on the flask for about one hour while maintaining a temperature of a reaction container at about 65° C., and then a polymerization reaction was performed on the monomers for about 16 hours. Next, a reaction solution in which the polymerization reaction was completed was cooled to room temperature. Next, the reaction solution cooled to room temperature was precipitated in hexane, and then filtered. Next, the filtered solution was washed several times using an identical solvent to a solvent used when being filtered, and then was subjected to drying under a reduced pressure to obtain about 30 g (a yield: 84%) of a copolymer represented as Chemical formula 14, and a structure of the copolymer was observed by $^1$H-NMR (see FIG. 25). Next, characteristics of a synthesized copolymer were measured using GPC, and the results are shown in FIG. 26. The GPC was performed under the same conditions as those in the synthesis example 15. According to the results of the GPC, a weight-average molecular weight (Mw) in terms of polystyrene of the copolymer was about 810, and a number-average molecular weight (Mn) was about 310, and a molecular weight distribution (Mw/Mn) was about 2.61.

Synthesis Example 22

Copolymer Synthesis

Figure 27:
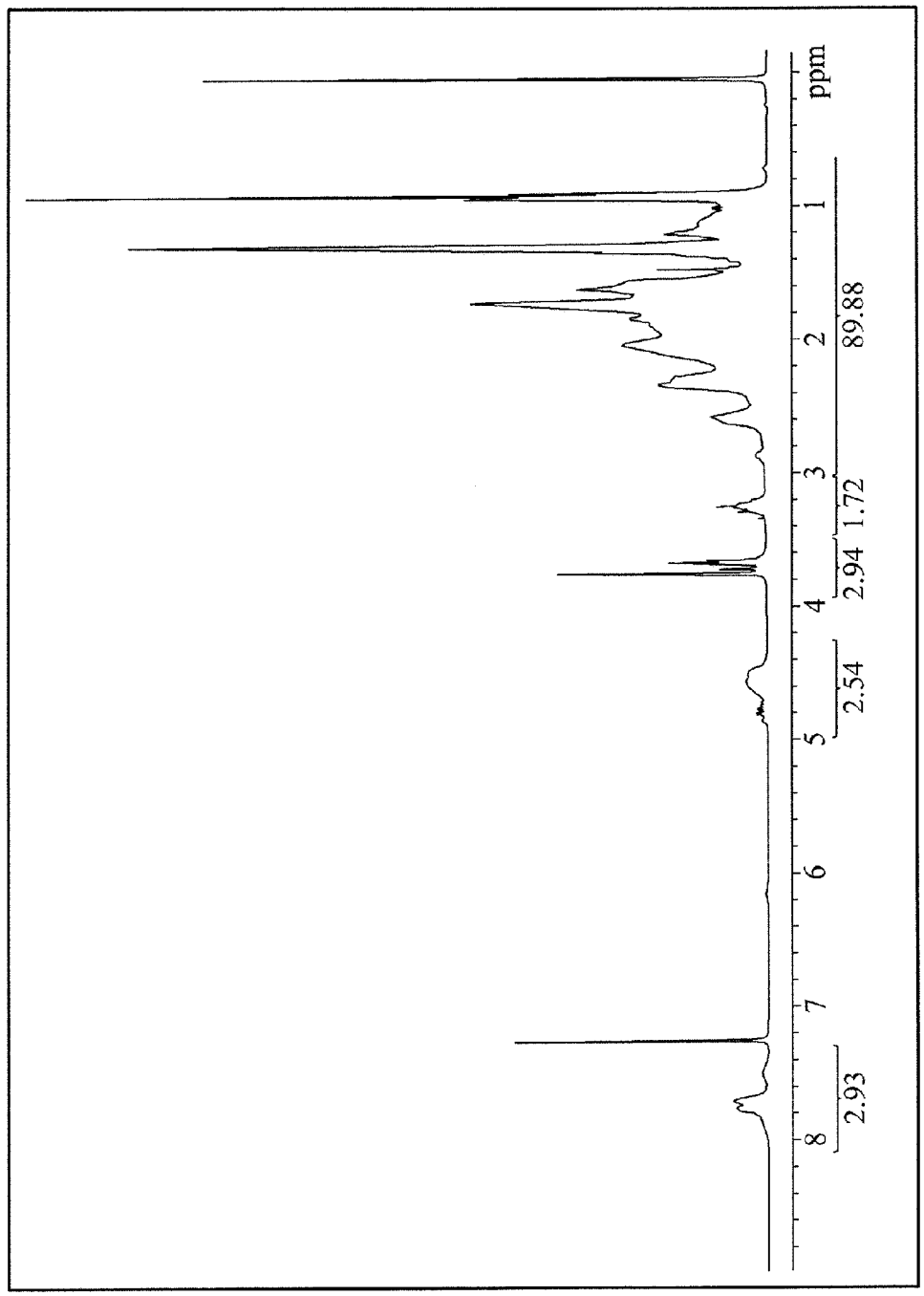
FIG. 27 illustrates a $^1$H-NMR spectrum of a copolymer obtained according to a synthesis example 22.
Figure 28:
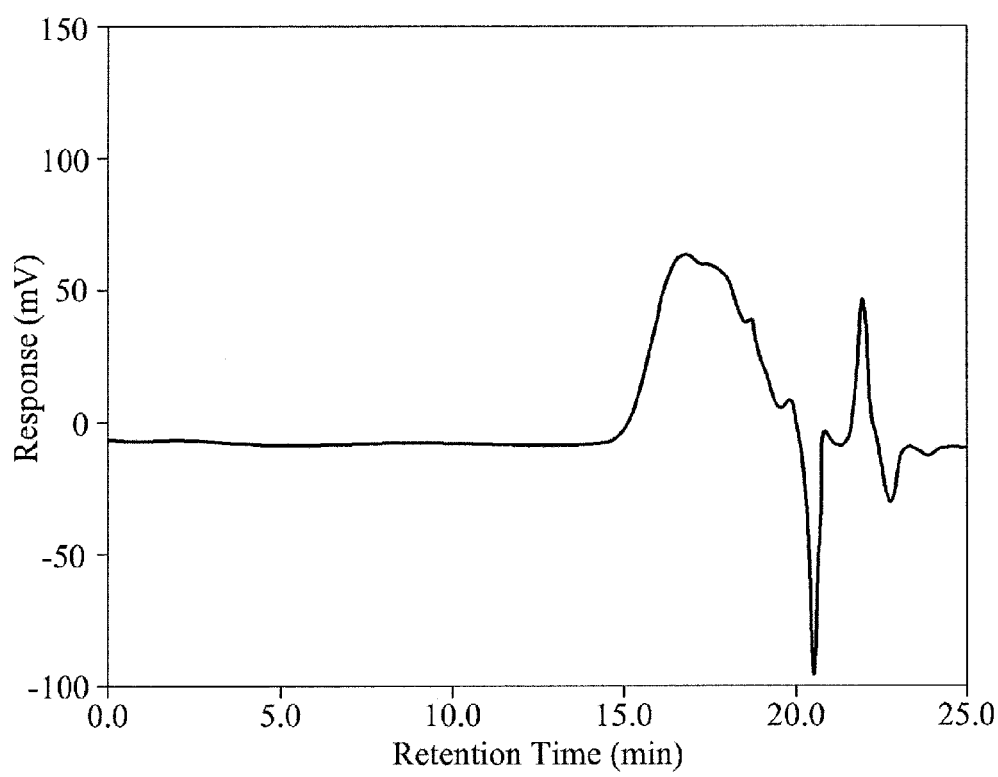
FIG. 28 is a graph illustrating GPC data of a copolymer obtained according to a synthesis example 22.

About 10.7 g of 2-methyl-2-adamantyl acrylate, about 9 g of 5-methacryloyloxy-2,6-norbornanecarbolactone, about 9.5 g of 3-hydroxy-1-adamantyl methacrylate, and about 5 g of the bicyclo[2.2.1]heptane-2-carboxylic acid-2,2-difluoro-2-sulfo-ethyl ester diphenyl-4-methacroyloxy-phenylsulfonium salt manufactured in the synthesis example 5 which act as monomers for polymerization were prepared, and dissolved in about 44.9 g of 1,2-dichloroethane. Next, about 1.5 g of norbornene, about 5.6 g of AIBN of a polymerization initiator, and about 89.7 g of 1,2-dichloroethane of a polymerization solvent were added in a flask of about 500 ml, and stirred for about one hour at room temperature under injection of a nitrogen gas. Next, the monomers for polymerization were gradually dropped on the flask for about one hour while maintaining a temperature of a reaction container at about 65° C., and then a polymerization reaction was performed on the monomers for about 16 hours. Next, a reaction solution in which the polymerization reaction was completed was cooled to room temperature. Next, the reaction solution cooled to room temperature was precipitated in hexane, and then filtered. Next, the filtered solution was washed several times using an identical solvent to a solvent used when being filtered, and then was subjected to drying under a reduced pressure to obtain about 28 g (a yield: 79%) of a copolymer represented as Chemical formula 21, and a structure of the copolymer was observed by (see FIG. 27). Next, characteristics of a synthesized copolymer were measured using GPC, and the results are shown in FIG. 28. The GPC was performed under the same conditions as those in the synthesis example 15. According to the results of the GPC, a weight-average molecular weight (Mw) in terms of polystyrene of the copolymer was about 1,590, and a number-average molecular weight (Mn) was about 791, and a molecular weight distribution (Mw/Mn) was about 2.01.

EXAMPLES

1. Manufacturing Chemically Amplified Resist Composition

Example 1

About 100 parts by weight of the copolymer obtained in the synthesis example 15, about 2.5 parts by weight of triphenylsulfonium nonaflate of a photoacid generator, and about 0.75 parts by weight of tetramethylammonium hydroxide of a basic additive were dissolved in about 1,000 parts by weight of propylene glycol methyl ether acetate, and then filtered using a membrane filter of about 0.2 μm to manufacture a chemically amplified resist composition.

Example 2

A chemically amplified resist composition was manufactured in the same manner as in the Example 1, except that triphenylsulfonium nonaflate was not added.

Example 3

A chemically amplified resist composition was manufactured in the same manner as in the Example 2, except that about 100 parts by weight of the copolymer obtained in the synthesis example 19 was used instead of using about 100 parts by weight of the copolymer obtained in the synthesis example 15.

Example 4

A chemically amplified resist composition was manufactured in the same manner as in the Example 2, except that about 100 parts by weight of the copolymer obtained in the synthesis example 20 was used instead of using about 100 parts by weight of the copolymer obtained in the synthesis example 15.

Example 5

A chemically amplified resist composition was manufactured in the same manner as in the Example 2, except that about 1 part by weight of tetramethylammonium hydroxide was used as the basic additive.

Example 6

A chemically amplified resist composition was manufactured in the same manner as in the Example 3, except that about 1 part by weight of tetramethylammonium hydroxide was used as the basic additive.

Example 7

A chemically amplified resist composition was manufactured in the same manner as in the Example 4, except that about 1 part by weight of tetramethylammonium hydroxide was used as the basic additive.

Example 8

A chemically amplified resist composition was manufactured in the same manner as in the Example 2, except that about 1.25 parts by weight of tetramethylammonium hydroxide was used as the basic additive.

Example 9

A chemically amplified resist composition was manufactured in the same manner as in the Example 3, except that about 1.25 parts by weight of tetramethylammonium hydroxide was used as the basic additive.

Example 10

A chemically amplified resist composition was manufactured in the same manner as in the Example 4, except that about 1.25 parts by weight of tetramethylammonium hydroxide was used as the basic additive.

Comparative Example 1

A chemically amplified resist composition was manufactured in the same manner as in the Example 1, except that about 100 parts by weight of a methacrylate copolymer represented as Chemical formula 22 below was used instead of using about 100 parts by weight of the copolymer obtained in the synthesis example 15.

[Chemical formula 22]

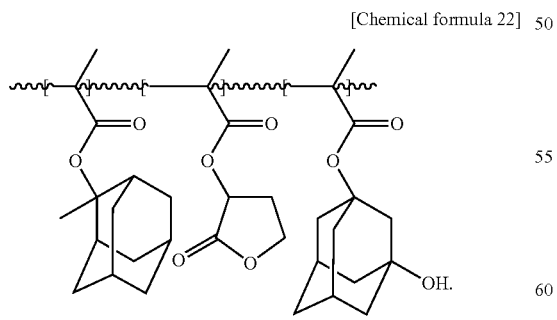

Comparative Example 2

A chemically amplified resist composition was manufactured in the same manner as in the Comparative Example 1, except that about 1 parts by weight of tetramethylammonium hydroxide was used as the basic additive.

Comparative Example 3

A chemically amplified resist composition was manufactured in the same manner as in the Comparative Example 1, except that about 1.25 parts by weight of tetramethylammonium hydroxide was used as the basic additive.

2. Estimating Characteristics of Chemically Amplified Resist Composition

The chemically amplified resist compositions respectively manufactured through Examples 1 to 10, and the Comparative Examples 1 to 3 were coated on a substrate using a spinner, and dried for about 90 seconds at about 110° C. to form a resist layer having a thickness of about 0.2 μm. Next, the formed resist layer was exposed using an ArF excimer laser stepper (lens numerical aperture: about 0.75), and subjected to a heat treatment at about 120° C. for about 90 seconds. Next, the resist layer was developed for about 40 seconds using about 2.38 wt % of a tetramethylammonium hydroxide aqueous solution, and then washed and dried to form a resist pattern. In this regard, sensitivity, resolution, and characteristics of line edge roughness were measured, and the results are shown in Table 1 below. Here, the sensitivity may denote an optimal exposure amount enabling a Line and Space (L/S) pattern of about 0.12 μm formed after developing to be formed to have a line width of 1:1. Also, the resolution may denote a minimal pattern numerical value formed in the sensitivity. Also, the line edge roughness was measured using a critical-dimension-measurement scanning electron microscope (CD-SEM), and a degree of the line edge roughness was classified into five levels, which were 1 (significantly bad), 2 (bad), 3 (moderate), 4 (good), and 5 (significantly good).

TABLE 1

|  | Sensitivity (mJ/cm$^2$) | Resolution (nm) | Line edge roughness |
|---|---|---|---|
| Example 1 | 10 | 100 | 5 |
| Example 2 | 15 | 90 | 4 |
| Example 3 | 14 | 100 | 3 |
| Example 4 | 16 | 100 | 5 |
| Example 5 | 11 | 110 | 4 |
| Example 6 | 11 | 100 | 4 |
| Example 7 | 13 | 120 | 5 |
| Example 8 | 10 | 110 | 3 |
| Example 9 | 10 | 120 | 4 |
| Example 10 | 11 | 120 | 5 |
| Comparative Example 1 | 16 | 90 | 3 |
| Comparative Example 2 | 15 | 100 | 4 |
| Comparative Example 3 | 17 | 100 | 2 |

Referring to Table 1, the resolutions in the Examples and Comparative Examples were similar, however, the sensitivity and characteristics of line edge roughness were relatively excellent in the Examples than in the Comparative Examples. Particularly, the sensitivity was significantly excellent in Examples 1, 8, and 9, and the characteristics of line edge roughness was significantly excellent in Examples 1, 4, 7, and 10.

As described above, according to the exemplary embodiments, the PAG is connected with a main chain of the copolymer, whereby the PAG may be equally dispersed within the resist layer. As a result, characteristics of line edge roughness of the resist pattern may be improved. Also, when the resist pattern is formed on the substrate using the chemically amplified resist composition including the copolymer, etch resistance of the resist pattern may be improved. In addition, the resist layer formed on the substrate may have a high sensitivity, a high thermal stability, a high adhesive strength with respect to the substrate, a high transparence with respect to an exposure light, and the resist pattern may have a high resolution.

Although a few exemplary embodiments of the present invention have been shown and described, the present invention is not limited to the described exemplary embodiments. Instead, it would be appreciated by those skilled in the art that changes may be made to these exemplary embodiments without departing from the principles and spirit of the invention, the scope of which is defined by the claims and their equivalents.

What is claimed is:

1. A photoacid generator represented as

[Chemical formula 1]

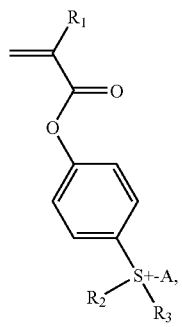

wherein $R_1$ is a $C_1$-$C_5$ alkoxy group,
$R_2$ and $R_3$ are respectively a linear or branched $C_1$-$C_{20}$ alkyl group, an aryl group, a linear or branched $C_1$-$C_{20}$ perfluoroalkyl group, a benzyl group, or a $C_6$-$C_{20}$ aryl group, and $A^-$ is a compound represented as

[Chemical formula 2]

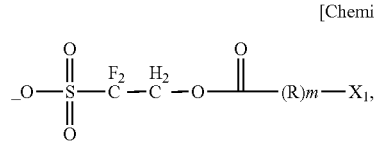

wherein $X_1$ is a monocyclic or polycyclic $C_3$-$C_{20}$ hydrocarbon group, a benzyl group, a $C_6$-$C_{20}$ aryl group, a $C_1$-$C_{10}$ alkyl group, a $C_1$-$C_{10}$ alkoxy group, a $C_1$-$C_{10}$ hydroxy alkyl group, or a cyano group, at least one hydrogen atom of the monocyclic or polycyclic $C_3$-$C_{20}$ hydrocarbon group is or is not substituted with an ether group, an ester group, a carbonyl group, an acetal group, a nitrile group, a cyano group, a hydroxy group, a carboxyl group, or an aldehyde group, R is a $C_1$-$C_{10}$ alkyl group, a $C_1$-$C_{10}$ alkoxy group, a nitrogen atom, a sulfur atom, or an oxygen atom, and m is a positive integer of 0 to 2.

2. The photoacid generator of claim 1, wherein the photoacid generator is obtained through a synthesis reaction of a compound represented as Chemical formula 3 below and a salt represented as Chemical formula 4 below:

[Chemical formula 3]

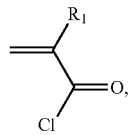

wherein $R_1$ is a $C_1$-$C_5$ alkoxy group; and

[Chemical formula 4]

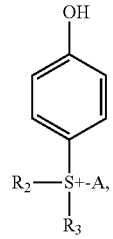

wherein $R_2$ and $R_3$ are respectively a linear or branched $C_1$-$C_{20}$ alkyl group, an aryl group, a linear or branched $C_1$-$C_{20}$ perfluoroalkyl group, a benzyl group, or a $C_6$-$C_{20}$ aryl group, and $A^-$ is a compound represented as Chemical formula 2.

3. A copolymer for a chemically amplified resist composition in which a photoacid generator represented as Chemical formula 1 below is connected with a main chain of the copolymer:

[Chemical formula 1]

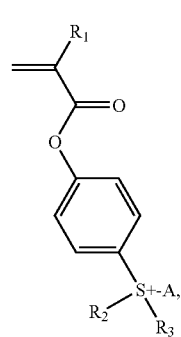

wherein $R_1$ is a $C_1$-$C_5$ alkoxy group,
$R_2$ and $R_3$ are respectively a linear or branched $C_1$-$C_{20}$ alkyl group, an aryl group, a linear or branched $C_1$-$C_{20}$ perfluoroalkyl group, a benzyl group, or a $C_6$-$C_{20}$ aryl group,
and $A^-$ is a compound represented as

[Chemical formula 2]

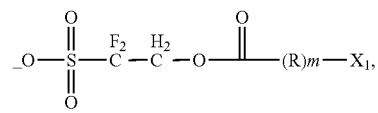

wherein $X_1$ is a monocyclic or polycyclic $C_3$-$C_{20}$ hydrocarbon group, a benzyl group, a $C_6$-$C_{20}$ aryl group, a $C_1$-$C_{10}$ alkyl group, a $C_1$-$C_{10}$ alkoxy group, a $C_1$-$C_{10}$ hydroxy alkyl group, or a cyano group, at least one hydrogen atom of the monocyclic or polycyclic $C_3$-$C_{20}$ hydrocarbon group is or is not substituted with an ether group, an ester group, a carbonyl group, an acetal group, a nitrile group, a cyano group, a hydroxy group, a carboxyl group, or an aldehyde group, R is a $C_1$-$C_{10}$ alkyl group, a $C_1$-$C_{10}$ alkoxy group, a nitrogen atom, a sulfur atom, or an oxygen atom, and m is a positive integer of 0 to 2.

4. The copolymer of claim 3, wherein the copolymer includes a repeating unit having the photoacid generator.

5. The copolymer of claim 3, wherein the copolymer further includes at least one of a repeating unit having an acid labile group, a repeating unit having a lactone ring, and a repeating unit having a hydroxy group.

6. The copolymer of claim 3, wherein the copolymer for a chemically amplified resist composition is represented as the copolymer:

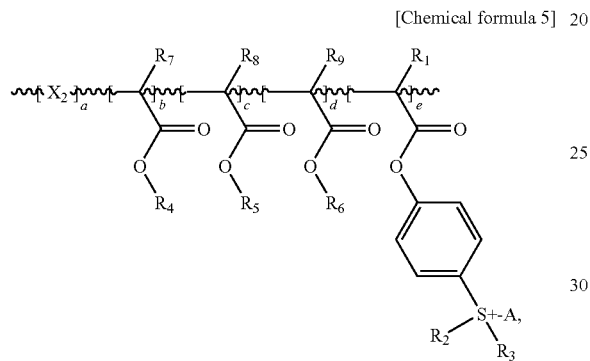

[Chemical formula 5]

wherein $R_1$ is a $C_1$-$C_5$ alkoxy group, $R_2$ and $R_3$ are respectively a linear or branched $C_1$-$C_{20}$ alkyl group, an aryl group, a linear or branched $C_1$-$C_{20}$ perfluoroalkyl group, a benzyl group, or a $C_6$-$C_{20}$ aryl group, $R_4$, $R_5$ and $R_6$ are respectively a hydrogen atom, or a $C_1$-$C_{30}$ alkyl group including or not including an ether group, an ester group, a carbonyl group, an acetal group, an epoxy group, a nitrile group, or an aldehyde group, $R_7$, $R_8$ and $R_9$ are respectively a hydrogen atom, a methyl group, or a trifluoromethyl group, $X_2$ is olefin, vinyl, styrene, or a derivative thereof, a, b, c, d, and e respectively satisfy $0.01 < a/(a+b+c+d+e) < 0.4$; $0.01 < b/(a+b+c+d+e) < 0.3$; $0.01 < c/(a+b+c+d+e) < 0.3$; $0.01 < d/(a+b+c+d+e) < 0.3$; $0.01 < e/(a+b+c+d+e) < 0.15$, and $A^-$ is a compound represented as

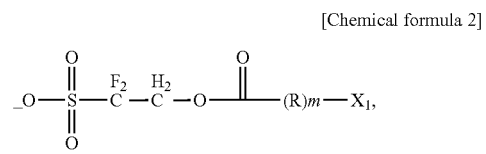

[Chemical formula 2]

wherein $X_1$ is a monocyclic or polycyclic $C_3$-$C_{20}$ hydrocarbon group, a benzyl group, a $C_6$-$C_{20}$ aryl group, a $C_1$-$C_{10}$ alkyl group, a $C_1$-$C_{10}$ alkoxy group, a $C_1$-$C_{10}$ hydroxy alkyl group, or a cyano group, at least one hydrogen atom of the monocyclic or polycyclic $C_3$-$C_{20}$ hydrocarbon group is or is not substituted with an ether group, an ester group, a carbonyl group, an acetal group, a nitrile group, a cyano group, a hydroxy group, a carboxyl group, or an aldehyde group, R is a $C_1$-$C_{10}$ alkyl group, a $C_1$-$C_{10}$ alkoxy group, a nitrogen atom, a sulfur atom, or an oxygen atom, and m is a positive integer of 0 to 2.

7. A chemically amplified resist composition including a copolymer and a solvent, in which a photoacid generator represented as Chemical formula 1 below is connected with a main chain of the copolymer:

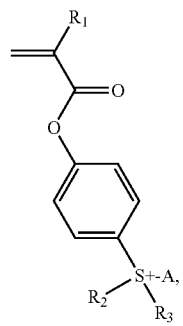

[Chemical formula 1]

wherein $R_1$ is a $C_1$-$C_5$ alkoxy group, $R_2$ and $R_3$ are respectively a linear or branched $C_1$-$C_{20}$ alkyl group, an aryl group, a linear or branched $C_1$-$C_{20}$ perfluoroalkyl group, a benzyl group, or a $C_6$-$C_{20}$ aryl group, and $A^-$ is a compound represented as

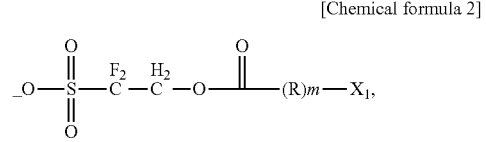

[Chemical formula 2]

wherein $X_1$ is a monocyclic or polycyclic $C_3$-$C_{20}$ hydrocarbon group, a benzyl group, a $C_6$-$C_{20}$ aryl group, a $C_1$-$C_{10}$ alkyl group, a $C_1$-$C_{10}$ alkoxy group, a $C_1$-$C_{10}$ hydroxy alkyl group, or a cyano group, at least one hydrogen atom of the monocyclic or polycyclic $C_3$-$C_{20}$ hydrocarbon group is or is not substituted with an ether group, an ester group, a carbonyl group, an acetal group, a nitrile group, a cyano group, a hydroxy group, a carboxyl group, or an aldehyde group, R is a $C_1$-$C_{10}$ alkyl group, a $C_1$-$C_{10}$ alkoxy group, a nitrogen atom, a sulfur atom, or an oxygen atom, and m is a positive integer of 0 to 2.

8. The chemically amplified resist composition of claim 7, wherein the copolymer is synthesized by polymerization of monomers including the photoacid generator, and about 0.5 to 15 parts by weight of the photoacid generator with respect to about 100 parts by weight of a total solid of the chemically amplified resist composition is used upon the polymerization.

9. The chemically amplified resist composition of claim 7, wherein an amount of the copolymer is about 3 wt. % to 20 wt. % with respect to a total amount of the chemically amplified resist composition.

10. A method of forming a pattern using a chemically amplified resist composition including a copolymer and a solvent, the method comprising:
coating a substrate with the chemically amplified resist composition including the copolymer and the solvent, a main chain of the copolymer being connected with a photoacid generator represented as Chemical formula 1 below, and drying the coated composition to form a resist layer;

selectively exposing the resist layer; and
developing the exposed resist layer:

[Chemical formula 1]

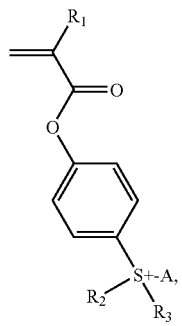

wherein $R_1$ is a $C_1$-$C_5$ alkoxy group, $R_2$ and $R_3$ are respectively a linear or branched $C_1$-$C_{20}$ alkyl group, an aryl group, a linear or branched $C_1$-$C_{20}$ perfluoroalkyl group, a benzyl group, or a $C_6$-$C_{20}$ aryl group, and $A^-$ is a compound represented as

[Chemical formula 2]

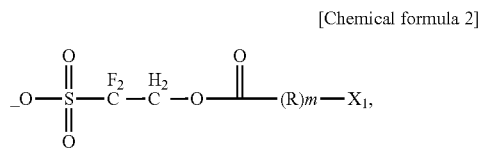

wherein $X_1$ is a monocyclic or polycyclic $C_3$-$C_{20}$ hydrocarbon group, a benzyl group, a $C_6$-$C_{20}$ aryl group, a $C_1$-$C_{10}$ alkyl group, a $C_1$-$C_{10}$ alkoxy group, a $C_1$-$C_{10}$ hydroxy alkyl group, or a cyano group, at least one hydrogen atom of the monocyclic or polycyclic $C_3$-$C_{20}$ hydrocarbon group is or is not substituted with an ether group, an ester group, a carbonyl group, an acetal group, a nitrile group, a cyano group, a hydroxy group, a carboxyl group, or an aldehyde group, R is a $C_1$-$C_{10}$ alkyl group, a $C_1$-$C_{10}$ alkoxy group, a nitrogen atom, a sulfur atom, or an oxygen atom, and m is a positive integer of 0 to 2.

11. The method of claim 10, wherein a light source for the exposing is any light source selected from a KrF excimer laser, an ArF excimer laser, an Extreme Ultra Violet (EUV) light, an X-ray, and an electron-beam (e-beam).

12. The method of claim 10, wherein a light wavelength of the light source for the exposing is about 180 nm to 250 nm.

13. The copolymer of claim 12, wherein the copolymer has a weight average molecular weight (Mw) of about 500 to 100,000.

14. The copolymer of claim 3, wherein the copolymer for a chemically amplified resist is represented as any copolymer of Chemical formulas below, which are

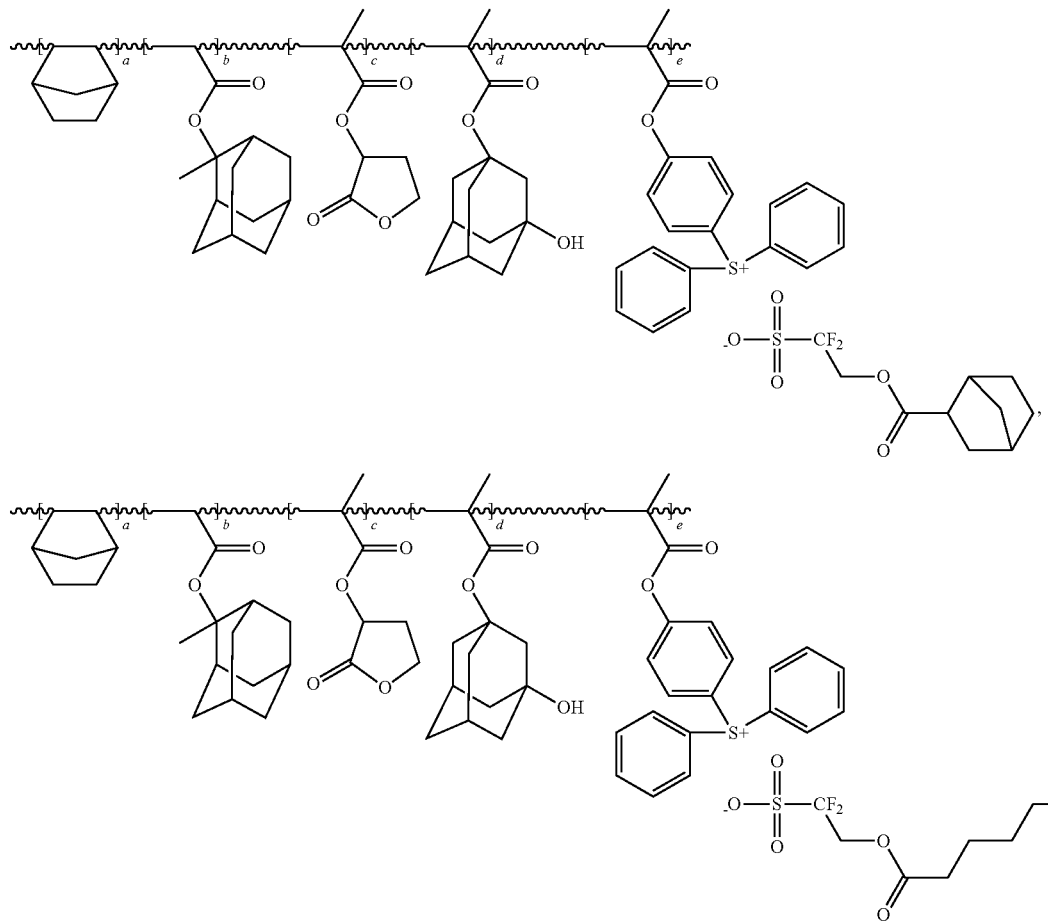

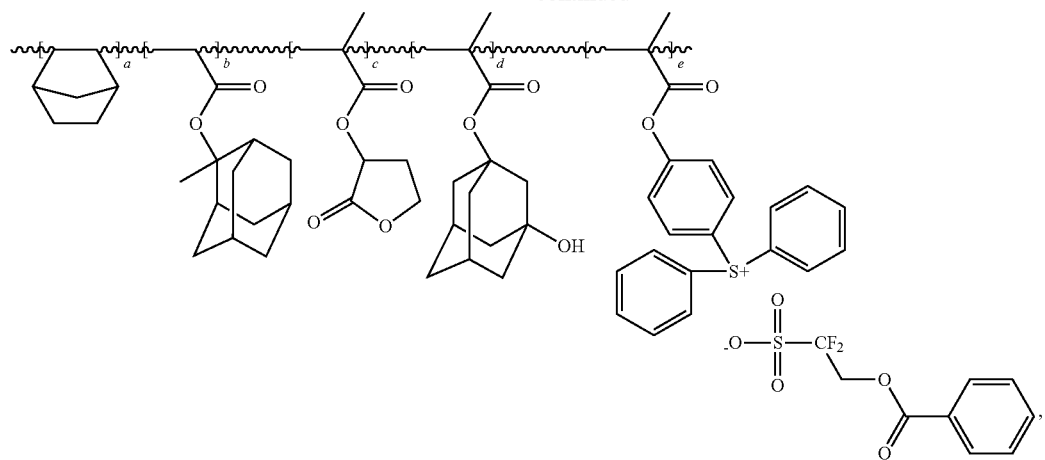
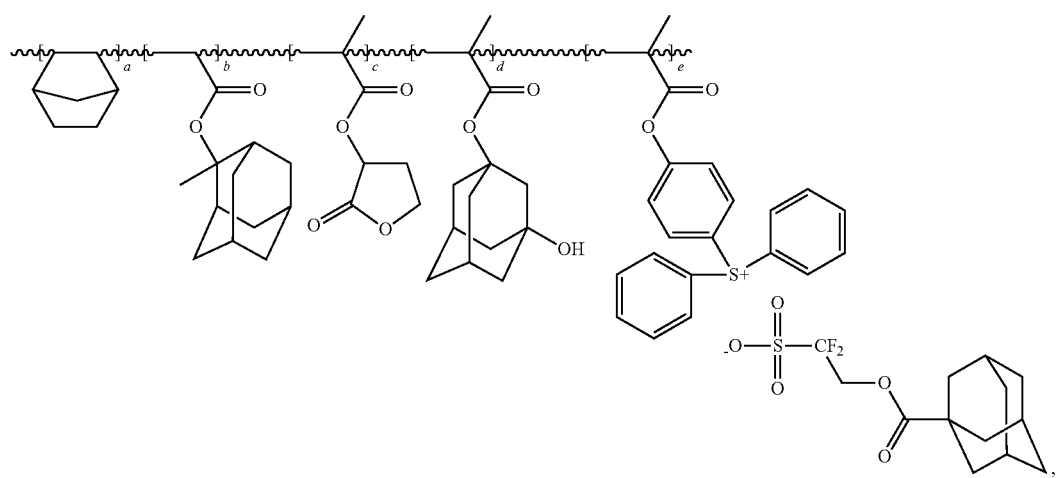
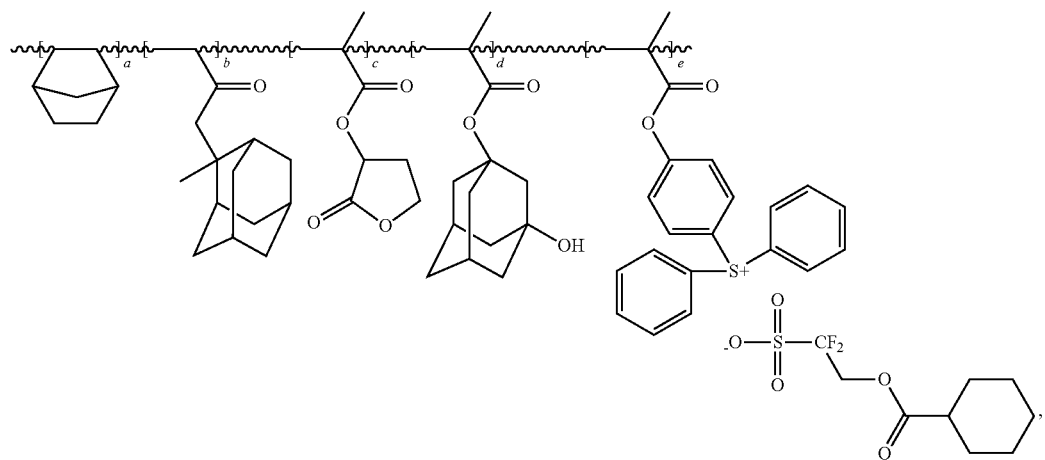

-continued
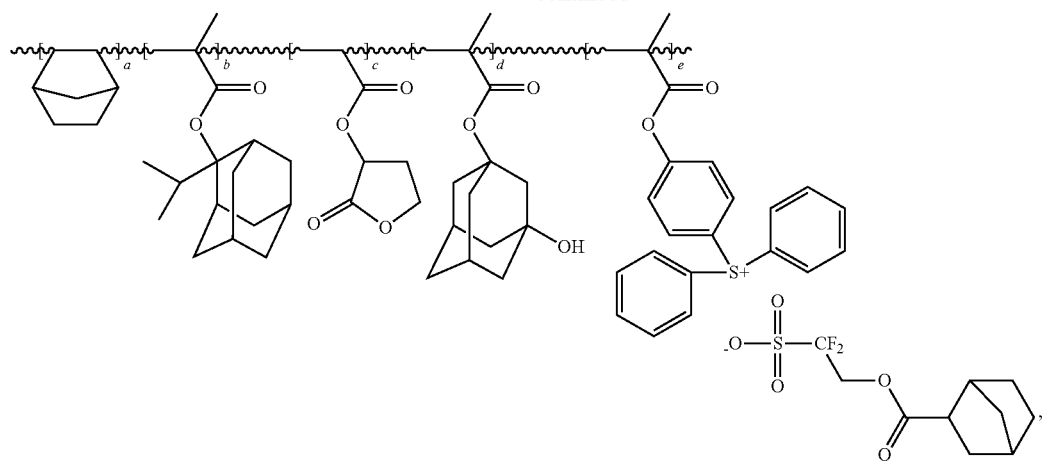
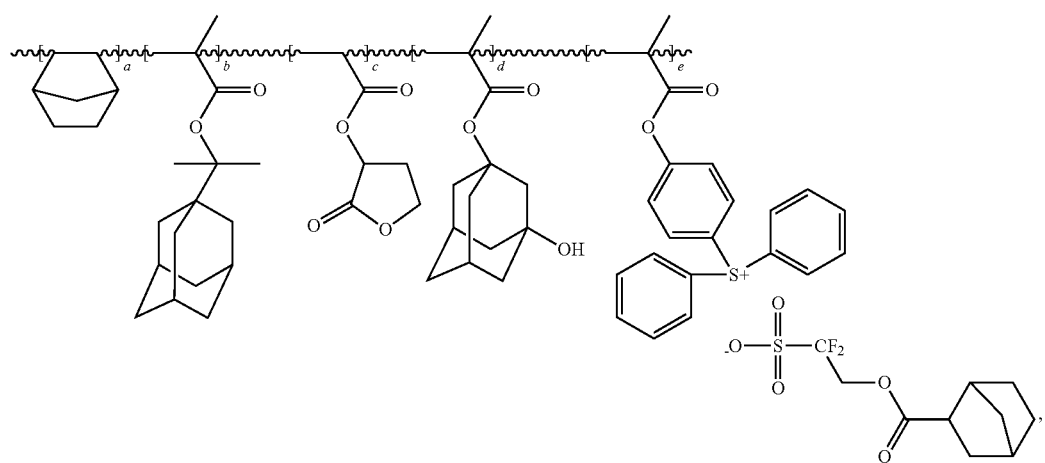
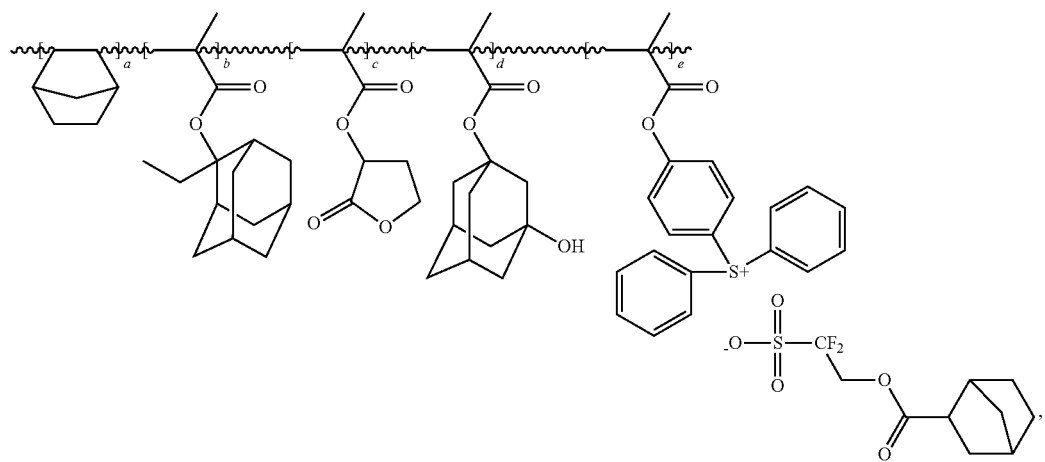

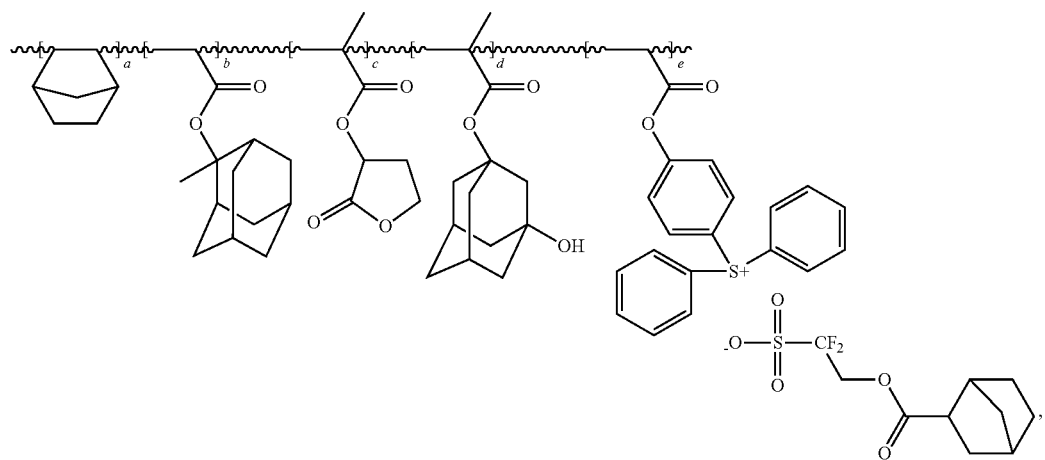
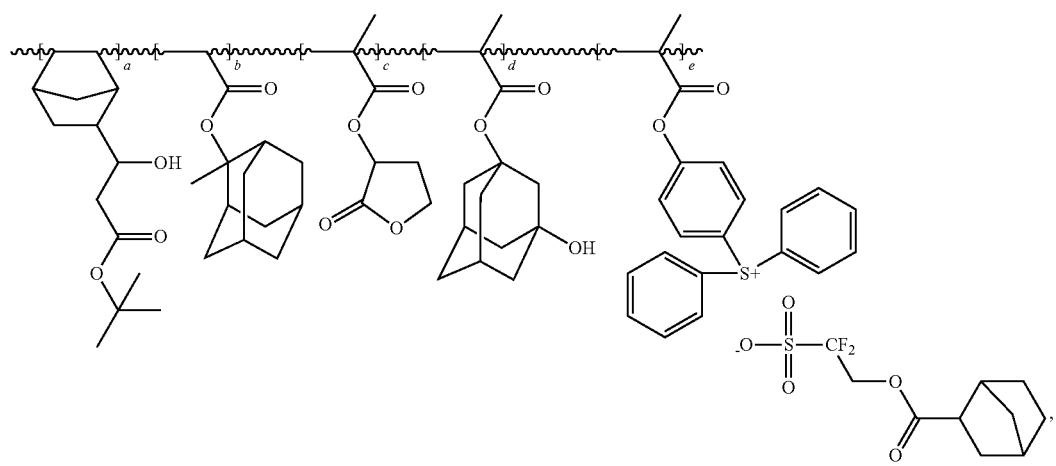
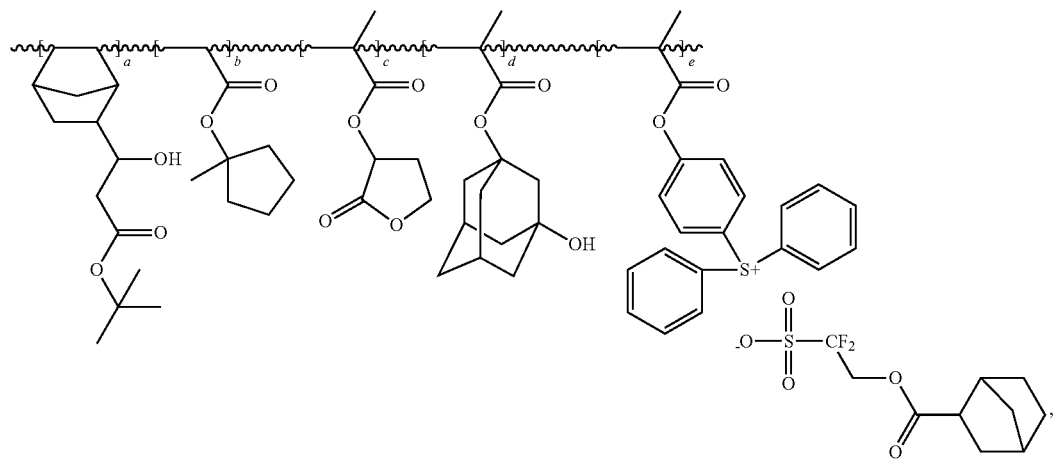

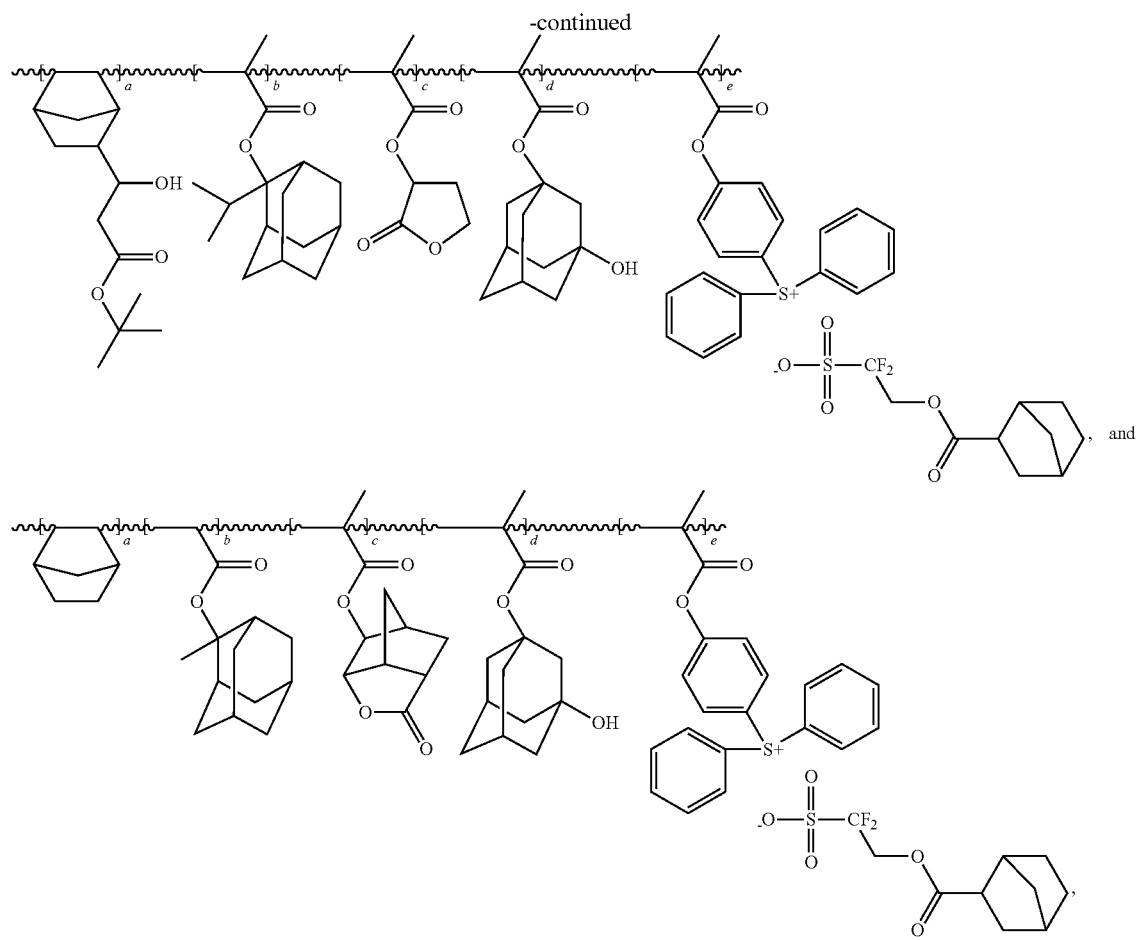
wherein a, b, c, d, and e respectively satisfy $0.01 < a/(a+b+c+d+e) < 0.4$; $0.01 < b/(a+b+c+d+e) < 0.3$; $0.01 < c/(a+b+c+d+e) < 0.3$; $0.01 < d/(a+b+c+d+e) < 0.3$; $0.01 < e/(a+b+c+d+e) < 0.15$.
* * * * *